(12) United States Patent
Bojarski et al.

(10) Patent No.: US 9,545,251 B2
(45) Date of Patent: Jan. 17, 2017

(54) APPARATUS FOR TISSUE REPAIR

(71) Applicant: Smith & Nephew, Inc., Memphis, TN (US)

(72) Inventors: Raymond A. Bojarski, Attleboro, MA (US); George Sikora, Bridgewater, MA (US); Paul Alexander Torrie, Marblehead, MA (US); Steven W. Ek, Bolton, MA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 13/757,440

(22) Filed: Feb. 1, 2013

(65) Prior Publication Data

US 2013/0144314 A1 Jun. 6, 2013

Related U.S. Application Data

(60) Continuation of application No. 13/242,499, filed on Sep. 23, 2011, now Pat. No. 8,366,744, which is a
(Continued)

(51) Int. Cl.
*A61B 17/04* (2006.01)
*A61B 17/06* (2006.01)
(Continued)

(52) U.S. Cl.
CPC ....... *A61B 17/0469* (2013.01); *A61B 17/0401* (2013.01); *A61B 17/0467* (2013.01);
(Continued)

(58) Field of Classification Search
CPC . A61B 17/04; A61B 17/0401; A61B 17/0469; A61B 2017/0475
(Continued)

(56) References Cited

U.S. PATENT DOCUMENTS 233,475 A 10/1880 Cook et al.
261,501 A 7/1882 Vandermark
(Continued)

FOREIGN PATENT DOCUMENTS

EP 0 108 912 5/1984
EP 0 315 371 5/1989
(Continued)

OTHER PUBLICATIONS

Annex to Form PCT/ISA/206 Communication Relating to the Results of the Partial International Search (6 pgs), Jul. 30, 2004.
(Continued)

*Primary Examiner* — Kathleen Holwerda
(74) *Attorney, Agent, or Firm* — Burns & Levinson LLP; Joseph M. Maraia

(57) ABSTRACT

An apparatus for tissue repair, comprising first and second fixation members, a flexible coupling member coupling the first and second fixation members, the flexible coupling member having two terminal ends, one of the two terminal ends terminating adjacent one of the first and second fixation members, the flexible coupling member slidably coupled to at least one of the first and second fixation members such that when the other of the two terminal ends of the flexible coupling member is pulled, a length of the flexible coupling member between the first and second fixation members is shortened, and a Chinese trap formed in the flexible coupling member through which a portion of the flexible coupling member slides when the flexible coupling member is pulled.

10 Claims, 75 Drawing Sheets

Related U.S. Application Data division of application No. 12/684,722, filed on Jan. 8, 2010, which is a continuation of application No. 10/918,455, filed on Aug. 16, 2004, now Pat. No. 7,651,509, which is a continuation of application No. 10/278,474, filed on Oct. 23, 2002, now Pat. No. 7,887,551, which is a continuation-in-part of application No. 09/886,367, filed on Jun. 22, 2001, now abandoned, which is a continuation of application No. 09/704,926, filed on Nov. 2, 2000, now Pat. No. 7,153,312, and a continuation-in-part of application No. 09/453,120, filed on Dec. 2, 1999, now abandoned.

(51) Int. Cl.
*A61F 2/08* (2006.01)
*A61B 17/064* (2006.01)

(52) U.S. Cl.
CPC .. *A61B 17/06066* (2013.01); *A61B 17/06109* (2013.01); *A61B 17/06166* (2013.01); *A61F 2/0805* (2013.01); *A61F 2/0811* (2013.01); *A61B 17/0487* (2013.01); *A61B 2017/044* (2013.01); *A61B 2017/0404* (2013.01); *A61B 2017/0409* (2013.01); *A61B 2017/0412* (2013.01); *A61B 2017/0414* (2013.01); *A61B 2017/0417* (2013.01); *A61B 2017/0427* (2013.01); *A61B 2017/0437* (2013.01); *A61B 2017/0445* (2013.01); *A61B 2017/0458* (2013.01); *A61B 2017/0464* (2013.01); *A61B 2017/0475* (2013.01); *A61B 2017/0477* (2013.01); *A61B 2017/0496* (2013.01); *A61B 2017/061* (2013.01); *A61B 2017/0646* (2013.01); *A61B 2017/0647* (2013.01); *A61B 2017/0648* (2013.01); *A61F 2002/0829* (2013.01); *A61F 2002/0852* (2013.01); *A61F 2002/0858* (2013.01); *A61F 2002/0882* (2013.01); *A61F 2002/0888* (2013.01)

(58) Field of Classification Search
USPC ........ 606/139, 144–148, 153–156, 224, 225, 606/228–232
See application file for complete search history.

(56) References Cited

U.S. PATENT DOCUMENTS

| | | | |
|---|---|---|---|
| 1,635,066 A | 7/1927 | Wells |
| 2,479,464 A | 8/1949 | Bliss |
| 2,610,631 A | 9/1952 | Calicchio |
| 2,880,728 A | 4/1959 | Rights |
| 2,881,762 A | 4/1959 | Lowrie |
| 3,409,014 A | 11/1968 | Grant |
| 3,470,875 A | 10/1969 | Johnson |
| 3,618,447 A | 11/1971 | Goins |
| 3,664,345 A | 5/1972 | Dabbs et al. |
| 3,716,058 A | 2/1973 | Tanner, Jr. |
| 3,752,516 A | 8/1973 | Mumma |
| 3,752,519 A | 8/1973 | Nordell et al. |
| 3,757,629 A | 9/1973 | Schneider |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,867,944 A | 2/1975 | Samuels |
| 3,871,379 A | 3/1975 | Clarke |
| 3,910,281 A | 10/1975 | Kletschka et al. |
| 3,946,740 A | 3/1976 | Bassett |
| 3,976,079 A | 8/1976 | Samuels et al. |
| 3,977,050 A | 8/1976 | Perez |
| 3,985,138 A | 10/1976 | Jarvik |
| 4,006,747 A | 2/1977 | Kronenthal et al. |
| 4,039,753 A | 8/1977 | Balogh et al. |
| 4,141,087 A | 2/1979 | Shalaby et al. |
| 4,144,876 A | 3/1979 | DeLeo |
| 4,160,453 A | 7/1979 | Miller |
| 4,185,514 A | 1/1980 | Edwards |
| 4,186,514 A | 2/1980 | Oquita |
| 4,235,238 A | 11/1980 | Ogiu et al. |
| 4,316,469 A | 2/1982 | Kapitanov |
| 4,326,531 A | 4/1982 | Shimonaka |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,570,623 A | 2/1986 | Ellison et al. |
| 4,595,007 A | 6/1986 | Mericle |
| 4,596,249 A | 6/1986 | Freda et al. |
| 4,602,635 A | 7/1986 | Mulhollan et al. |
| 4,616,650 A | 10/1986 | Green et al. |
| 4,624,254 A | 11/1986 | McGarry et al. |
| 4,635,637 A | 1/1987 | Schreiber |
| 4,636,121 A | 1/1987 | Miller |
| 4,641,652 A | 2/1987 | Hutterer et al. |
| 4,662,068 A | 5/1987 | Polonsky |
| 4,705,040 A | 11/1987 | Mueller et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,741,330 A | 5/1988 | Hayhurst |
| 4,741,336 A | 5/1988 | Failla et al. |
| 4,750,492 A | 6/1988 | Jacobs |
| 4,760,848 A | 8/1988 | Hasson |
| 4,781,190 A | 11/1988 | Lee |
| 4,809,695 A | 3/1989 | Gwathmey et al. |
| 4,823,794 A | 4/1989 | Pierce |
| 4,841,960 A | 6/1989 | Garner |
| 4,846,793 A | 7/1989 | Leonard et al. |
| 4,858,608 A | 8/1989 | McQuilkin |
| 4,873,976 A | 10/1989 | Schreiber |
| 4,884,572 A | 12/1989 | Bays et al. |
| 4,887,601 A | 12/1989 | Richards |
| 4,890,615 A | 1/1990 | Caspari et al. |
| 4,895,148 A | 1/1990 | Bays et al. |
| 4,899,743 A | 2/1990 | Nicholson et al. |
| 4,917,699 A | 4/1990 | Chervitz |
| 4,923,461 A | 5/1990 | Caspari et al. |
| 4,950,285 A | 8/1990 | Wilk |
| 4,961,741 A | 10/1990 | Hayhurst |
| 4,983,176 A | 1/1991 | Cushman et al. |
| 4,994,028 A | 2/1991 | Leonard et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,201 A | 10/1991 | Asnis |
| 5,078,731 A | 1/1992 | Hayhurst |
| 5,084,050 A | 1/1992 | Draenert |
| 5,084,058 A | 1/1992 | Li |
| 5,087,263 A | 2/1992 | Li |
| 5,100,415 A | 3/1992 | Hayhurst |
| 5,102,421 A | 4/1992 | Anspach, Jr. |
| 5,123,913 A | 6/1992 | Wilk et al. |
| 5,141,520 A | 8/1992 | Gobe et al. |
| 5,149,329 A | 9/1992 | Richardson |
| 5,154,189 A | 10/1992 | Oberlander |
| D331,626 S | 12/1992 | Hayhurst et al. |
| 5,176,691 A | 1/1993 | Pierce |
| 5,178,629 A | 1/1993 | Kammerer |
| 5,203,787 A | 4/1993 | Noblitt et al. |
| 5,207,753 A | 5/1993 | Badrinath |
| 5,211,650 A | 5/1993 | Noda |
| 5,217,470 A | 6/1993 | Weston |
| 5,219,359 A | 6/1993 | McQuilkin et al. |
| 5,224,946 A | 7/1993 | Hayhurst et al. |
| 5,236,445 A | 8/1993 | Hayhurst et al. |
| 5,246,441 A | 9/1993 | Ross et al. |
| 5,258,015 A | 11/1993 | Li et al. |
| 5,258,016 A | 11/1993 | DiPoto et al. |

(56) References Cited

U.S. PATENT DOCUMENTS

| | | |
|---|---|---|
| 5,261,914 A | 11/1993 | Warren |
| 5,268,001 A | 12/1993 | Nicholson et al. |
| 5,269,809 A | 12/1993 | Hayhurst et al. |
| 5,279,539 A | 1/1994 | Bohan |
| 5,282,809 A | 2/1994 | Kammerer et al. |
| 5,318,577 A | 6/1994 | Li |
| 5,320,633 A * | 6/1994 | Allen et al. .......... 606/144 |
| 5,330,491 A | 7/1994 | Walker et al. |
| 5,336,229 A | 8/1994 | Noda |
| 5,336,231 A | 8/1994 | Adair |
| 5,342,369 A | 8/1994 | Harryman, II |
| 5,354,299 A | 10/1994 | Coleman |
| 5,364,408 A | 11/1994 | Gordon |
| 5,366,480 A | 11/1994 | Corriveau |
| 5,417,691 A | 5/1995 | Hayhurst |
| 5,417,692 A | 5/1995 | Goble et al. |
| 5,437,680 A | 8/1995 | Yoon |
| 5,439,684 A | 8/1995 | Prewett et al. |
| 5,441,502 A | 8/1995 | Bartlett |
| 5,447,512 A | 9/1995 | Wilson et al. |
| 5,458,081 A | 10/1995 | Reichert |
| 5,458,608 A | 10/1995 | Wortrich |
| 5,467,786 A | 11/1995 | Allen et al. |
| 5,474,572 A | 12/1995 | Hayhurst |
| 5,490,750 A | 2/1996 | Gundy |
| 5,496,331 A | 3/1996 | Xu et al. |
| 5,500,000 A | 3/1996 | Feagin et al. |
| 5,520,696 A | 5/1996 | Wenstrom, Jr. |
| 5,520,700 A | 5/1996 | Beyar et al. |
| 5,520,921 A | 5/1996 | Chalifoux |
| 5,522,820 A | 6/1996 | Caspari et al. |
| 5,522,844 A | 6/1996 | Johnson |
| 5,527,341 A | 6/1996 | Gogolewski |
| 5,527,342 A | 6/1996 | Pietrzak et al. |
| 5,545,178 A | 8/1996 | Kensey et al. |
| 5,554,171 A | 9/1996 | Gatturna et al. |
| 5,562,684 A | 10/1996 | Kammerer |
| 5,569,306 A | 10/1996 | Thal |
| 5,573,286 A | 11/1996 | Rogozinski |
| 5,593,424 A | 1/1997 | Northrup, III |
| 5,601,557 A | 2/1997 | Hayhurst |
| 5,601,558 A | 2/1997 | Torrie et al. |
| 5,607,432 A | 3/1997 | Fucci |
| 5,609,597 A | 3/1997 | Lehrer |
| 5,641,256 A | 6/1997 | Gundy |
| 5,643,319 A | 7/1997 | Green et al. |
| 5,643,321 A | 7/1997 | McDevitt |
| 5,647,874 A | 7/1997 | Hayhurst |
| 5,658,299 A | 8/1997 | Hart |
| 5,665,112 A | 9/1997 | Thal |
| 5,690,676 A | 11/1997 | DiPoto et al. |
| 5,690,678 A | 11/1997 | Johnson |
| 5,702,422 A | 12/1997 | Stone |
| 5,702,462 A | 12/1997 | Oberlander |
| 5,713,904 A | 2/1998 | Errico et al. |
| 5,716,359 A | 2/1998 | Ojima et al. |
| 5,720,753 A | 2/1998 | Sander et al. |
| 5,720,765 A | 2/1998 | Thal |
| 5,725,529 A | 3/1998 | Nicholson et al. |
| 5,725,556 A | 3/1998 | Moser et al. |
| 5,725,581 A | 3/1998 | Branemark |
| 5,728,109 A | 3/1998 | Schulze et al. |
| 5,728,136 A | 3/1998 | Thal |
| 5,730,744 A | 3/1998 | Justin et al. |
| 5,746,754 A | 5/1998 | Chan |
| 5,749,898 A | 5/1998 | Schulze et al. |
| 5,782,862 A | 7/1998 | Bonutti |
| 5,782,864 A | 7/1998 | Lizardi |
| 5,797,928 A | 8/1998 | Kogasaka |
| 5,810,848 A | 9/1998 | Hayhurst |
| 5,814,069 A | 9/1998 | Schulze et al. |
| RE36,020 E | 12/1998 | Moore et al. |
| 5,843,084 A | 12/1998 | Hart et al. |
| 5,843,087 A | 12/1998 | Jensen et al. |
| 5,846,254 A | 12/1998 | Schulze et al. |
| 5,860,983 A | 1/1999 | Wenstrom, Jr. |
| 5,871,490 A | 2/1999 | Schulze et al. |
| 5,891,168 A | 4/1999 | Thal |
| 5,893,592 A | 4/1999 | Schulze et al. |
| 5,893,856 A | 4/1999 | Jacob et al. |
| 5,893,880 A | 4/1999 | Egan et al. |
| 5,895,395 A | 4/1999 | Yeung |
| 5,897,564 A | 4/1999 | Schulze et al. |
| 5,902,321 A | 5/1999 | Caspari et al. |
| 5,921,986 A | 7/1999 | Bonutti |
| 5,928,244 A | 7/1999 | Tovey et al. |
| 5,941,439 A | 8/1999 | Kammerer et al. |
| 5,948,002 A | 9/1999 | Bonutti |
| 5,954,747 A | 9/1999 | Clark |
| 5,964,765 A | 10/1999 | Fenton, Jr. et al. |
| 5,964,783 A * | 10/1999 | Grafton et al. .......... 606/232 |
| 5,976,127 A | 11/1999 | Lax |
| 5,980,524 A | 11/1999 | Justin et al. |
| 5,989,252 A | 11/1999 | Fumex |
| 5,993,458 A | 11/1999 | Vaitekunas et al. |
| 6,024,758 A | 2/2000 | Thal |
| 6,027,523 A | 2/2000 | Schmieding |
| 6,039,753 A | 3/2000 | Meislin |
| 6,045,574 A | 4/2000 | Thal |
| 6,056,320 A | 5/2000 | Khalifa et al. |
| 6,063,106 A | 5/2000 | Gibson |
| 6,066,106 A | 5/2000 | Sherman et al. |
| 6,074,395 A | 6/2000 | Trott et al. |
| 6,096,038 A | 8/2000 | Michelson |
| 6,096,060 A | 8/2000 | Fitts et al. |
| 6,117,160 A | 9/2000 | Bonutti |
| 6,143,017 A | 11/2000 | Thal |
| 6,146,387 A | 11/2000 | Trott et al. |
| 6,152,934 A | 11/2000 | Harper et al. |
| 6,152,936 A | 11/2000 | Christy et al. |
| 6,156,039 A | 12/2000 | Thal |
| 6,165,203 A | 12/2000 | Krebs |
| 6,174,324 B1 | 1/2001 | Egan et al. |
| 6,193,754 B1 | 2/2001 | Seedhom |
| 6,217,591 B1 | 4/2001 | Egan et al. |
| 6,283,996 B1 | 9/2001 | Chervitz et al. |
| 6,286,746 B1 | 9/2001 | Egan et al. |
| 6,293,961 B2 * | 9/2001 | Schwartz et al. .......... 606/232 |
| 6,296,659 B1 * | 10/2001 | Foerster .......... 606/224 |
| 6,306,158 B1 | 10/2001 | Bartlett |
| 6,306,159 B1 * | 10/2001 | Schwartz et al. .......... 606/232 |
| 6,319,263 B1 | 11/2001 | Levinson |
| 6,319,271 B1 | 11/2001 | Schwartz et al. |
| 6,358,271 B1 | 3/2002 | Egan et al. |
| 6,409,743 B1 | 6/2002 | Fenton, Jr. |
| 6,432,123 B2 | 8/2002 | Schwartz et al. |
| 6,491,707 B2 | 12/2002 | Makower et al. |
| 6,500,184 B1 | 12/2002 | Chan et al. |
| 6,520,980 B1 | 2/2003 | Foerster |
| 6,524,317 B1 | 2/2003 | Ritchart et al. |
| 6,527,795 B1 | 3/2003 | Lizardi |
| 6,533,802 B2 | 3/2003 | Bojarski et al. |
| 6,554,852 B1 | 4/2003 | Oberlander |
| 6,585,730 B1 | 7/2003 | Foerster |
| 6,635,073 B2 | 10/2003 | Bonutti |
| 6,641,596 B1 | 11/2003 | Lizardi |
| 6,652,563 B2 | 11/2003 | Dreyfuss |
| 6,656,182 B1 | 12/2003 | Hayhurst |
| 6,669,705 B2 | 12/2003 | Westhaver et al. |
| 6,692,499 B2 | 2/2004 | Tormalaet et al. |
| 6,692,516 B2 | 2/2004 | West, Jr. et al. |
| 6,770,076 B2 | 8/2004 | Foerster |
| 6,855,157 B2 | 2/2005 | Foerster et al. |
| 6,923,824 B2 | 8/2005 | Morgan et al. |
| 6,972,019 B2 | 12/2005 | Michelson |
| 6,972,027 B2 | 12/2005 | Fallin et al. |
| 7,153,312 B2 | 12/2006 | Torrie et al. |
| 7,163,563 B2 | 1/2007 | Schwartz et al. |
| 7,500,983 B1 | 3/2009 | Kaiser et al. |
| 2001/0010005 A1 | 7/2001 | Kammerer et al. |
| 2002/0019649 A1 | 2/2002 | Sikora et al. |
| 2002/0052629 A1 | 5/2002 | Morgan et al. |
| 2002/0091959 A1 | 7/2002 | Klein et al. |
| 2002/0095181 A1 | 7/2002 | Beyar |

(56) References Cited

U.S. PATENT DOCUMENTS

| | | |
|---|---|---|
| 2002/0133159 A1 | 9/2002 | Jackson |
| 2002/0147463 A1 | 10/2002 | Martinek |
| 2002/0156500 A1 | 10/2002 | Storz-Irion et al. |
| 2002/0165548 A1 | 11/2002 | Jutley |
| 2002/0173821 A1 | 11/2002 | Fenton et al. |
| 2003/0070004 A1 | 4/2003 | Mukundan et al. |
| 2003/0109900 A1 | 6/2003 | Martinek |
| 2003/0120277 A1 | 6/2003 | Berger |
| 2003/0130694 A1 | 7/2003 | Bojarski et al. |
| 2003/0236555 A1 | 12/2003 | Thornes |
| 2004/0002734 A1 | 1/2004 | Fallin et al. |
| 2004/0037094 A1 | 2/2004 | Muegge et al. |
| 2004/0092937 A1 | 5/2004 | Criscuolo et al. |
| 2004/0133238 A1 | 7/2004 | Cerier |
| 2004/0133239 A1 | 7/2004 | Singhatat |
| 2004/0138683 A1 | 7/2004 | Shelton et al. |
| 2004/0243131 A1 | 12/2004 | Dirks et al. |
| 2004/0267317 A1 | 12/2004 | Higgins et al. |
| 2005/0033363 A1 | 2/2005 | Bojarski et al. |
| 2005/0037150 A1 | 2/2005 | Iijima et al. |
| 2005/0187577 A1 | 8/2005 | Selvitelli et al. |
| 2005/0277961 A1 | 12/2005 | Stone et al. |
| 2005/0277986 A1 | 12/2005 | Foerster et al. |
| 2006/0190042 A1 | 8/2006 | Stone et al. |
| 2007/0083236 A1 | 4/2007 | Sikora et al. |
| 2008/0065114 A1 | 3/2008 | Stone et al. |
| 2008/0082128 A1 | 4/2008 | Stone |

FOREIGN PATENT DOCUMENTS

| | | |
|---|---|---|
| EP | 0 598 219 | 5/1994 |
| EP | 0 632 999 | 1/1995 |
| EP | 0 260 970 | 7/1995 |
| EP | 0 913 123 | 5/1999 |
| EP | 1 013 229 | 6/2000 |
| EP | 0 847 727 | 2/2004 |
| EP | 1 444 959 | 8/2004 |
| EP | 1 568 326 | 10/2007 |
| FR | 2 422 386 | 4/1978 |
| FR | 2731610 | 9/1996 |
| JP | 54-166092 | 11/1979 |
| JP | 54-166093 | 11/1979 |
| JP | 54-176284 | 12/1979 |
| JP | 54-178988 | 12/1979 |
| WO | WO 98/22047 | 5/1998 |
| WO | WO 98/51241 | 11/1998 |
| WO | WO 99/01084 | 1/1999 |
| WO | WO 99/12480 | 3/1999 |
| WO | WO 00/40159 | 7/2000 |
| WO | WO 01/39671 | 6/2001 |
| WO | WO 02/12480 | 2/2002 |
| WO | WO 02/36020 | 5/2002 |
| WO | WO 02/091959 | 11/2002 |
| WO | WO 03/001893 | 1/2003 |
| WO | WO 2004/037094 | 5/2004 |
| WO | WO 2005/037150 | 4/2005 |

OTHER PUBLICATIONS

Office Action from European Serial No. 01981796.4 mailed Apr. 21, 2005.
Office Action U.S. Appl. No. 10/278,474 dated Dec. 29, 2008, 9 pages.
Office Action U.S. Appl. No. 10/278,474 dated Jan. 22, 2008, 9 pages.
Office Action U.S. Appl. No. 11/165,551 dated Feb. 25, 2008, 15 pages.
Office Action U.S. Appl. No. 11/165,551 dated Oct. 28, 2008, 13 pages.
Office Action U.S. Appl. No. 11/535,868 dated May 23, 2008, 14 pages.
Office Action U.S. Appl. No. 11/535,868 dated Nov. 12, 2008, 18 pages.
Office Action dated Apr. 4, 2007 in U.S. Appl. No. 10/358,252, 6 pages.
Office Action dated Aug. 30, 2007 in U.S. Appl. No. 10/278,474, 10 pages.
Office Action dated Dec. 2, 2008 in U.S. Appl. No. 10/358,252, 7 pages.
Office Action dated Feb. 8, 2006 in U.S. Appl. No. 10/358,252, 6 pages.
Office Action dated Jan. 22, 2008 in U.S. Appl. No. 10/278,474, 10 pages.
Office Action dated Jun. 4, 2007 in U.S. Appl. No. 10/358,252, 6 pages.
Office Action dated Mar. 30, 2007 in U.S. Appl. No. 10/278,474, 21 pages.
Office Action dated May 14, 2008 in U.S. Appl. No. 10/358,252, 8 pages.
Office Action dated Nov. 20, 2007 in U.S. Appl. No. 10/358,252, 7 pages.
Office Action dated Oct. 13, 2006 in U.S. Appl. No. 10/358,252, 7 pages.
Office Action dated Oct. 5, 2005 in U.S. Appl. No. 10/358,252, 7 pages.
Office Action dated Mar. 24, 2010 in U.S. Appl. No. 11/535,868, 14 pages.
PCT/US2004/003258 Annex to Form PCT/ISA/206 Communication Relating to the Results of the Partial International Search, mailed Jul. 30, 2004, 6 pages.
PCT/US2004/003528 International Search Report, mailed Oct. 21, 2004, 10 pages.
PCT/US2006/024752 International Preliminary Report on Patentability, dated Jan. 10, 2008.
PCT/US2006/024752 International Search Report and Written Opinion, dated Nov. 7, 2006.
PCT/US2007/076348 International Search Report and Written Opinion, dated Jun. 20, 2008.
Sotereanos, D. G. "Rotator Cuff Repair Using PANALOK RC Absorbable Anchor," undated.
Thal, R. "A Knotless Suture Anchor & Method for Arthroscopic Bankart Repair Introduction," Poster Board No. 296 at the 1999 Annual Meeting of the American Academy of Orthopaedic Surgeons.
Thal, R. "A Knotless Suture Anchor: Technique for Use in Arthroscopic Bankart Repair," undated.
Uniecom Surgical Sutures & Suture Needles, "Suture Needles Information", 2005.
Notice of Reasons for Rejection for Japanese Application No. 2008-518488, mailed Jul. 10, 2012.
Notice of Reasons for Rejection for Japanese Application No. 2009-530498, mailed Jun. 19, 2012.
Office Action issued in U.S. Appl. No. 10/358,252, dated May 28, 2009.
Office Action issued in U.S. Appl. No. 10/358,252, dated Dec. 24, 2009.
Office Action issued in U.S. Appl. No. 10/358,252, dated Feb. 15, 2011.
Office Action issued in U.S. Appl. No. 10/358,252, dated Oct. 18, 2011.
Office Action issued in U.S. Appl. No. 10/918,445, dated Oct. 12, 2006.
Office Action issued in U.S. Appl. No. 10/918,445, dated Dec. 28, 2007.
Office Action issued in U.S. Appl. No. 10/918,445, dated Jul. 24, 2008.
Office Action issued in U.S. Appl. No. 10/918,445, dated Jun. 27, 2007.
Office Action issued in U.S. Appl. No. 10/918,445, dated Mar. 31, 2009.
Office Action issued in U.S. Appl. No. 10/918,445, dated Mar. 6, 2007.
Office Action issued in U.S. Appl. No. 10/918,445, dated May 25, 2006.
Office Action issued in U.S. Appl. No. 11/165,551, dated Feb. 25, 2008.

(56) References Cited

OTHER PUBLICATIONS

Office Action issued in U.S. Appl. No. 11/165,551, dated Jun. 2, 2009.
Office Action issued in U.S. Appl. No. 11/535,868, dated May 22, 2009.
Office Action issued in U.S. Appl. No. 11/535,868, dated Mar. 14, 2011.
Office Action issued in U.S. Appl. No. 11/535,868, dated Mar. 24, 2010.
Office Action issued in U.S. Appl. No. 12/684,722, dated Oct. 20, 2011, 8 pages.
Office Action issued in U.S. Appl. No. 12/684,722, dated Feb. 7, 2012.
Office Action issued in U.S. Appl. No. 12/684,752, dated Jan. 25, 2012.
Communication Pursuant to Article 94(3) EPC for European Application 04708599.8, dated Feb. 18, 2008.
Communication Pursuant to Article 94(3) EPC for European Application 04708599.8, dated Apr. 30, 2009.
Communication Pursuant to Article 94(3) EPC for European Application 04708599.8, dated Feb. 28, 2011.
Notice of Reasons of Rejection for Japanese Application No. 2008-518488, mailed Feb. 7, 2012.

\* cited by examiner

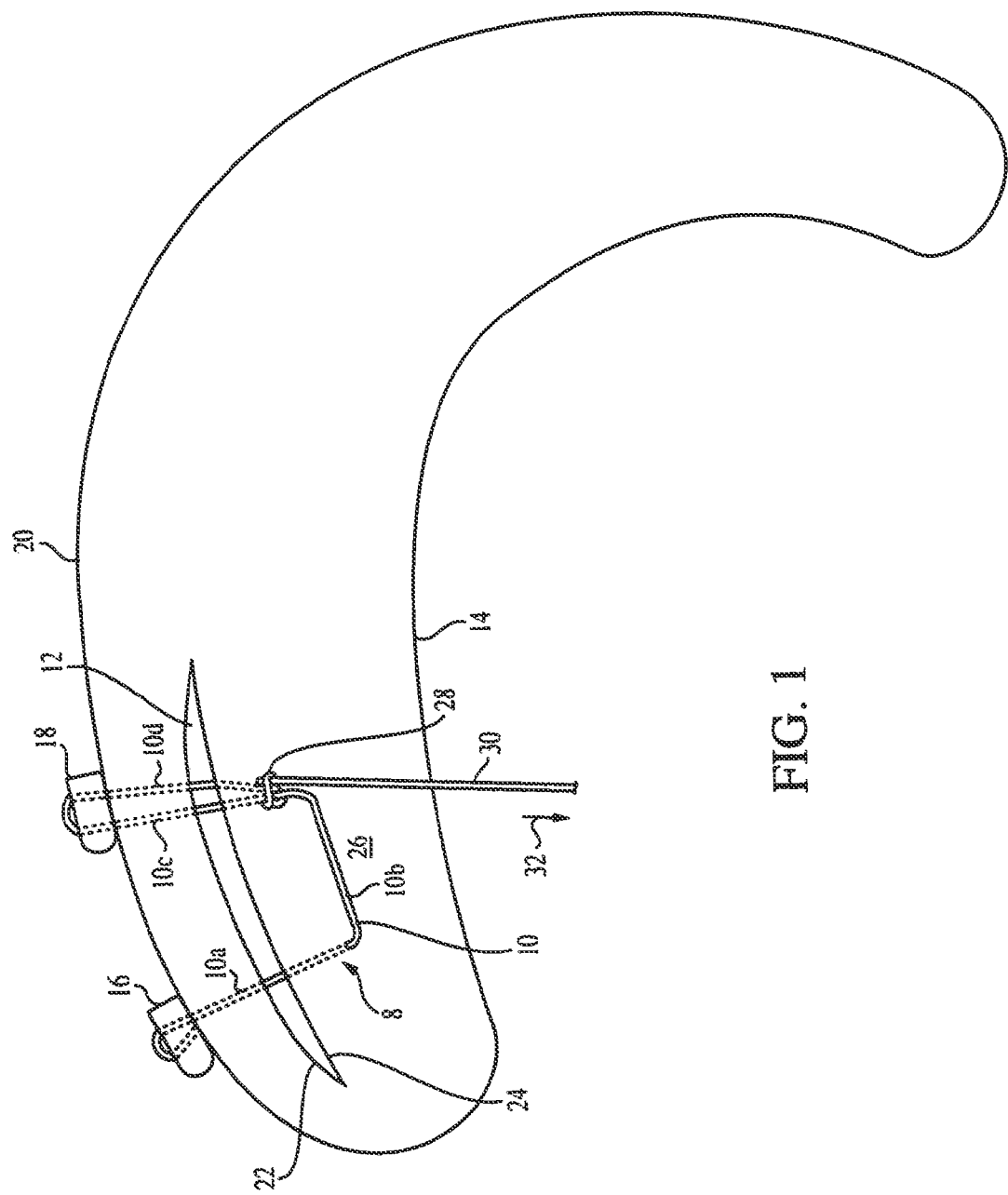

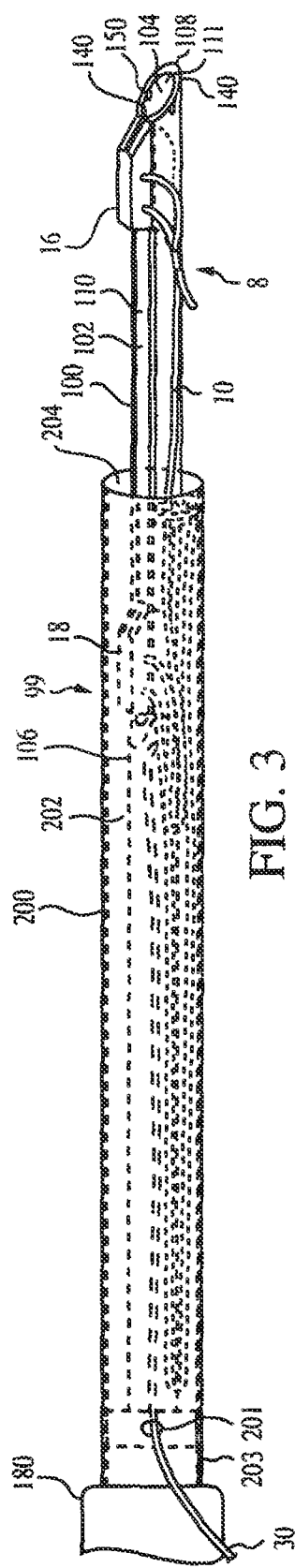
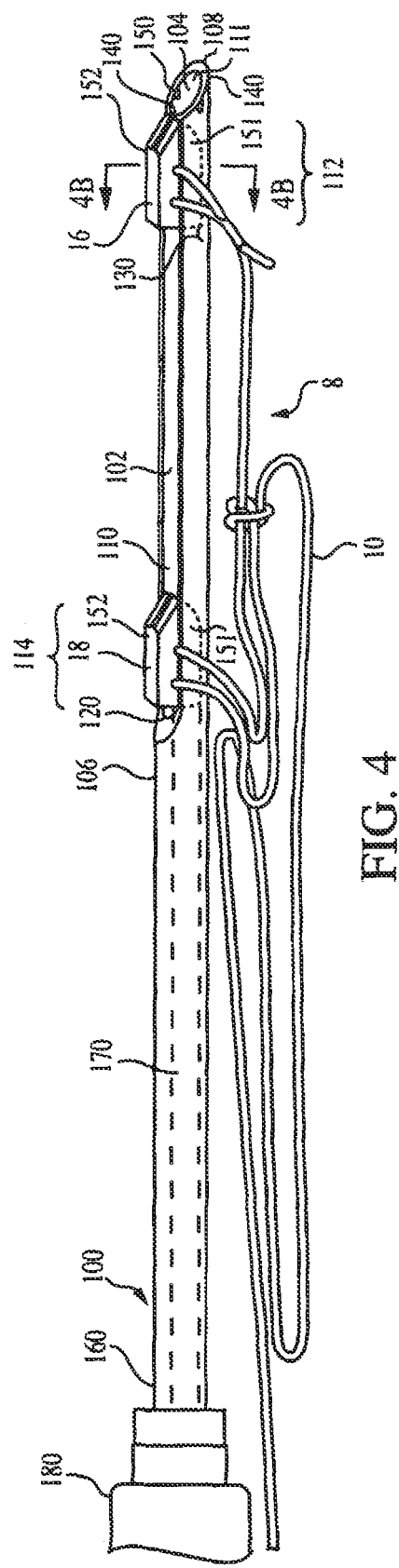

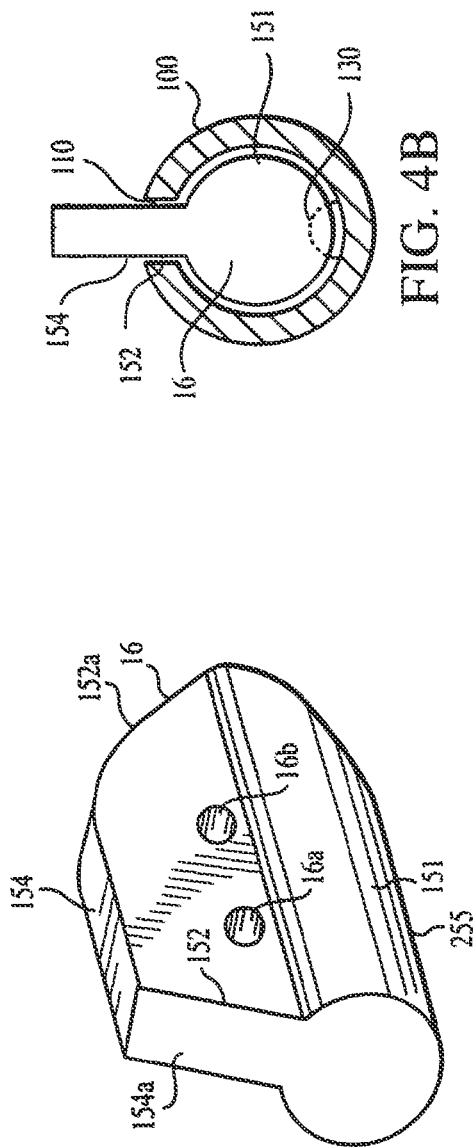
FIG. 4A
FIG. 4B
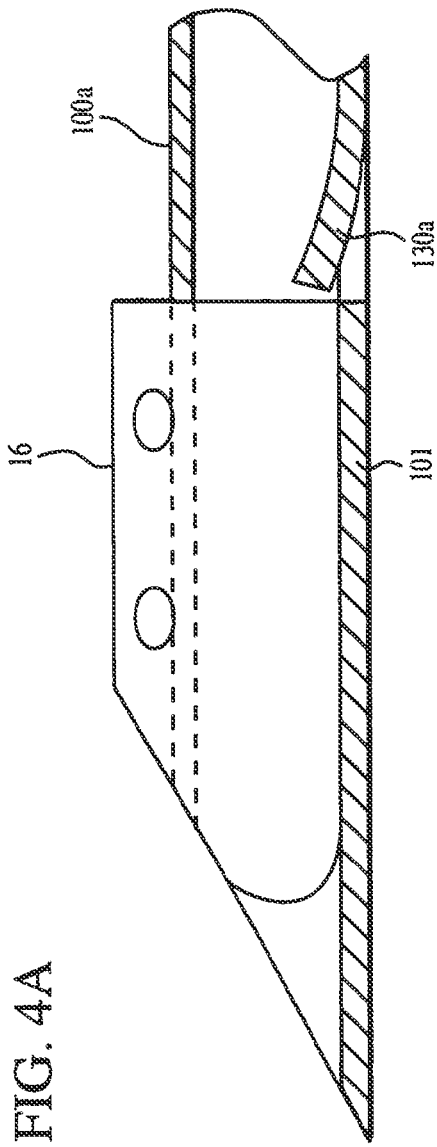
FIG. 4C

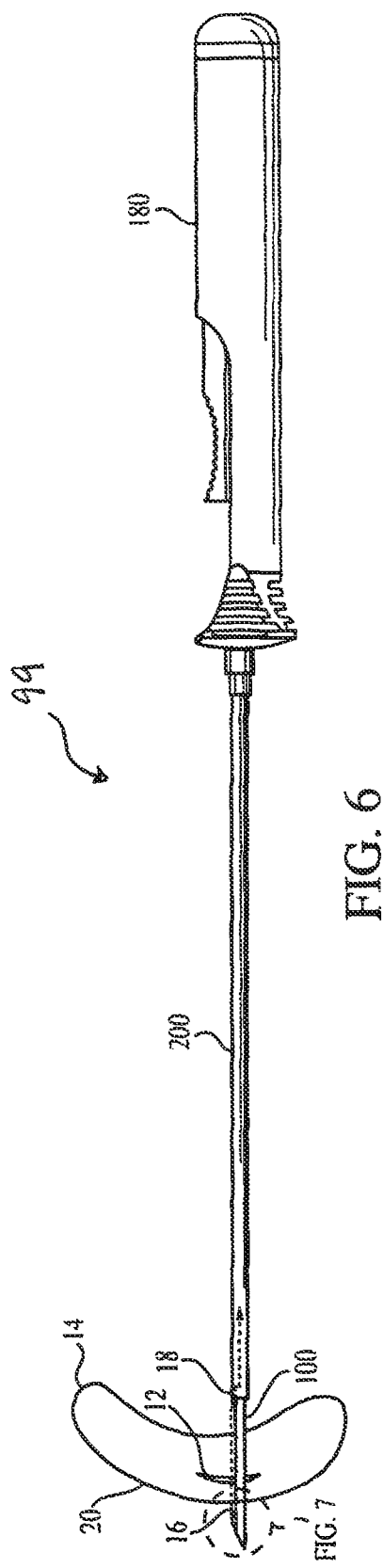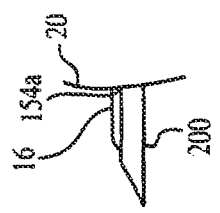

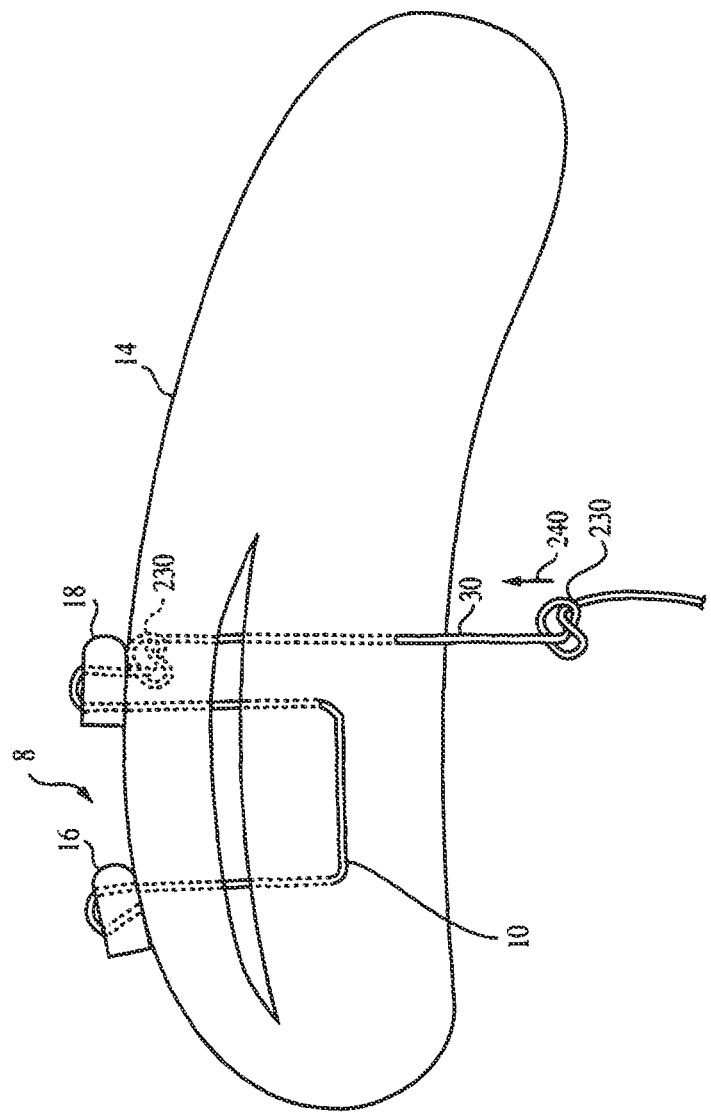

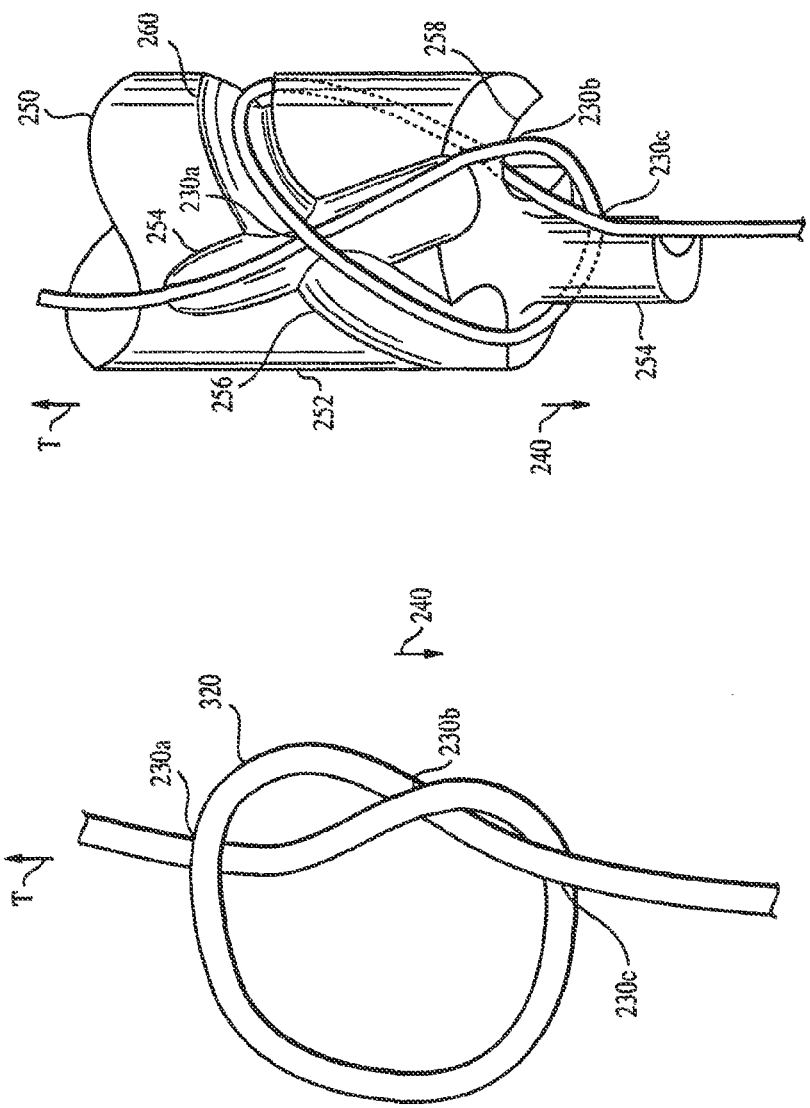

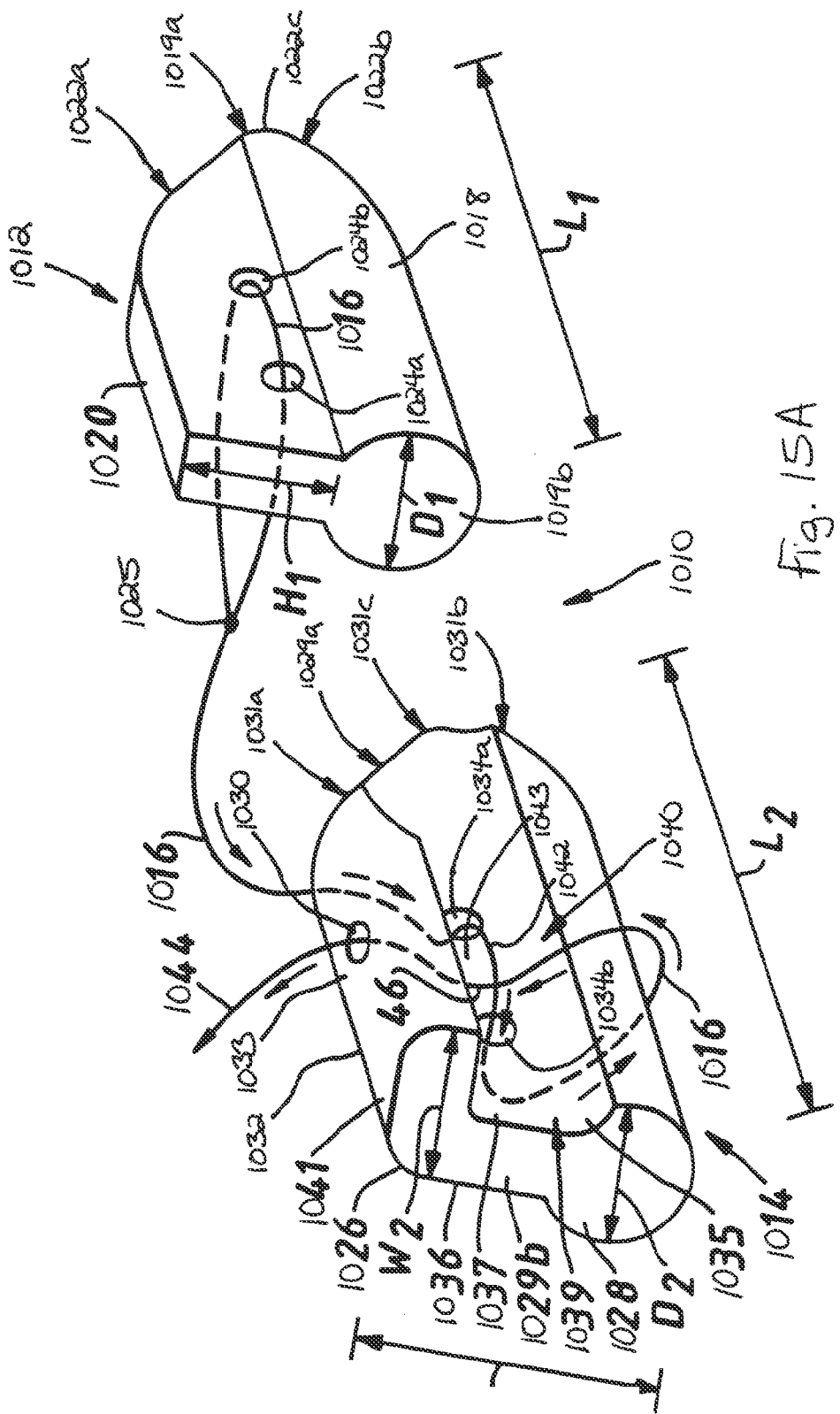

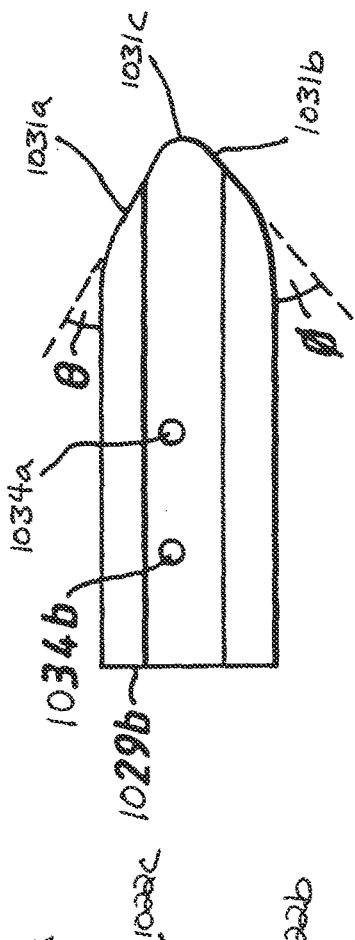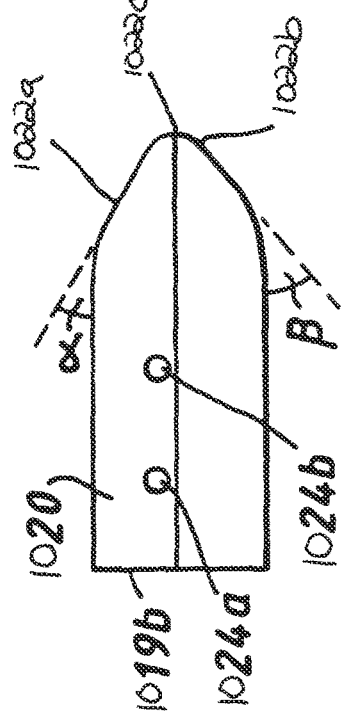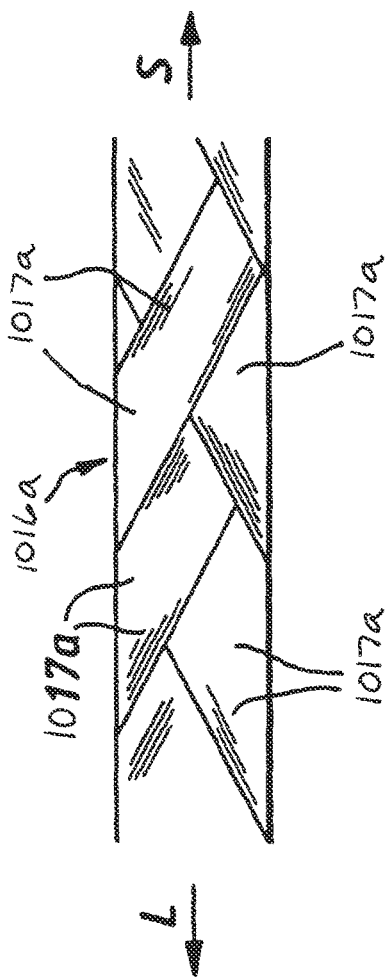
Fig. 15B
Fig. 15C
Fig. 15D

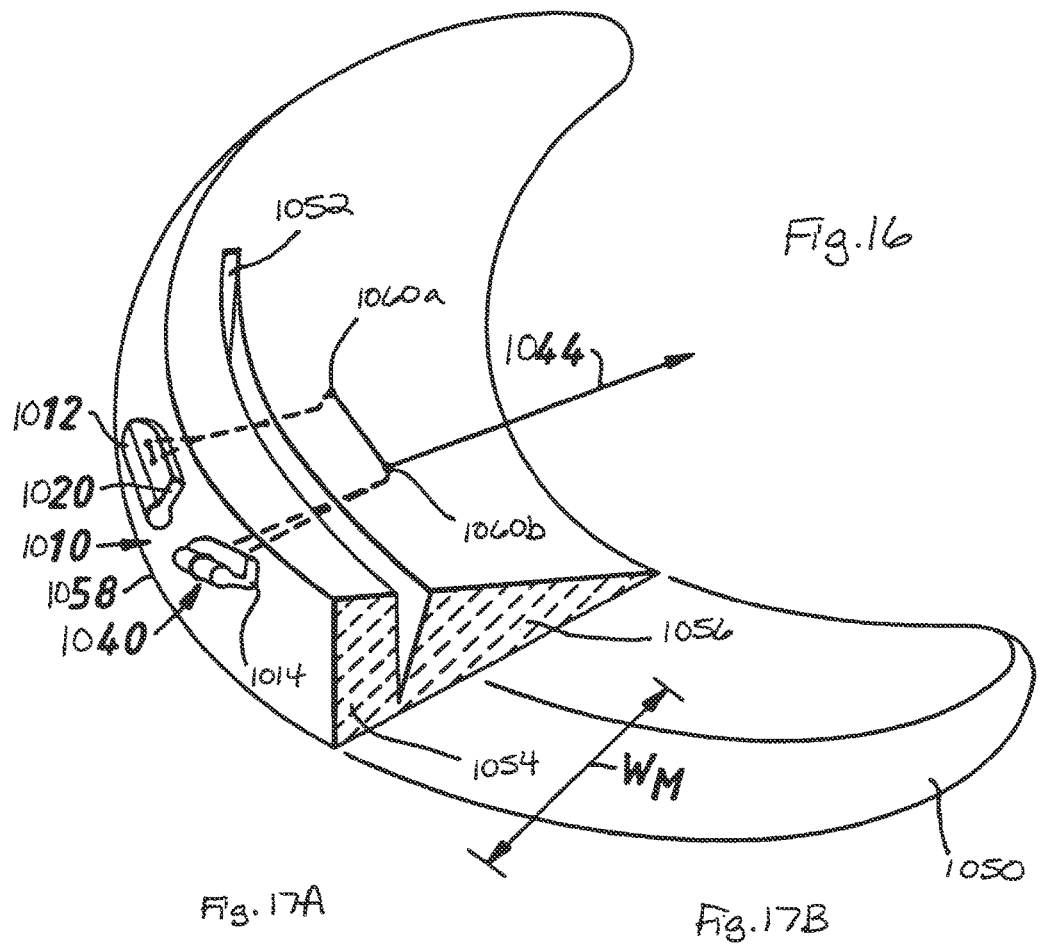
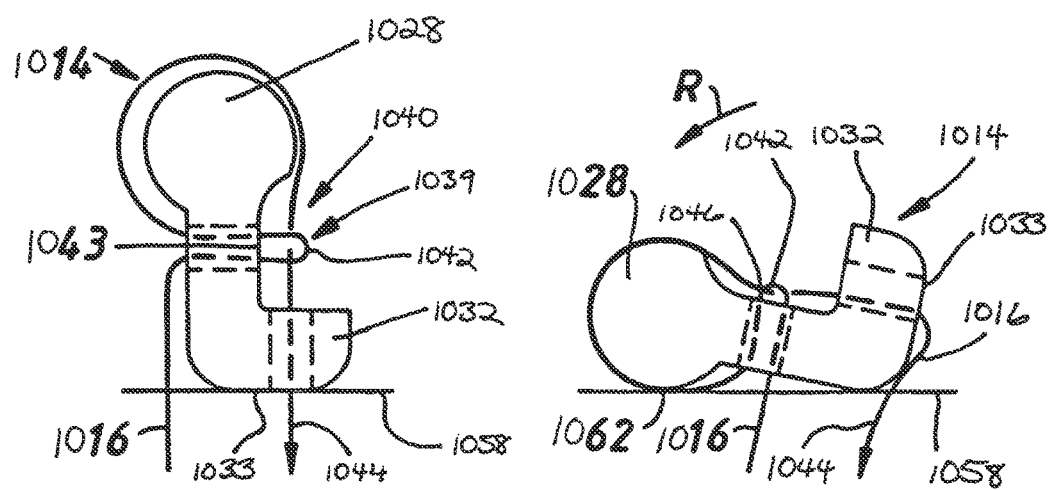

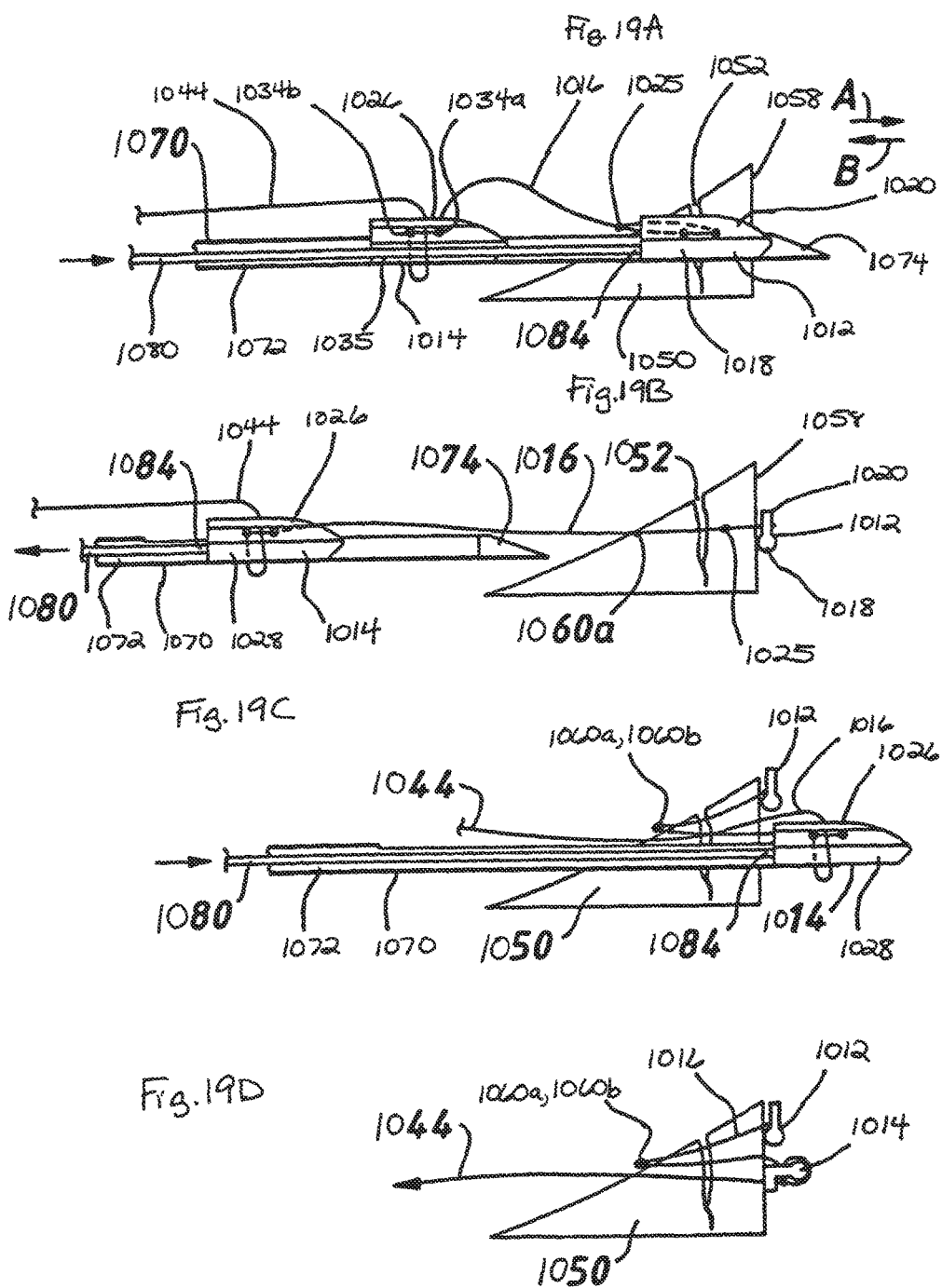

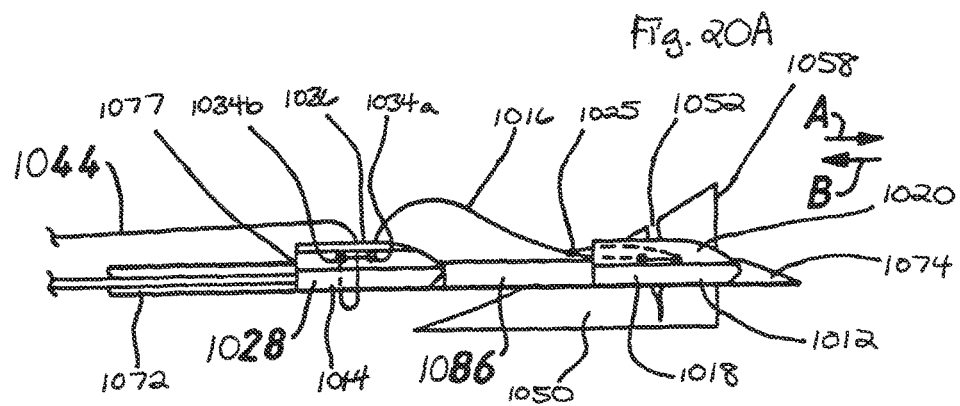
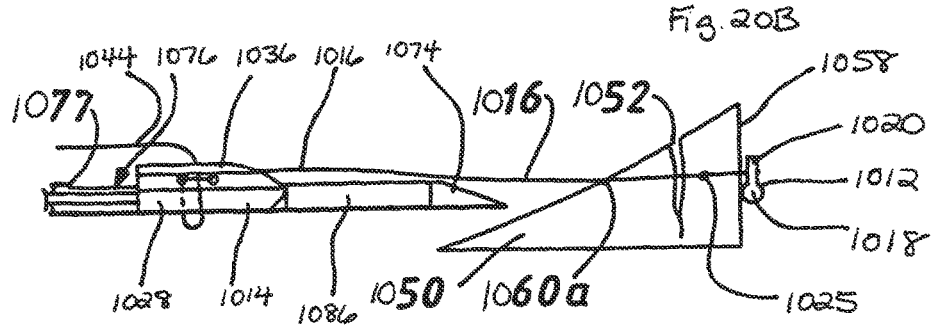
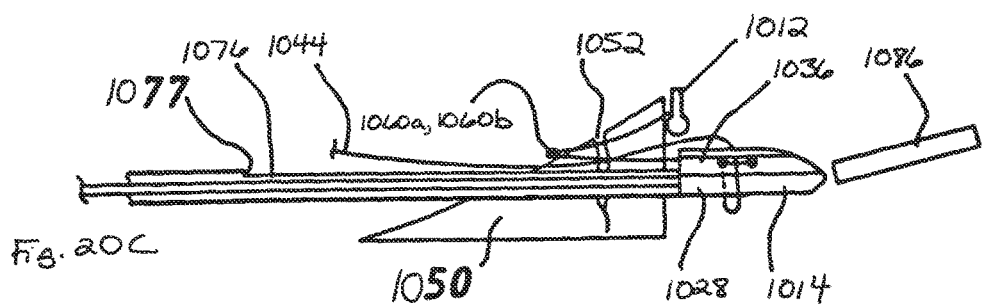
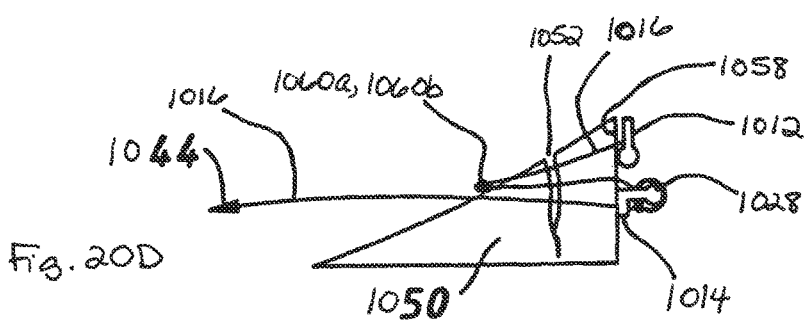

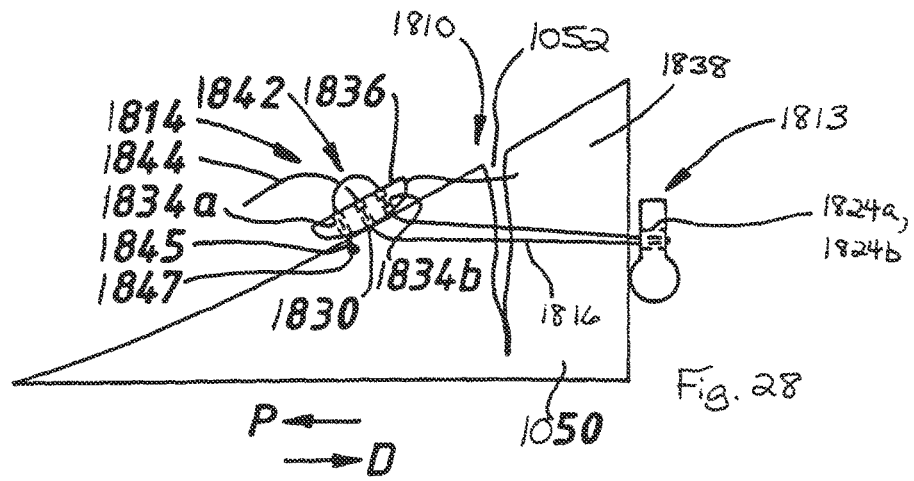
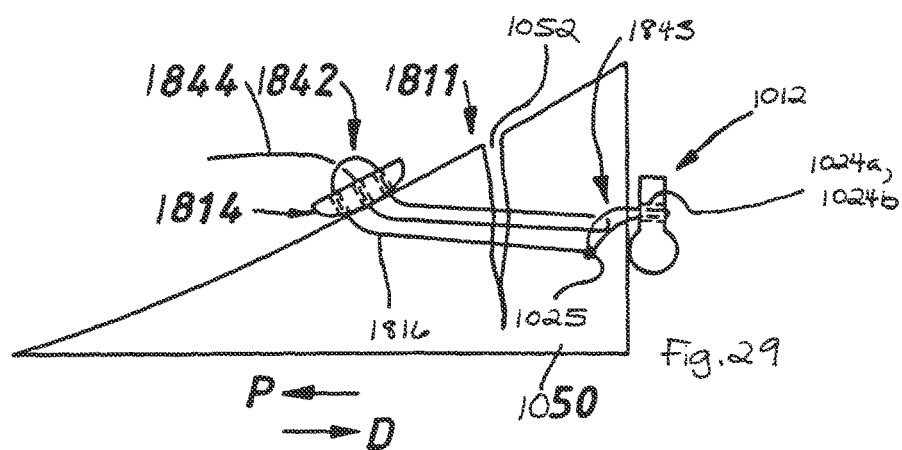
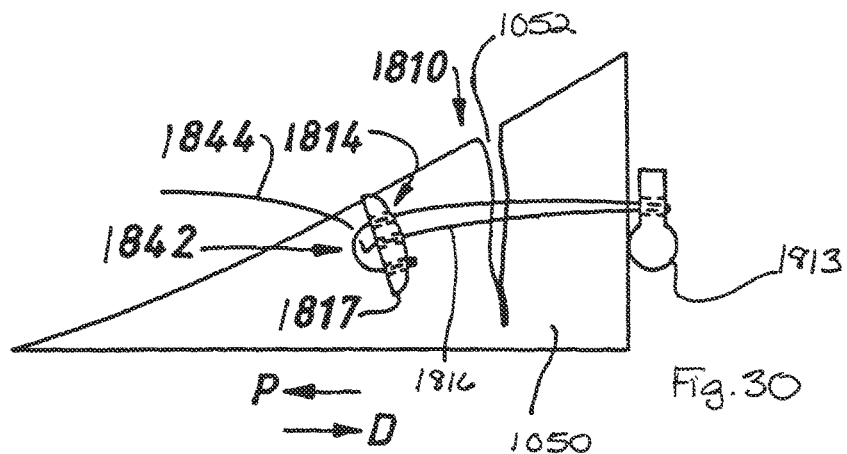

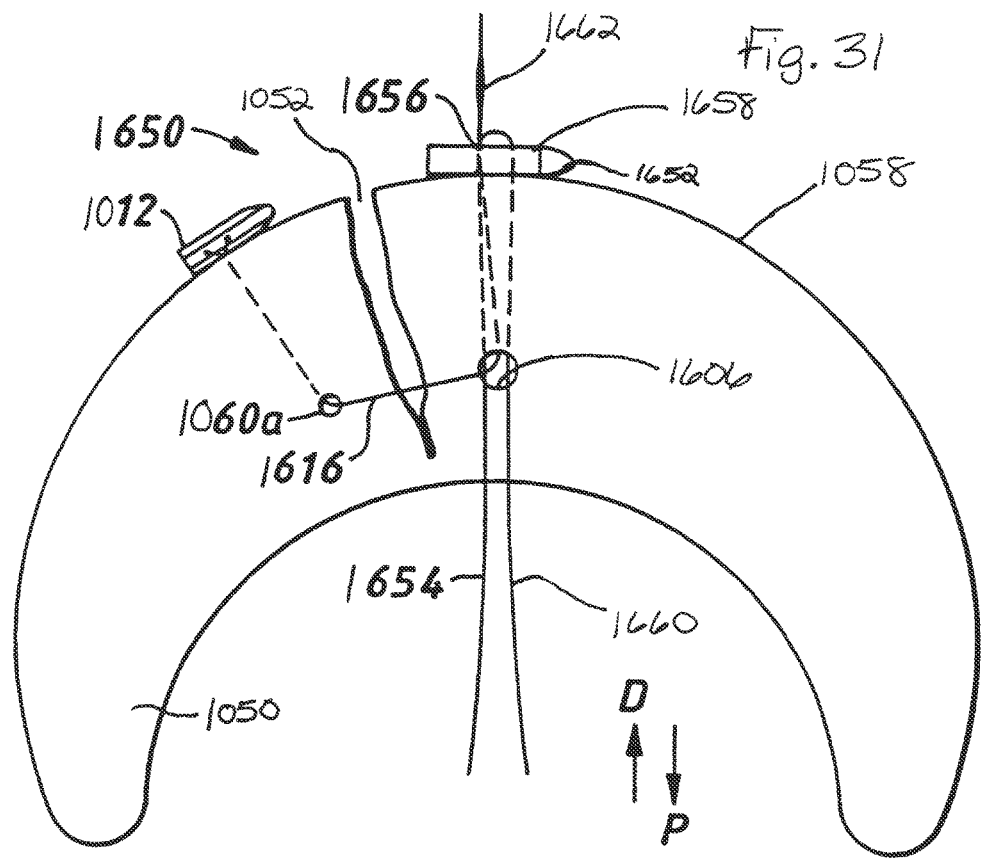
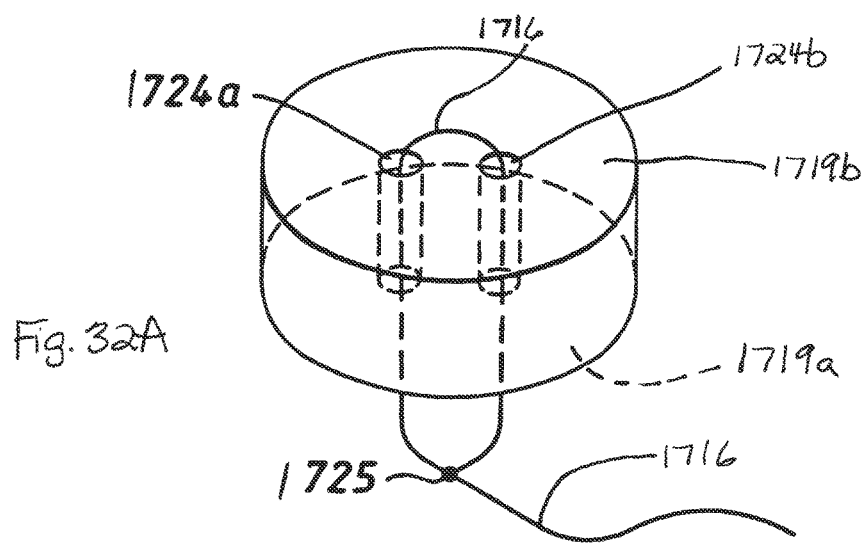

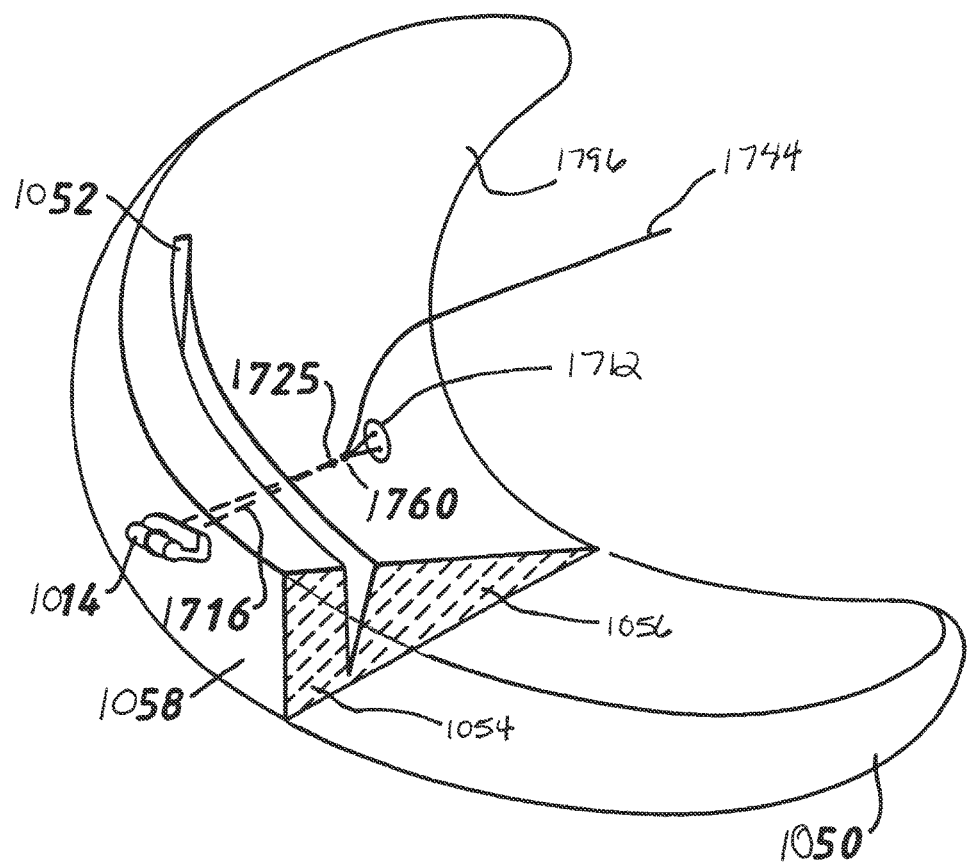

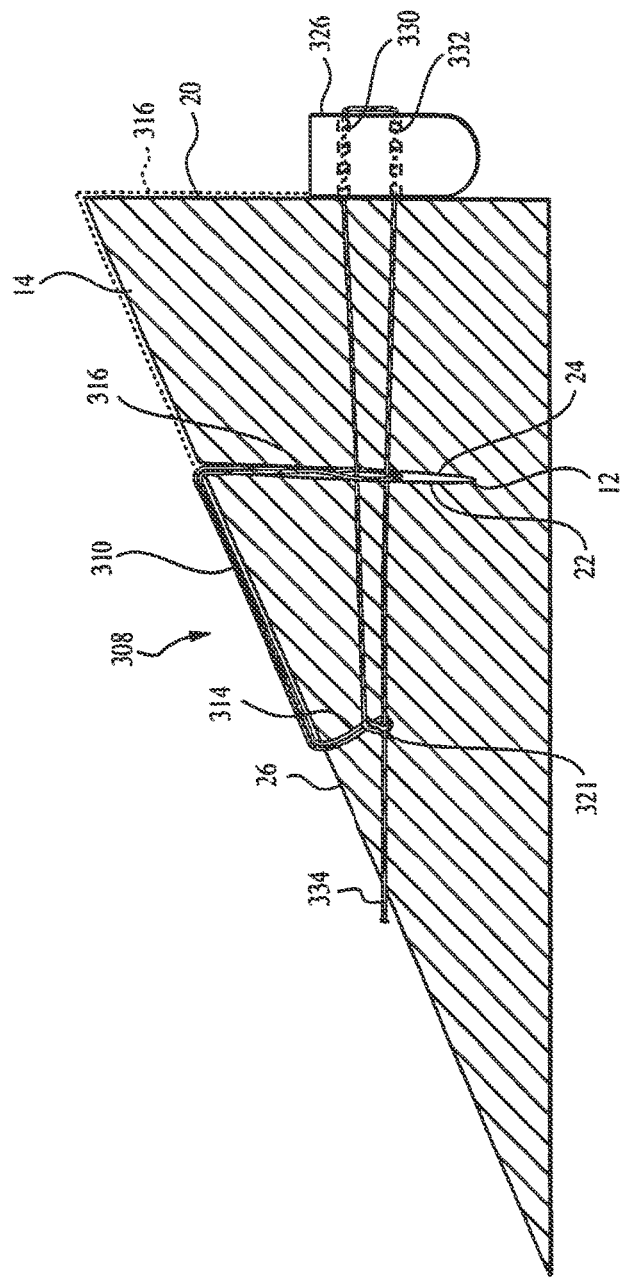

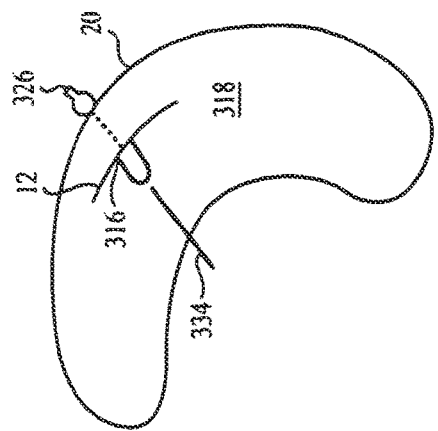
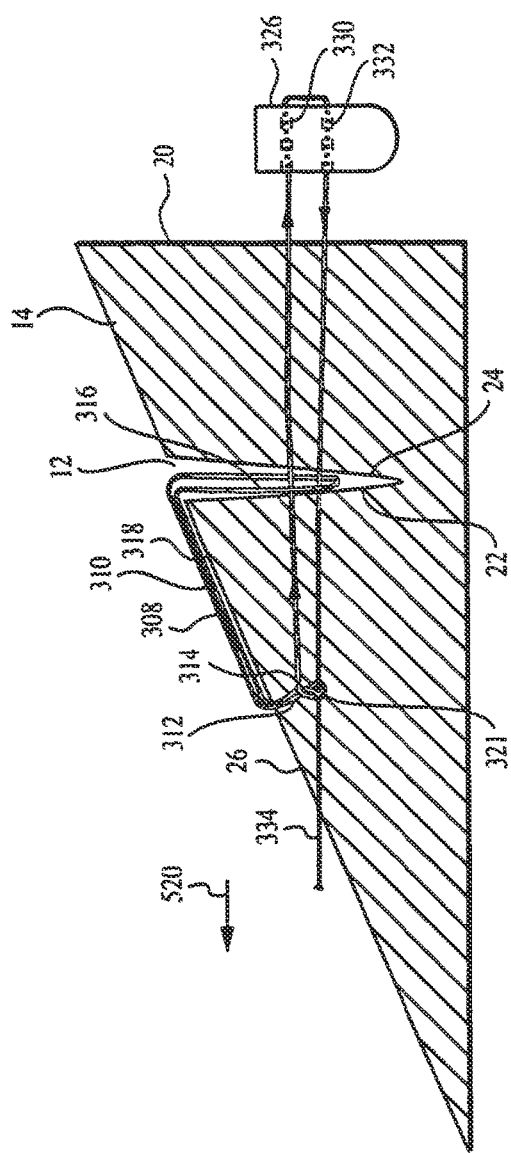
Fig. 35
Fig. 34

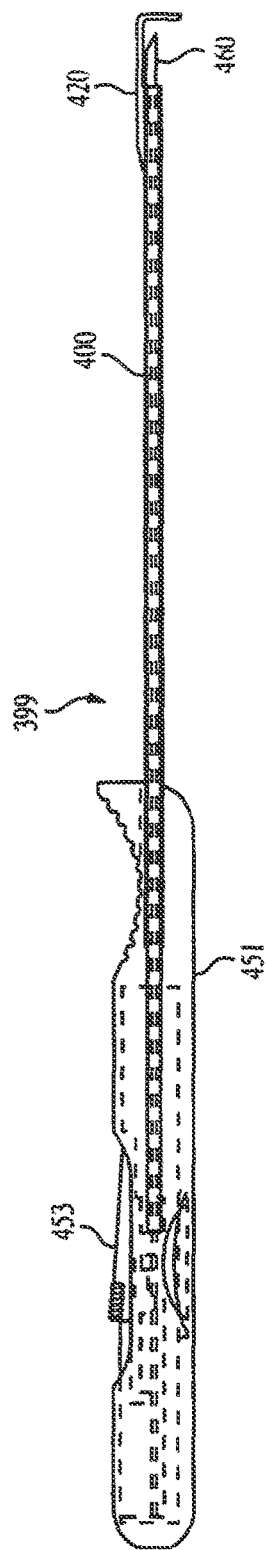
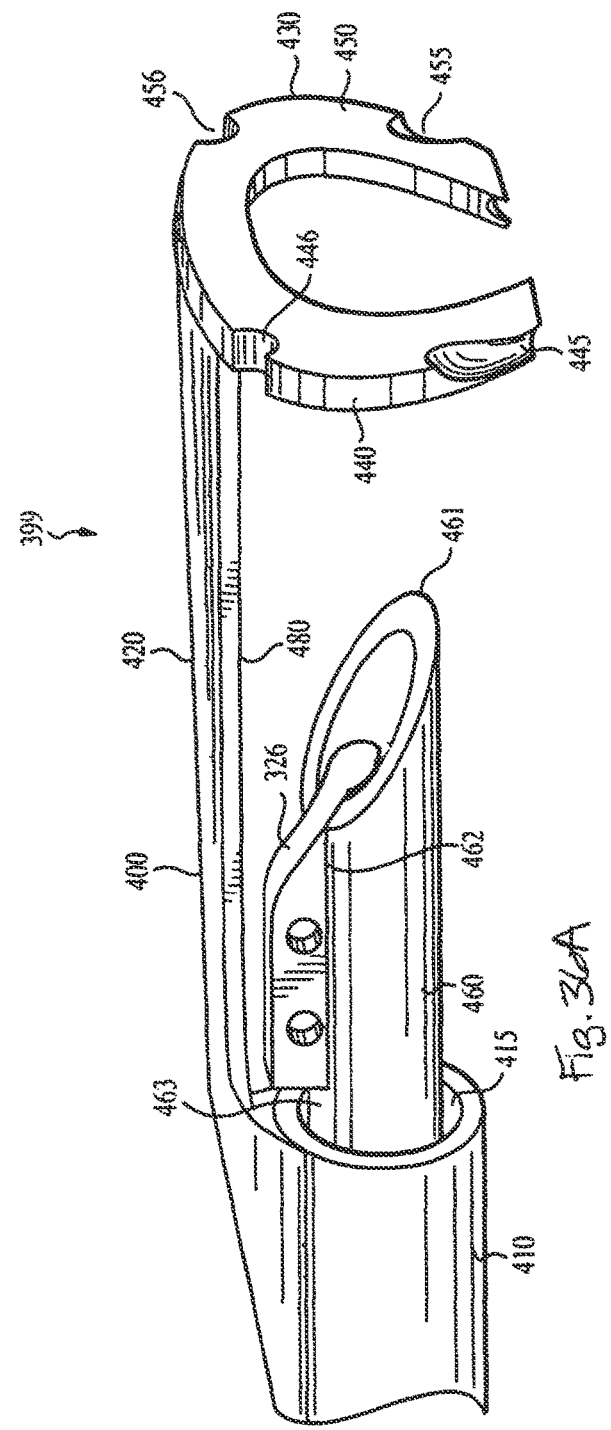

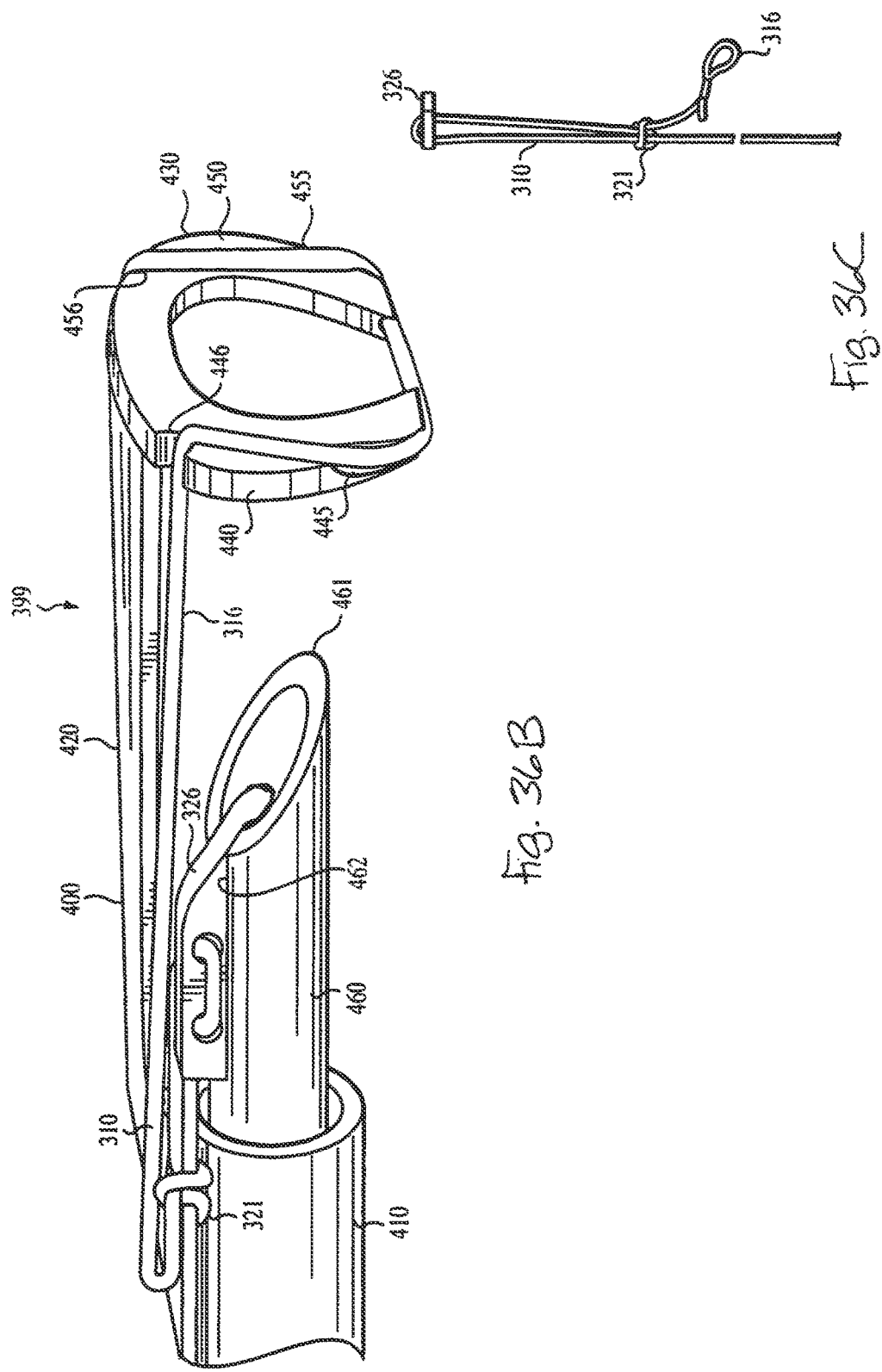

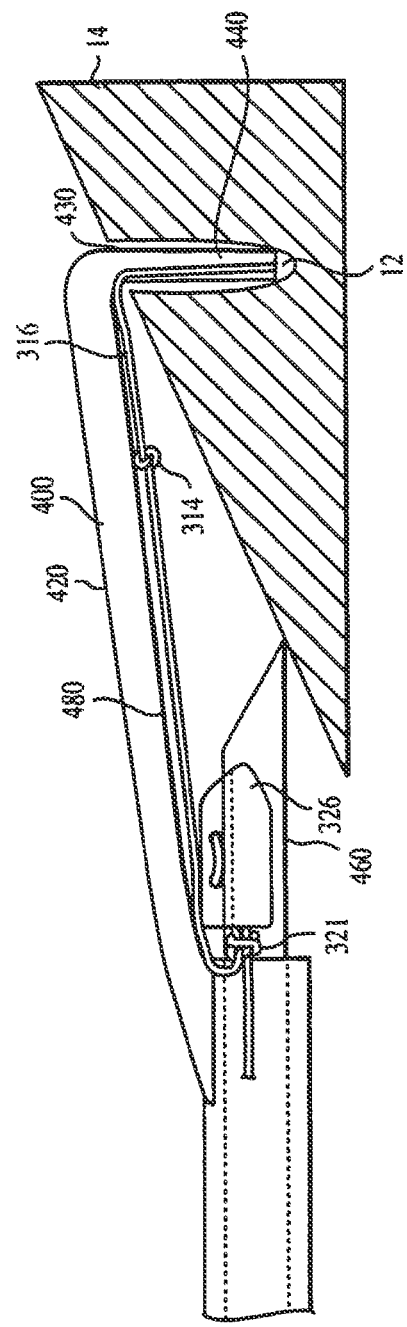

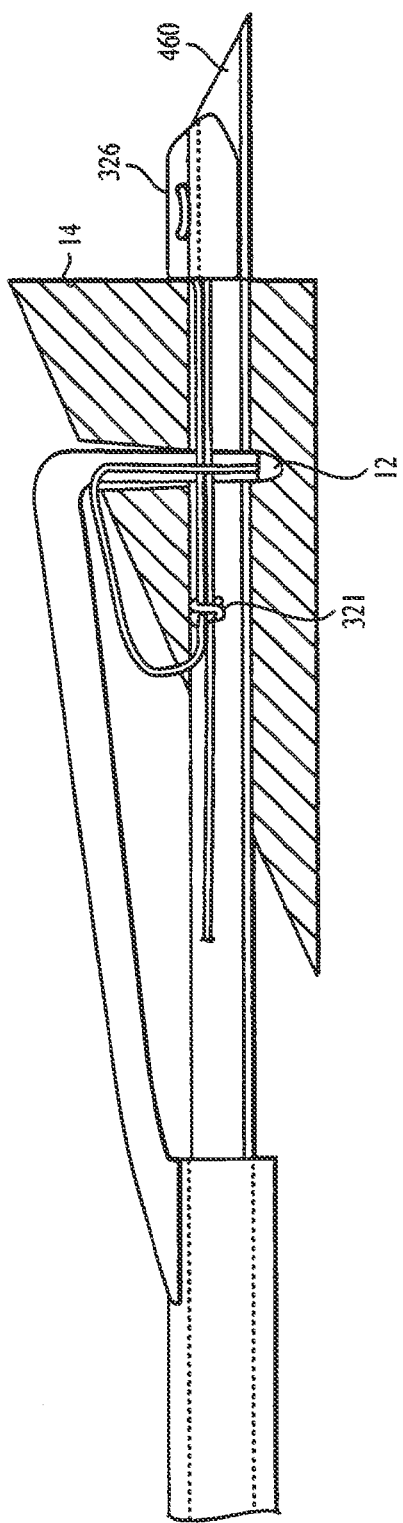

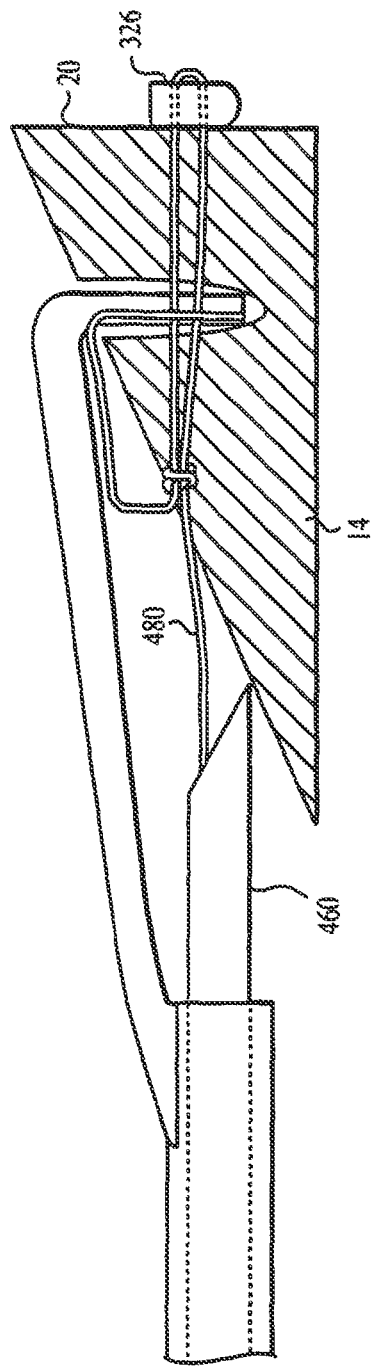

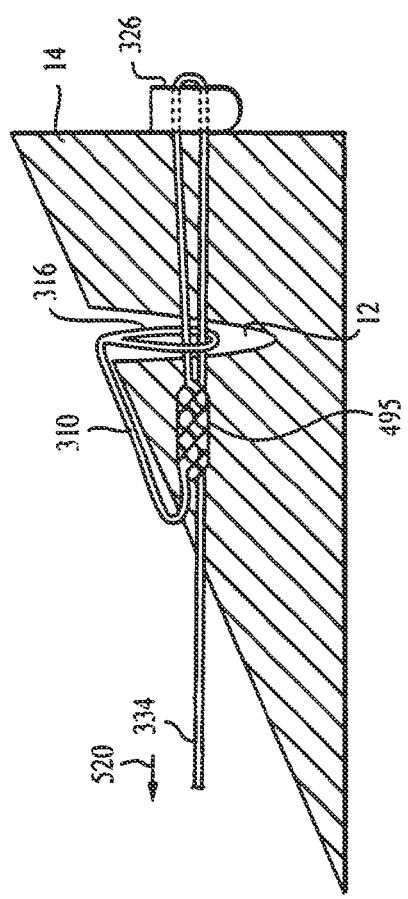

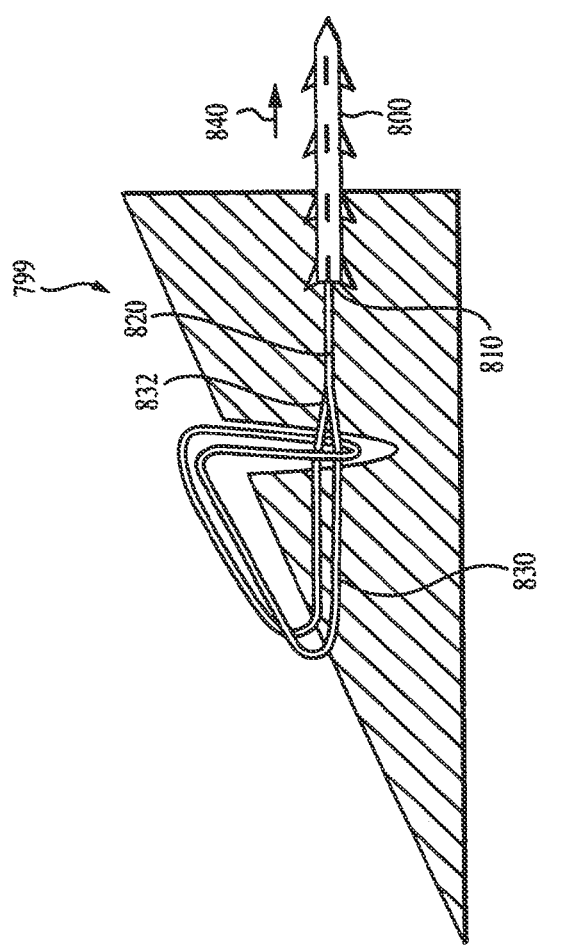

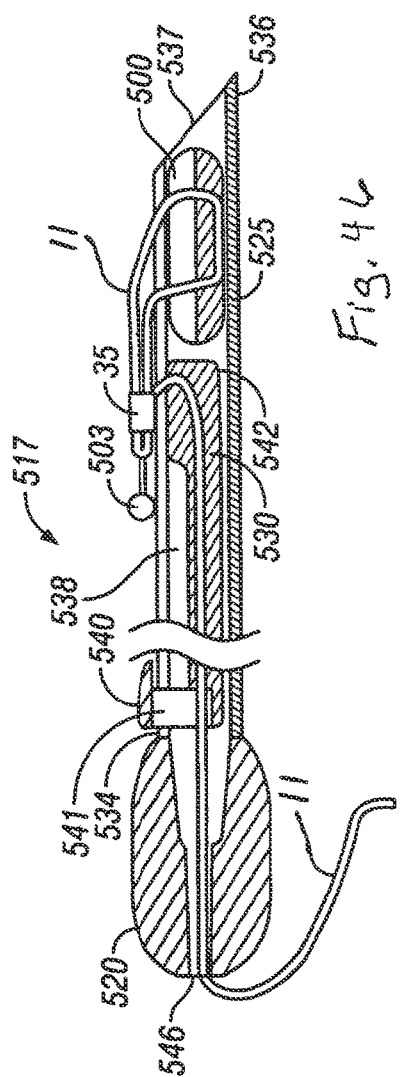
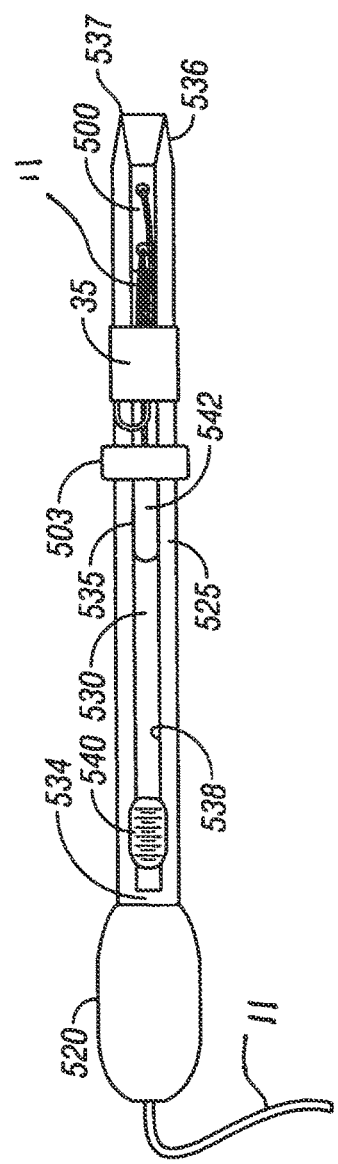

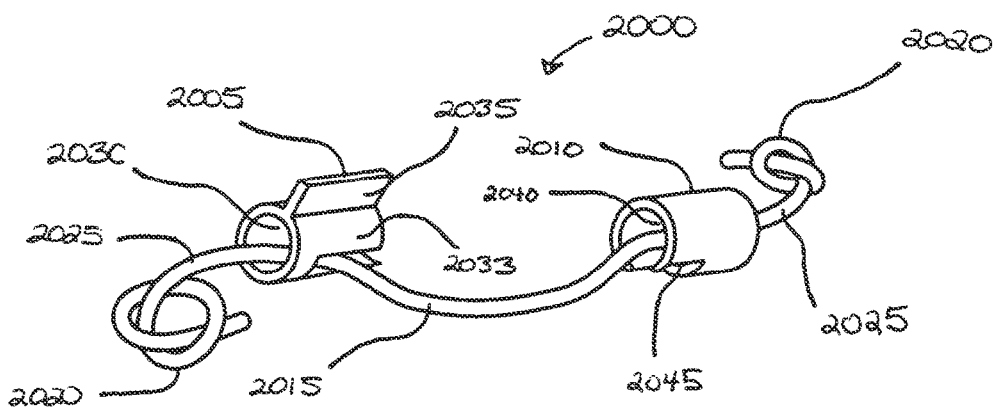
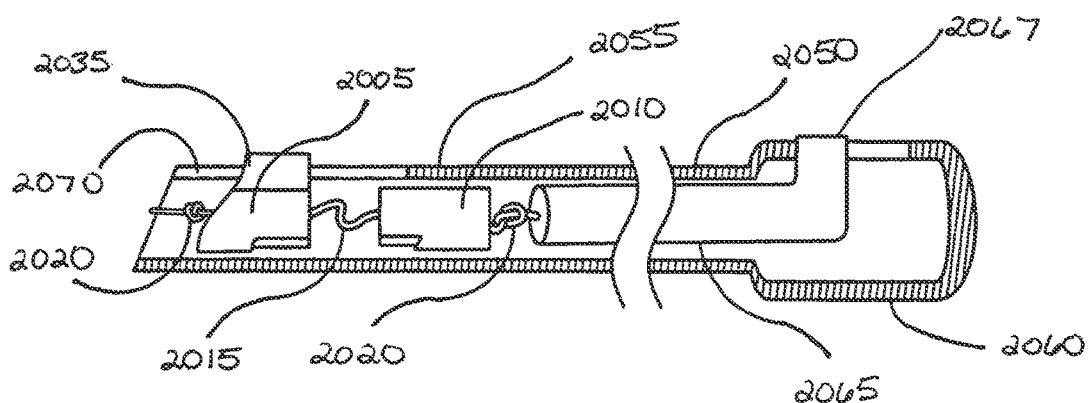

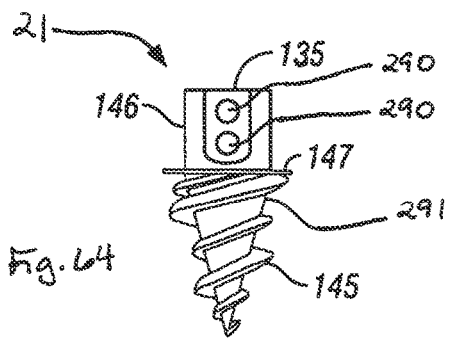
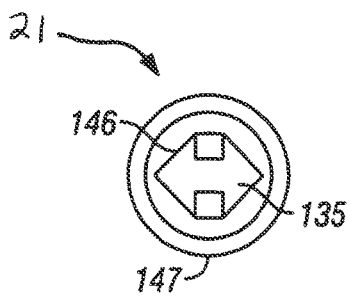
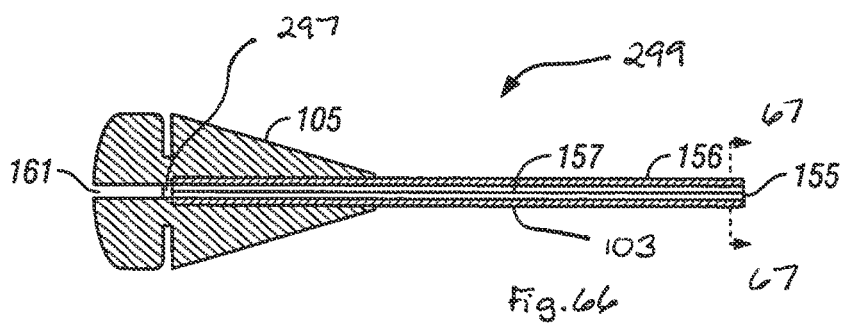
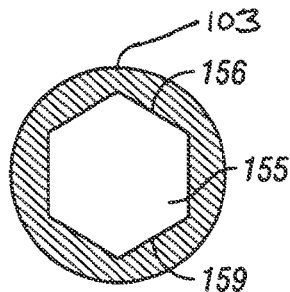
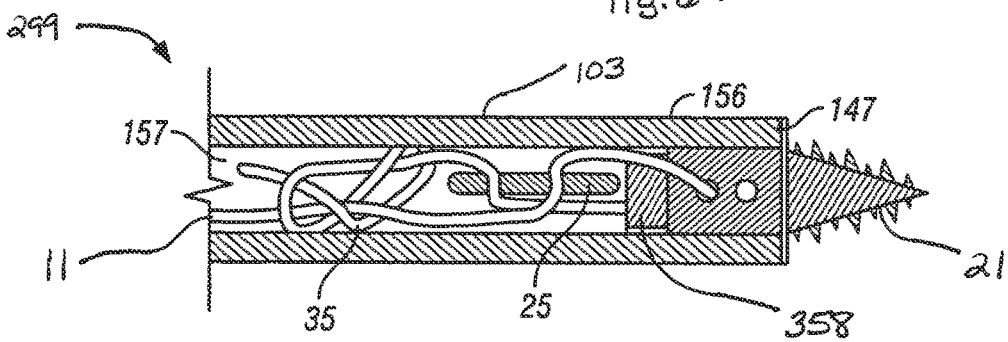

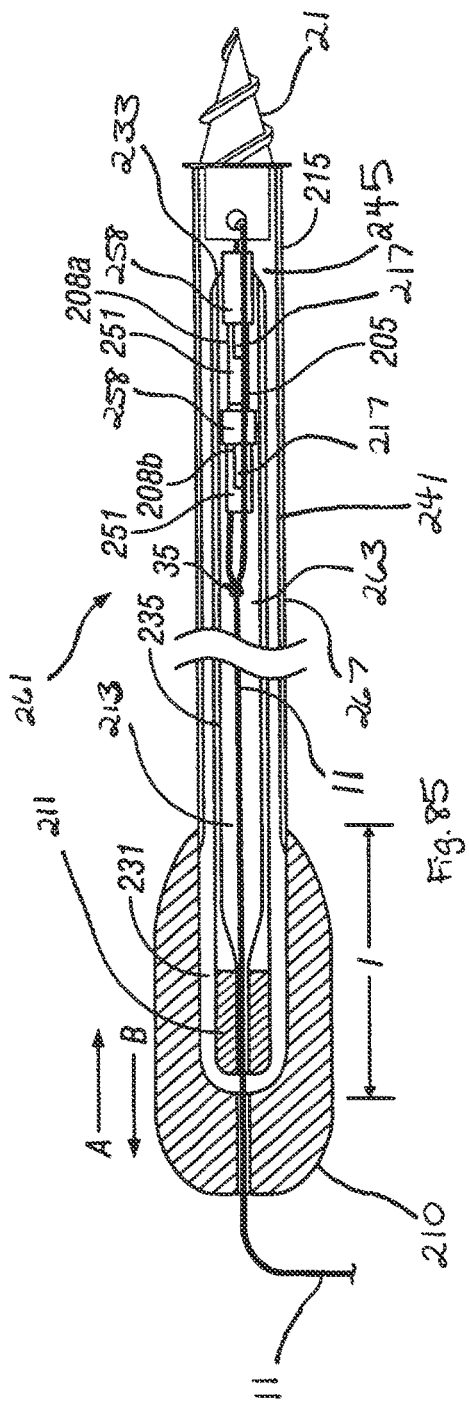

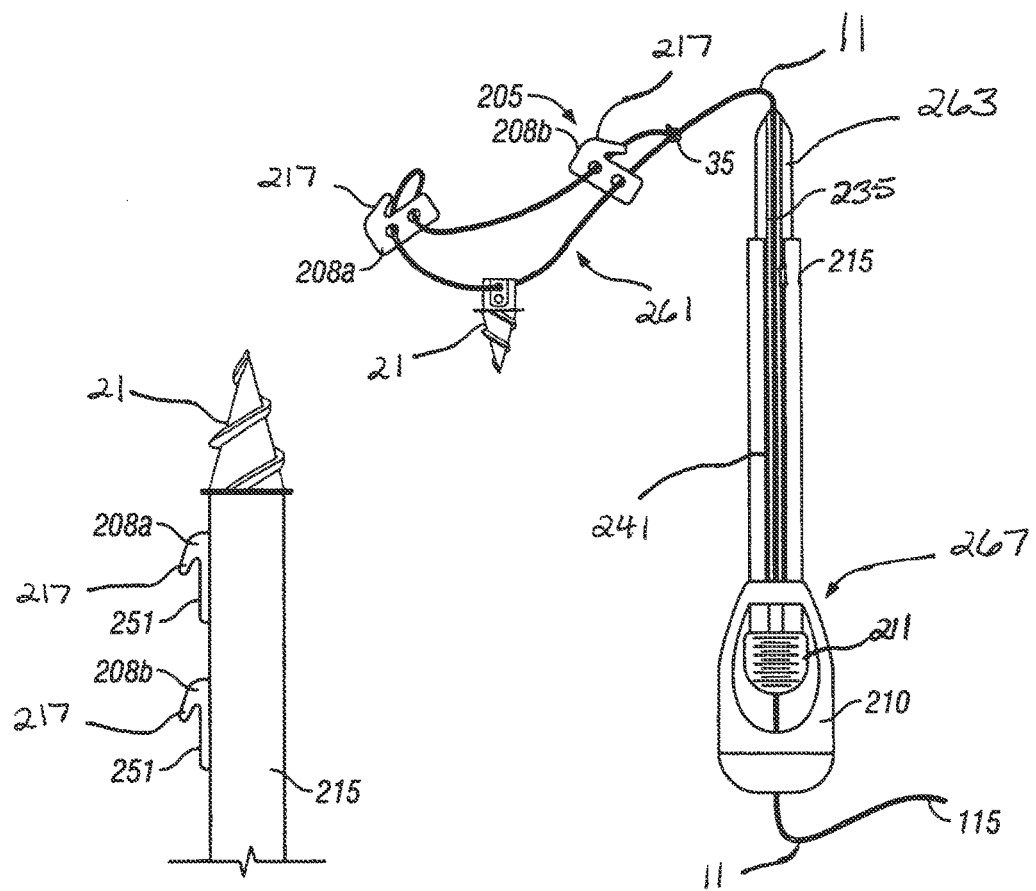

APPARATUS FOR TISSUE REPAIR

CROSS REFERENCE TO RELATED APPLICATIONS

This application is a continuation of U.S. application Ser. No. 13/242,499, filed Sep. 23, 2011; which is a divisional of U.S. application Ser. No. 12/684,722, filed Jan. 8, 2010; which is a continuation of U.S. application Ser. No. 10/918,445, filed Aug. 16, 2004, now U.S. Pat. No. 7,651,509; which is a continuation of U.S. application Ser. No. 10/278,474, filed Oct. 23, 2002, now U.S. Pat. No. 7,887,551; which is a continuation-in-part of U.S. application Ser. No. 09/886,367, filed Jun. 22, 2001, now abandoned; which is a continuation of U.S. application Ser. No. 09/704,926, filed Nov. 2, 2000, now U.S. Pat. No. 7,153,312; and a continuation-in-part of U.S. application Ser. No. 09/453,120, filed Dec. 2, 1999, now abandoned. All of the above applications are incorporated herein by reference in their entirety.

TECHNICAL FIELD

This application relates to devices and methods for repairing tissue.

BACKGROUND

One area in the body where soft tissue is surgically reattached to bone is the attachment of a rotator cuff tendon to the humerus. The rotator cuff tendons have areas of low blood supply. With an increased blood supply, a tissue, such as a tendon, can repair and maintain itself better and faster. Thus, areas of poor blood supply in the rotator cuff make these tendons difficult and slow to heal following an injury, such as a tear to the supraspinatus muscle or the subscapularis muscle. In such a tear, part of the tendon is pulled away from the bone. Because of the poor blood supply, rather than attempting to allow an injured rotator cuff to heal on its own, a physician often recommends that the tendon be surgically repaired to better fix the position of the cuff to the bone to prevent further damage and improve the environment for healing. For example, the physician may attempt to fix the tendon to the bone using a retainer such as an anchor. One example of an anchor is disclosed in U.S. Pat. No. 4,741,330 (the Hayhurst patent), which is incorporated herein by reference.

Other areas in the body also have tissue that can be surgically reattached to bone when torn from the bone or can be surgically repaired when a tear forms in the tissue. These areas include, for example, the biceps tendon, the lateral collateral ligament in the knee, the medial collateral ligament in the knee, the meniscus in the knee, the popliteal ligament in the leg, and the labrum tendon in the knee.

Fibrous tissue wounds, such as muscle, ligament, and cartilage tears, can be repaired arthroscopically using sutures. Traditionally, to close a fibrous tissue wound, a surgeon would insert two suture needles into the tissue with sutures attached, thread the sutures across the wound, and then tie knots to fix the free ends of the sutures within the tissue.

To simplify the wound closure procedure and to improve fixation, various types of retainers have been developed. One example of a retainer is disclosed in the Hayhurst patent. In the Hayhurst patent, one end of a suture is fixed to a resiliently-deformable, bar-shaped retainer. The retainer is loaded into the bore of a hollow needle and deployed into or against the fibrous tissue. The surgeon then threads the suture across the wound and tensions a free end of the suture to pull the wound closed. When the surgeon tensions the suture, the bar in the retainer becomes oriented transversely to the suture hole, anchoring the suture in place.

SUMMARY

In one general aspect, an apparatus includes first and second fixation members, a flexible member coupled to the first and second fixation members, and a limiting element coupled to the flexible member. The limiting element is movable relative to the second fixation member and acts to limit loosening of the flexible member relative to the second fixation member.

Implementations can include one or more of the following features. For example, the limiting element can include a knot formed in the flexible member. The knot can include a slip knot.

The limiting element can define a through bore for receiving the flexible member. The limiting element can define an angled channel for receiving the flexible member. The limiting element can be slidably received on the flexible member.

The flexible member can include a suture. The flexible member can be secured to the first fixation member with a knot. The flexible member can be movably coupled to the second fixation member with a one-way knot.

The fixation members can include a cylindrical portion. The second fixation member can include a T shape. The second fixation member can include a crescent shape. The first fixation member can include a button-shaped portion.

The flexible member can be substantially immovably secured to the first fixation member. The flexible member can be movably coupled to the second fixation member.

At least one of the first and second fixation members can include a retainer. At least one of the first and second fixation members can include a fastener.

In another general aspect, an apparatus includes first and second fixation members, a flexible member coupled to the first and second fixation members, and a limiting element coupled to the flexible member. The limiting element is slidably received by the flexible member and acts to limit loosening of the flexible member relative to the second fixation member.

Implementations can include one or more of the following features. For example, the limiting element can include a knot formed in the flexible member. The knot can include a slip knot.

The limiting element can define a through bore for receiving the flexible member. The limiting element can define an angled channel for receiving the flexible member. The limiting element can be slidably received on the flexible member.

The flexible member can include a suture. The flexible member can be secured to the first fixation member with a knot. The flexible member can be movably coupled to the second fixation member with a one-way knot.

The fixation members can include a cylindrical portion. The second fixation member can include a T shape. The second fixation member can include a crescent shape. The first fixation member can include a button-shaped portion.

The flexible member can be substantially immovably secured to the first fixation member. The flexible member can be movably coupled to the second fixation member. At least one of the first and second fixation members can include a retainer. At least one of the first and second fixation members can include a fastener.

In another general aspect, an apparatus includes a fixation member, and a flexible member movably coupled to the fixation member. A first end of the flexible member is looped back and secured to the flexible member for forming a loop. The loop is remote from the fixation member.

In another general aspect, a surgical assembly includes a first fastener, a second fastener, and a flexible member connecting the first fastener to the second fastener. The flexible member is movably attached to the second fastener, such that pulling on a free end of the flexible member shortens a length of the flexible member between the first and second fasteners.

Implementations can include one or more of the following features. For example, the first fastener can include a first screw, and the second fastener can include a second screw.

The movable attachment of the flexible member to the second fastener can enable the length of the flexible member between the first and second fasteners to be shortened, but not lengthened. The movable attachment can include a knot formed in the flexible member at the second fastener.

The knot can includes a first portion of the flexible member that forms a loop, and a second portion that passes over a surface of the second fastener and through the loop. The surface can comprise an exterior surface of the second fastener. The second portion can include the free end. The knot can be configured such that pulling on the free end causes the flexible member to slide through the loop to shorten the length of the flexible member between the first and second fasteners, but pulling on the flexible member in an opposite direction in order to increase the length of the flexible member between the first and second fasteners causes the loop to press the second portion against a compression surface of the second fastener, resisting increase in the length of the flexible member between the first and second fasteners.

The second fastener can define a partially enclosed region, and the loop can be formed within the partially enclosed region. The second fastener can include a first section that defines a plurality of holes, and the first portion of the flexible member can pass through the plurality of holes to form the loop.

The second fastener can include a second section that defines a passage that connects to the partially enclosed region, and the free end of the suture can pass through the passage.

The second fastener can further include a rounded body and an appendage attached to the rounded body, the rounded body and the appendage defining a partially enclosed region therebetween, wherein at least a portion of the flexible member passes through the partially enclosed region. The flexible member can wrap around the rounded body. The rounded body can have a generally cylindrical shape, and can be sized and shaped to fit within the bore of a hollow needle. The rounded body can define an axial groove, the groove extending across an axial length of the rounded body.

The appendage can have a cross-sectional shape selected from the group consisting of a rectangle, an L, and a D.

The flexible member can be movably attached to the second fastener to form a knot, the knot allowing the length of the flexible member between the first and second fasteners to be shortened, but not lengthened, and the knot including the portion of the flexible member that passes through the partially enclosed region.

The second fastener can have a generally hemispherical shape or a generally crescent shape. The second fastener can have a sharp tip configured to penetrate tissue. The second fastener can be generally T-shaped. The second fastener can define a through-hole, and the flexible member can pass through the through-hole. The surgical assembly can also include a second flexible member that passes through the through-hole, the second flexible member having a thickened portion that has a width greater than a width of the through-hole, such that the thickened portion cannot pass through the through-hole.

The first fastener can include a generally cylindrical body, the body being sized and shaped to fit within a bore of a hollow needle. The first fastener can include a projection extending from the cylindrical body. The projection can include a longitudinal fin. The projection can define a hole for passage of the flexible member therethrough.

The first fastener can have a button shape, and can define a hole for passage of a suture therethrough.

The flexible member can be fixed to the first fastener. The flexible member can include a suture.

The surgical assembly can include a limiting element coupled to the flexible member, the limiting element being slidably received by the flexible member and acting to limit loosening of the flexible member relative to the second fixation member.

The surgical assembly can include a limiting element coupled to the flexible member, the limiting element being movable relative to the second fixation member and acting to limit loosening of the flexible member relative to the second fixation member.

In another general aspect, a wound closure kit includes a needle having an open tip and defining a longitudinal bore that connects to the open tip, first and second fasteners disposed within the needle bore, and a flexible member connecting the first fastener to the second fastener.

Implementations can include one or more of the following features. For example, the needle can define a longitudinal slit that connects to the bore and to the open tip. The first fastener can include a projection that protrudes through the slit. The second fastener can include an appendage that protrudes through the slit, and the flexible member can be attached to the appendage.

The flexible member can be fixed to the first fastener, and movably attached to the second fastener. The flexible member can include a suture.

In another general aspect, a method of closing a tissue wound includes providing a wound closure device having a first fastener, a second fastener, and a flexible member movably attached to the second fastener. The method also includes positioning the first fastener against tissue, passing the flexible member across the wound, positioning the second fastener against tissue, and pulling on a free end of the flexible member to shorten a length of the flexible member between the first and second fasteners, thereby closing the wound.

Implementations can include one or more of the following features. For example, the flexible member can be slidably attached to the second fastener by a one-way knot, such that after completion of the pulling step, the length of the flexible member between the first and second fasteners remains shortened.

The first positioning step can include positioning the first fastener on a first side of the wound. The passing step can include passing the flexible member from the first side to a second side of the wound, engaging tissue on the second side, and returning the flexible member to the first side. The second positioning step can include positioning the second fastener on the first side of the wound.

The providing step can include providing a needle having an open tip and defining a bore that connects to the open tip, the first and second fasteners being at least partially disposed within the bore.

The needle can define a slit that connects to the bore and to the open tip, the first fastener can include a projection that protrudes through the slit, and the first positioning step can include engaging the projection with tissue to remove the first fastener from the bore.

The providing step can include providing a second fastener that defines a partially enclosed region, the partially enclosed region housing at least a portion of the one-way knot, and the partially enclosed region being located such that during the pulling step, the portion of the one-way knot disposed within the partially enclosed region avoids contact with tissue.

The providing step can include providing a device in which the flexible member passes through a through-hole in the second fastener, and the device can also include a second flexible member that also passes through the through-hole, the second flexible member having a thickened portion that is wider than the through hole. The method can also include pulling the second flexible member until the thickened portion wedges into the through hole.

In another general aspect, a method of repairing a tear in a meniscus includes providing a tear closing device having a first fastener, a second fastener, and a flexible member movably attached to the second fastener. The method also includes positioning the first fastener against the meniscus, passing the flexible member across the tear, positioning the second fastener against the meniscus, and pulling on a free end of the flexible member to shorten a length of the flexible member between the first and second fasteners, thereby closing the tear.

Implementations can include one or more of the following features. For example, the providing step can include providing a tear closing device in which the flexible member is fixed to the first fastener. The first positioning step can include positioning the first fastener against an external surface of the meniscus, on a first side of the tear. The passing step can include passing the flexible member from the first side to a second side of the tear, engaging tissue on the second side, and returning the flexible member to the first side. The second positioning step can include positioning the second fastener against the external surface.

The first and second fasteners can be positioned against external surfaces of the meniscus on opposite sides of the tear.

In another general aspect, a surgical method includes positioning a fixation member relative to tissue, moving a flexible member coupled to the fixation member relative to the fixation member to bring two tissue surfaces together, and moving a limiting element coupled to the flexible member relative to the fixation member. The limiting element acts to limit loosening of the flexible member relative to the fixation member.

Implementations can include one or more of the following features. For example, the step of moving the flexible member can include pulling the flexible member. The step of moving the flexible member can also accomplish the step of moving the limiting element. The surgical method can also include providing the limiting element in the form of a slip knot.

The step of moving the limiting element can include moving the limiting element relative to the flexible element. The surgical method can include providing the limiting element in the form of a friction element that permits sliding of the limiting element relative to the flexible element in only one direction.

The surgical method can include providing the limiting element in the form of an overhand knot. The surgical method can include advancing the overhand knot along the flexible element. The surgical method can include providing the limiting element in the form of a Chinese trap.

The step of moving the flexible member can include pulling on only one end of the flexible member.

The surgical method can include positioning a second fixation member relative to the tissue, the second fixation member being coupled to the flexible member. The second fixation member can be movably coupled to the flexible member, and the step of moving the flexible member can include pulling on two ends of the flexible member. The second fixation member can be fixedly attached to the flexible member, and the step of moving the flexible member can include pulling on only one end of the flexible member.

The step of positioning the fixation member can include positioning the fixation member on an outer surface of the tissue. The two tissue surfaces can be both soft tissue. The step of positioning the fixation member can include positioning the fixation member in a bone hole.

A first of the two tissue surfaces can be bone, and a second of the two tissue surfaces can be soft tissue.

The step of positioning the fixation member can include passing the fixation member through a loop of the flexible member. The surgical method can also include positioning the loop within a tear in soft tissue.

In another general aspect, a method for repairing a tear in soft tissue includes advancing a fixation member coupled to a flexible member through tissue on either side of the tear and through a loop of the flexible member, and tensioning the flexible member to bring two tissue surfaces on either side of the tear together.

Implementations can include one or more of the following features. For example, the method can include positioning the loop within the tear. The method can include pulling an end of the flexible member to bring the two tissue surfaces together. The method can include providing the fixation member in the form of a barbed member.

In another general aspect, a surgical assembly includes a fastener configured to be secured within bone tissue, a retainer for engaging tissue, and a flexible member connecting the fastener to the retainer. The flexible member is movably attached to the retainer such that pulling on a free end of the flexible member shortens a length of the flexible member between the fastener and the retainer to urge the tissue against the bone tissue.

Implementations can include one or more of the following features. For example, the movable attachment of the flexible member to the retainer can be configured to enable the length of the flexible member between the fastener and the retainer to be shortened, but not lengthened.

The movable attachment can include a knot formed in the flexible member. The knot can include a slip knot. The flexible member can include a suture.

The retainer can include a smooth first surface and a second surface that includes protrusions. The retainer can include a smooth first surface and a second surface having a length and protrusions that are transverse to the length of the second surface. The retainer can have a low profile such that the retainer does not protrude sufficiently from the tissue to impinge against adjacent tissue. The retainer can have a thickness of between approximately 0.5 and 2.5 millimeters. The retainer can have a thickness of approximately 2 millimeters.

The fastener can include a screw. The screw can include a threaded shank and a head, and the head can define at least one opening and the flexible member can pass through the opening. The screw can include a ridge between the shank and the head.

The surgical assembly can include a delivery device for delivering the fastener and the retainer to a surgical site. The delivery device can include a cannula defining a lumen for receiving the fastener and the retainer.

The surgical assembly can include a retractable needle positioned within the lumen and connected to a switch in the delivery device for advancing and retracting the needle.

In another general aspect, a surgical method includes positioning a fastener within bone tissue, positioning a retainer against soft tissue to be attached to the bone tissue, the fastener and retainer being connected by a flexible member, the flexible member being movably attached to the retainer, and pulling a free end of the flexible member to shorten a length of the flexible member between the fastener and the retainer to urge the soft tissue against the bone tissue.

Implementations can include one or more of the following features. For example, the movable attachment of the flexible member to the retainer can enable shortening but not lengthening of the length of the flexible member between the fastener and the retainer. The movable attachment can include a slip knot formed in the flexible member and pulling the free end can move the slip knot along the flexible member.

The positioning of the fastener within bone tissue can include rotatably inserting the fastener into bone tissue.

The positioning of the retainer against soft tissue can include locating the retainer within a needle, passing the needle through the soft tissue such that a protrusion on the retainer passes through at least a portion of the soft tissue, and withdrawing the needle from the soft tissue such that the retainer is pulled from the needle by the interaction of the protrusion and the soft tissue. The surgical method can also include positioning a second retainer against the tissue on a side of the tissue opposite that of the first retainer. The second retainer can be positioned within the needle, the flexible member can connect the second retainer to the first retainer and the fastener, and withdrawing the needle from the tissue can cause the flexible member to be under tension such that the second retainer is pulled from the needle.

The pulling of the free end of the flexible member can move a slip knot along the flexible member, the slip knot being positioned between the free end of the flexible member and the second retainer.

The retainer can have a low profile such that the retainer does not protrude sufficiently to impinge against adjacent tissue when the retainer is positioned against soft tissue. The retainer can have a thickness of between approximately 0.5 and 2.5 millimeters. The retainer can have a thickness of approximately 2 millimeters.

In another general aspect, a surgical assembly includes a delivery device including a handle and a cannula, the cannula extending from the handle and including a longitudinal channel and a longitudinal slot in the cannula along at least a portion of the length of the channel, and a surgical device including a first fixation member, a second fixation member, a flexible member coupling the first fixation member and the second fixation member, the flexible member being movably attached to the first fixation member such that pulling on a free end of the flexible member shortens a length of the flexible member between the first fixation member and the second fixation member. The first fixation member is positioned within the longitudinal channel, the second fixation member is positioned adjacent to an outer surface of the cannula, and the flexible member passes from the longitudinal channel through the longitudinal slot.

Implementations can include one or more of the following features. For example, the surgical assembly can include a pusher tube slidably positioned within the cannula and including a thumb switch extending through the longitudinal slot for advancing and retracting the pusher tube.

The movable attachment can include a slip knot. The movable attachment can be positioned within the longitudinal channel. The movable attachment can be positioned outside of the longitudinal channel.

In another general aspect, a surgical method includes drilling a channel through bone tissue and soft tissue and pulling a first flexible member to pull a fastener in a first direction through the channel such that the fastener passes through the bone tissue and the soft tissue. The method includes pulling a second flexible member to pull the fastener in a second direction against the soft tissue, the second flexible member connecting the fastener to a retainer. The method also includes pulling a free end of the second flexible member to shorten a length of the second flexible member between the fastener and the retainer, whereby pulling the free end of the second flexible member positions the retainer against the bone.

In another general aspect, a surgical method includes positioning a fastener within bone tissue, positioning a first retainer against soft tissue to be attached to the bone tissue, the fastener and first retainer being movably attached by a flexible member, positioning a second retainer against soft tissue to be attached to the bone tissue, the fastener, the first retainer, and the second retainer being movably attached by the flexible member, and pulling a free end of the flexible member to shorten a length of the flexible member between at least any two of the fastener, the first retainer and the second retainer.

Implementations can include one or more of the following features. For example, the movable attachment of the flexible member to the retainer can enable shortening but not lengthening of the length of the flexible member between any two of the fastener, the first retainer, and the second retainer. The pulling of the free end of the flexible member can move a slip knot along the flexible member, the slip knot being positioned between the free end of the flexible member and the second retainer. The positioning of the fastener within bone tissue can include rotatably inserting the fastener into bone tissue.

The positioning of either of the first retainer and the second retainer against soft tissue can include locating the retainer within a needle, passing the needle through the soft tissue such that a protrusion on the retainer passes through at least a portion of the soft tissue, and withdrawing the needle from the soft tissue such that the retainer is pulled from the needle by the interaction of the protrusion and the soft tissue.

The pulling of a free end of the flexible member can include moving a slip knot positioned between a free end of the flexible member and the second retainer along the flexible member to shorten a length of the flexible member between at least any two of the fastener, the first retainer, and the second retainer.

In another general aspect, a surgical method includes positioning a fastener within bone tissue, and advancing a delivery device including a needle under a first soft tissue member. The method includes advancing the curved delivery device through a second soft tissue member and positioning a retainer against the second soft tissue member. The fastener and retainer are connected by a flexible member, and the flexible member is movably attached to the retainer. The method also includes pulling a free end of the flexible member to shorten a length of the flexible member between the fastener and the retainer.

Implementations can include one or more of the following features. For example, the movable attachment of the flexible member to the retainer can enable shortening but not lengthening of the length of the flexible member between the fastener and the retainer.

The pulling of the free end can move the slip knot along the flexible member, the slip knot being formed in the flexible member.

The positioning of the fastener within bone tissue can include forcibly inserting the fastener into bone tissue.

The positioning of the retainer against the second soft tissue can include locating the retainer within the needle, passing the needle through the second soft tissue such that a protrusion on the retainer passes through at least a portion of the second soft tissue, and withdrawing the needle from the second soft tissue such that the retainer is pulled from the needle by the interaction of the protrusion and the second soft tissue.

The delivery device can be advanced under the first soft tissue member and the retainer can be positioned against the second soft tissue member prior to positioning the fastener within the bone tissue.

In another general aspect, a surgical method for repairing a meniscal tear includes positioning a delivery device having a needle against a first position on soft tissue, and advancing the needle through the soft tissue. A first fixation member is positioned within a longitudinal channel of a lumen of the needle and includes a protrusion extending from the first fixation member through a longitudinal slot in the needle. The method includes withdrawing the needle from the soft tissue such that the first fixation member is pulled from the needle by the interaction of the protrusion and the soft tissue. The method also includes positioning the delivery device against a second position on the soft tissue, and advancing the delivery device and the needle through the soft tissue. A second fixation member is positioned within the longitudinal channel of the lumen and includes a protrusion extending from the second fixation member through the longitudinal slot in the needle. The method includes withdrawing the delivery device from the soft tissue such that the second fixation member is pulled from the needle by the interaction of the protrusion and the soft tissue.

Implementations can include one or more of the following features. For example, the positioning of the first fixation member and the second fixation member can include positioning the first fixation member and the second fixation member on opposite sides of the meniscal tear. The positioning of the first fixation member and the second fixation member can include positioning the first fixation member and the second fixation member on the same side of the meniscal tear.

In another general aspect, a device for repairing a tear in a tissue includes a needle having a distal region and a proximal region, the distal region being defined between two holding elements, a first fixation member positioned within the distal region and a second fixation member positioned within the proximal region, and a flexible member coupled to the first and second fixation members.

Implementations can include one or more of the following features. For example, one of the holding elements can include a crimp in the needle in the distal region. One of the holding elements can include a dimple extending into a lumen of the needle. One of the holding elements can include a ramp extending into a lumen of the needle.

The needle can define a slot through a wall of the needle, the first and second fixation members extending through the slot.

The device can also include a protector tube, the tube defining a bore, wherein the needle is sized to fit into an end of the protector tube. The device can include a push pin, the pin being sized to fit inside the needle.

Embodiments can include one or more of the following advantages. The first and second fixation members can be deployed using a single hollow needle, rather than two separate needles. After deploying a fixation member, the surgeon need not tie an additional knot. The length of a flexible member coupled to the fixation member can be adjusted after deploying the fixation member, allowing a surgeon to set the tension in the flexible member to a desired level. The length of a flexible member spanning across a tear in tissue can be shortened to close the tear by tensioning the flexible member with no additional manipulation being required to limit loosening of the flexible member.

Since the device uses a flexible member, such as a suture, to close the tissue wound, rather than inflexible staples or tacks, the tissue is not significantly damaged when it expands and contracts. For example, if the soft tissue is a meniscus, the fixation members do not damage the meniscal tissue when the knee moves.

Additionally, the physician does not need to tie any knots and the fixation members have a low profile, which limits protrusion of the fixation members into the joint capsule. For example, the devices and methods provide an optimal repair and reattachment of soft tissue to bone by first providing optimal fixation when the devices are placed and then providing an easily manipulated limiting elements (for example, the slip knot) that fixes the position of the fixation members against the bone and tissue. Because the system uses optimal fixation prior to tightening the slip knot, a fixation members can be used in bone tissue that has a less than optimal tissue condition, such as osteoporotic bone.

Moreover, the procedure is simple and easy. For example, in one embodiment, the fastener is rotatably positioned within the bone, the delivery device is withdrawn, a knot pusher is used to tighten the slip knot to place the retainer against the tendon, and the proximal end of the suture is cut. Thus, the physician does not need to tie any knots or reach through tissue to manipulate any of the components used in the procedure.

Other features will be apparent from the description, the drawings, and the claims.

DESCRIPTION OF DRAWINGS

FIG. 1 is an illustration of a closure device, shown mending a tear in soft tissue.

FIG. 3 is a perspective view of a delivery device for inserting the closure device of FIG. 1 into soft tissue.

FIG. 4 is a perspective view of the delivery device of FIG. 3 shown with an outer sheath removed.

FIG. 4A is a perspective view of a fixation member of the closure device of FIG. 1.

FIG. 4B is a cross-sectional end view of the delivery device of FIG. 4, taken along lines 19B-19B.

FIG. 4C is a cross-sectional side view of an alternative embodiment of a needle of the delivery device of FIG. 3.

FIGS. 6-11 show the delivery device in use inserting the closure device of FIG. 1 in soft tissue, with FIG. 7 being an exploded view of region 7 of FIG. 6.

FIG. 13 shows an additional alternative embodiment of a limiting element in the form of an overhand knot.

FIGS. 13A and 13B show an overhand knot and a knot pusher for advancing the overhand knot of FIG. 13.

FIG. 15A is a perspective view of a wound closure device.

FIG. 15B is a side view of a first fixation member of the wound closure device of FIG. 15A.

FIG. 15C is a side view of a second fixation member of the device of FIG. 15A.

FIG. 15D is an enlarged view of a braided suture.

FIG. 16 is a perspective, cut-away view of a meniscus in which the wound closure device of FIG. 15A has been implanted.

FIGS. 17A and 17B are sectional views of, respectively, a second fixation member and one-way knot of the wound closure device of FIG. 15A.

FIGS. 19A-19D are schematics illustrating deployment of the wound closure device of FIG. 15A into a meniscus using a plunger.

FIGS. 20A-20D are schematics illustrating deployment of the wound closure device of FIG. 15A into a meniscus using a plunger and a spacer.

FIGS. 28-30 are sectional views showing deployment of wound closure devices that include the crescent-shaped fixation member of FIG. 27C.

FIG. 31 is a perspective, partially schematic view of an alternative wound closure device implanted within a meniscus.

FIG. 32A is a perspective view of an alternative first fixation member design for a wound closure device.

FIG. 32B is a perspective, cut-away view of a meniscus in which the wound closure device of FIG. 33A has been implanted.

FIG. 33 is a cross-sectional side view of an alternative embodiment of a closure device, shown mending a tear in soft tissue.

FIG. 34 shows the closure device of FIG. 33 in use prior to securing the closure device in place.

FIG. 35 is a top view of the closure device of FIG. 33, shown after securing the closure device in place.

FIG. 36 is a side view of a delivery device for inserting the closure device of FIG. 33 in soft tissue.

FIG. 36A is a perspective view of a distal section of the delivery device of FIG. 36 shown with a fixation member of the closure device of FIG. 33.

FIG. 36B is a perspective view similar to that of FIG. 36A shown with the closure device of FIG. 33.

FIG. 36C is an illustration of the closure device of FIG. 33.

FIGS. 37-39 show the delivery device of FIG. 36 in use inserting the closure device of FIG. 33 in soft tissue.

FIG. 40 is a cross-sectional side view of the closure device of FIG. 33 with an alternative embodiment of a limiting element, shown mending a tear in soft tissue.

FIG. 41 is a cross-sectional side view of an alternative embodiment of a closure device, similar in use to the closure device of FIG. 33.

FIG. 46 is a cross-sectional side view of the surgical device of FIG. 44 shown positioned within the delivery device for delivering the surgical device to a surgical site.

FIG. 47 is a top view of the surgical device and delivery device of FIG. 46.

FIG. 54 is a side view of a surgical device for repairing a meniscal tear.

FIG. 55 is a cross-sectional side view of a delivery device for delivering the surgical device of FIG. 54.

FIG. 64 is a side view of the fastener of the surgical device of FIG. 60.

FIG. 65 is a top view of the fastener of FIG. 64.

FIG. 66 is a cross-sectional side view of the delivery device of FIG. 62.

FIG. 67 is an end view of the delivery device of FIG. 66 taken at section lines 67-67 of FIG. 66.

FIG. 68 is a cross-sectional side view of the distal end of the delivery device illustrating the surgical device of FIG. 60 positioned within the delivery device.

FIG. 85 is a cross-sectional side view of an alternative embodiment of a surgical assembly for placing a fastener and one or more retainers.

FIGS. 86 and 87 are side and top views of a retractable needle and handle of a delivery device of the surgical assembly of FIG. 85.

FIG. 88 shows a distal region of the surgical assembly of FIG. 85 illustrating the fastener and two barbed retainers positioned in the delivery device.

FIG. 89 illustrates the arrangement of the fastener, barbed retainers, and suture of the surgical device of FIG. 85.

Like reference symbols in the various drawings indicate like elements.

DETAILED DESCRIPTION

Figure 2A:
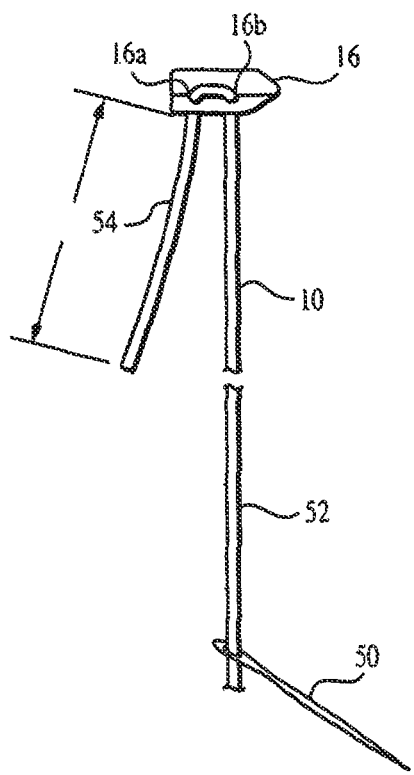
FIGS. 2A-2I show a method of tying a slip knot in suture of the closure device of FIG. 1.

Referring to FIG. 1, a closure device 8 for mending a tear 12 in soft tissue 14, for example, the meniscus of the knee joint, includes a flexible member, for example, suture 10, coupled to a first fixation member (for example, a first retainer) 16 and a second fixation member (for example, a second retainer) 18. The meniscus is a C-shaped, rubbery, shock-absorbing structure located between the tibia and the femur inside the knee. Suture 10 is fastened to fixation member 16 to limit movement of suture 10 relative to the first fixation member 16, while suture 10 is movable relative to the second fixation member 18.

Figure 11:
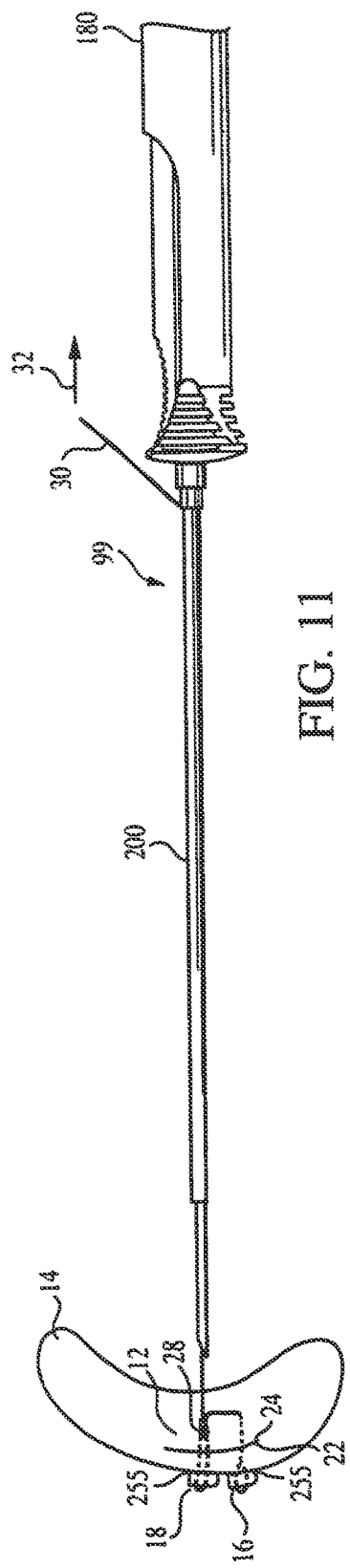

When implanted in the knee joint, the fixation members 16 and 18 lie on a surface 20 of tissue 14, for example, the outer surface of the meniscus. Suture 10 has a first suture length 10a extending from first fixation member 16 through tissue 14, traversing the tear 12, and emerging at a surface 26 of tissue 14; a second suture length 10b extending across the surface 26; a third suture length 10c extending back through tissue 14, traversing the tear 12 at a location spaced from the first length 10a, and emerging at the tissue surface 20 where suture 10 loops through the second fixation member 18; and a fourth suture length 10d extending from the second fixation member 18 through tissue 14, traversing the tear 12, and emerging at the surface 26. Suture 10 has a free end 30 that the surgeon pulls, in the direction of arrow 32, to bring sides 22, 24 of the tear 12 together into juxtaposition (as shown in FIG. 11).

As described further below, the suture portion 10c and the suture portion 10d are tied together prior to implantation of the device 8 to form a limiting element in the form of a slip knot 28 that allows suture 10 to be pulled in the direction of arrow 32, but does not allow tension on suture 10 to pull suture 10 in the opposite direction, which would allow the tear 12 to reopen.

Figure 2B:
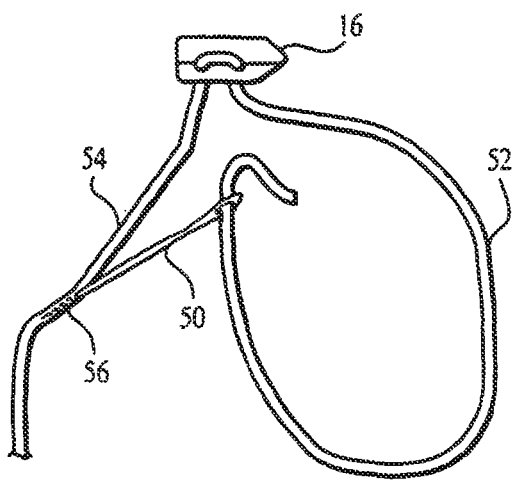
Figure 2C:
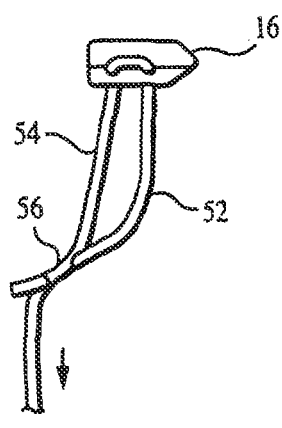
Figure 2D:
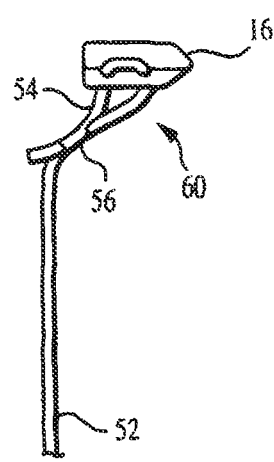

Referring to FIGS. 2A-2I, prior to insertion into tissue 14, suture 10 is attached to the fixation members 16, 18 and the slip knot 28 is formed. The fixation member 16 defines holes 16a, 16b for receiving suture 10, and the fixation member 18 defines holes 18a, 18b (shown in FIGS. 2E and 2F) for receiving suture 10. As illustrated in FIGS. 2A-2D, suture 10 is attached to the fixation member 16 by threading suture 10 through a needle 50, and passing the needle 50 and suture 10 through the holes 16a, 16b in the fixation member 16 (FIG. 2A). Suture 10 now defines a long suture section 52 and a short suture section 54. The long suture section 52 is then attached to the short suture section 54 by passing the needle 50 and the long suture section 52 through the short suture section 54 at a region 56 (FIG. 2B). Pulling the long suture section 52 away from the fixation member 16 (FIG. 2C) then draws the region 56 toward the fixation member 16 forming a knot 60 (FIG. 2D). Suture 10 is now secured to the fixation member 16.

Figure 2E:
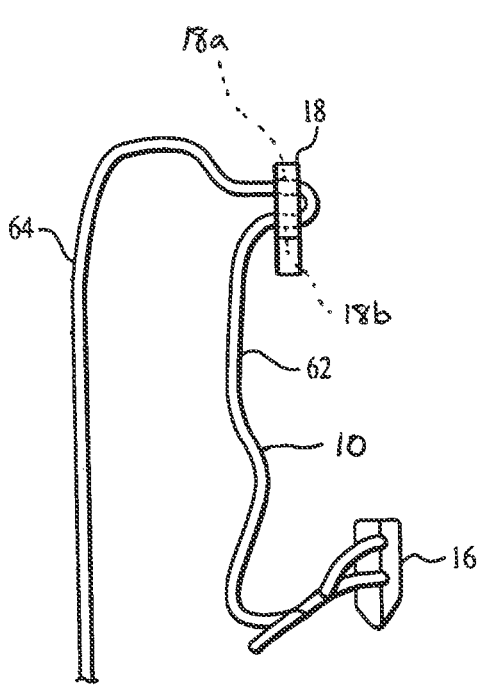
Figure 2F:
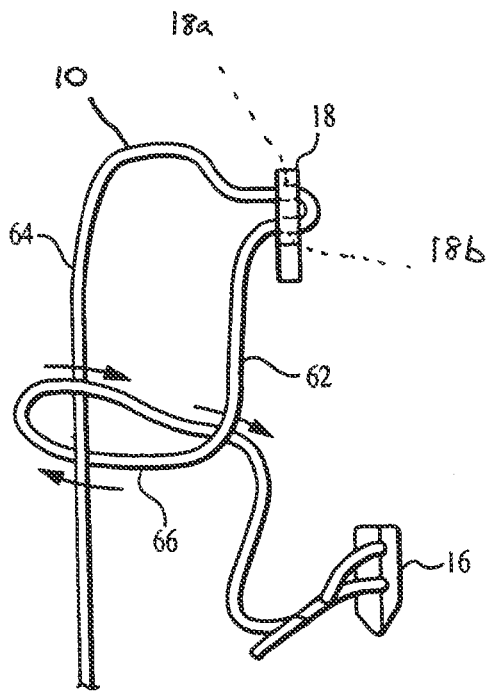
Figure 2G:
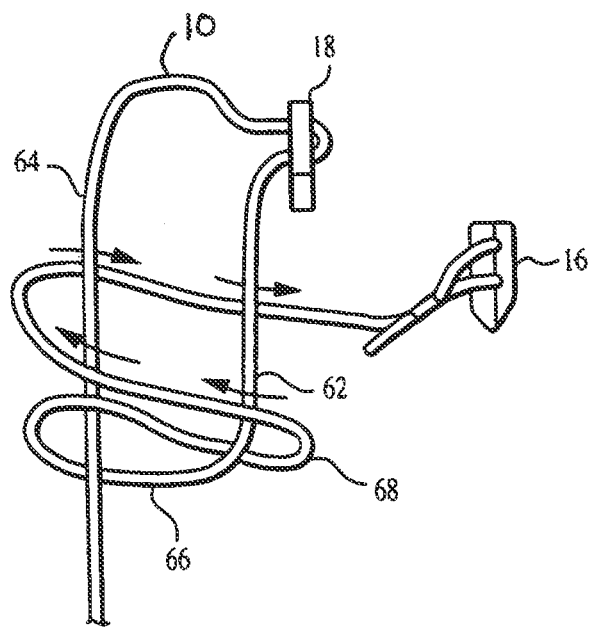
Figure 2H:
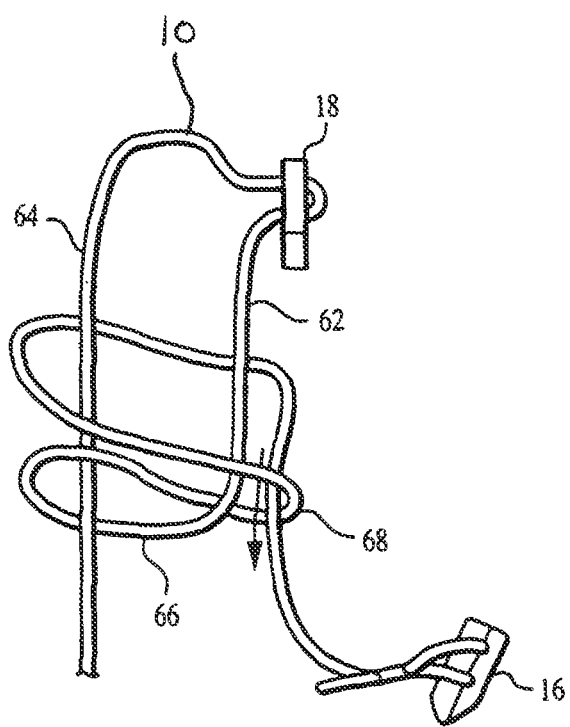
Figure 2I:
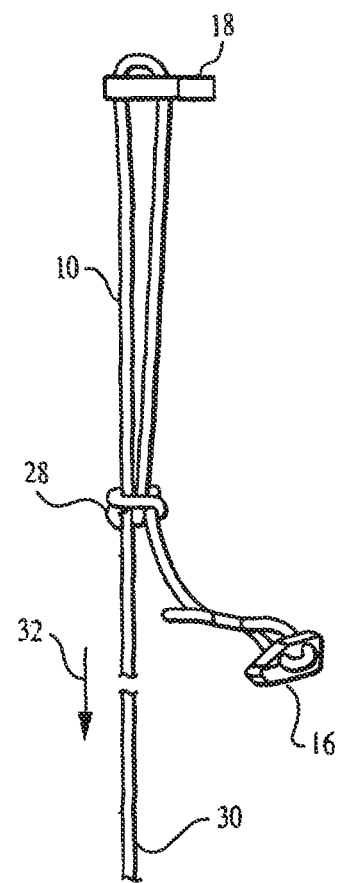

Referring to FIGS. 2E-2I, suture 10 is now attached to the fixation member 18 by passing the long suture section 52 through the holes 18a, 18b in the second fixation member 18 (FIG. 2E). The long suture section 52 now defines a first suture length 62 and a second suture length 64. The slip knot 28 (FIG. 2I) is formed by passing the fixation member 16 under the suture length 64, over the suture length 64, and under the suture length 62, forming a loop 66 (FIG. 2F); then passing the fixation member 16 over the suture lengths 62 and 64, forming a loop 68 (FIG. 2G); and then passing the fixation member 16 under the suture lengths 64 and 62 (FIG. 2G), and finally through the loop 68 (FIG. 2H). Pulling the fixation member 16 relative to the fixation member 18 tightens the slip knot 28 (FIG. 2I). Pulling the free end 30 of suture 10 now acts to slide suture 10 through the slip knot 28, while the slip knot 28 limits sliding of suture 10 in the opposite direction when suture 10 is under tension.

Referring to FIG. 3, a delivery device 99 for implanting the device 8 in tissue 14 includes a sheath 200 and a needle 100. The sheath 200 is preferably formed from plastic, and the needle 100 is preferably metal. The needle 100 has an open distal end 111 with a pointed, tissue piercing tip 108. The needle 100 has an inner surface 102, defining a lumen 104, and a slot 110, both the inner surface 102 and the slot 110 extending to the open distal end 111. The slot 110 extends from an outer surface 106 of the needle 100 to the lumen 104. As described further below, the needle 100 receives the fixation members 16 and 18 within the lumen 104 and the slot 110 with suture 10 tied to the fixation members 16, 18 as illustrated in FIGS. 2A-2I. The sheath 200 defines a lumen 202 that receives the needle 100 and the device 8 with suture 10 positioned between the needle 100 and the sheath 200 and extending through a hole 201 defined at a proximal end 203 of the sheath 200. The sheath 200 has a distal end 204 from which the needle 100 extends.

Referring also to FIGS. 4-4B, the slot 110 has a proximal, closed end 120 and a distal open end 140. The fixation members 16 and 18 (which are generally described in U.S. application Ser. No. 09/453,120, supra) have the same shape with each fixation member including a cylindrical region 151 received within the lumen 104 of the needle 100, and a fin 152 extending through the slot 110 with a portion 154 of the fin 152 extending beyond the outer surface 106 of the needle 100. The fixation member 16 is located at a distal region 112 of the slot 110, and the fixation member 18 is located at a proximal region 114 of the slot 110. The distal end 111 of the needle 100 is indented, for example, crimped at 150, and the inner surface 102 of the needle 100 has a protrusion extending into lumen 104, for example, a dimple 130, near the distal end 140. The dimple 130 and the crimp 150 are sized to resist unintentional passage of the fixation members either over the dimple 130 or through the open distal end 111, though only a small force on the fixation members is needed to overcome the resisting load applied to the fixation members by the crimp 150 and the dimple 130. As shown in FIG. 4A, the fixation members 16, 18 have sloped surfaces 152a that aid in passage through tissue, and flat surfaces 154a that aid in retention of the fixation members at their deployment sites.

During manufacturing, to position the fixation members 16, 18 in the needle 100, after suture 10 is attached to the fixation members 16, 18, the fixation member 18 is loaded in the needle 100 by passing the fixation member 18 through the distal end 111 and sliding the fixation member 18 along the lumen 104 and the slot 110 to the proximal end 120 of the slot 110. The fixation member 16 is then loaded in the needle 100 by passing the fixation member 16 through the distal end 111 and positioning the fixation member 16 in the region 112. The dimple 130 and the crimp 150 are then formed. The fixation member 16 is now restrained from unintentional movement in the proximal direction by the dimple 130 and in the distal direction by the crimp 150.

Alternatively, as shown in FIG. 4C, rather than dimple 130, a needle 100a includes a ramp 130a formed by making three slits in a wall 101 of the needle 100a and bending a section of the wall toward the inside of the needle 100a.

Figure 5:
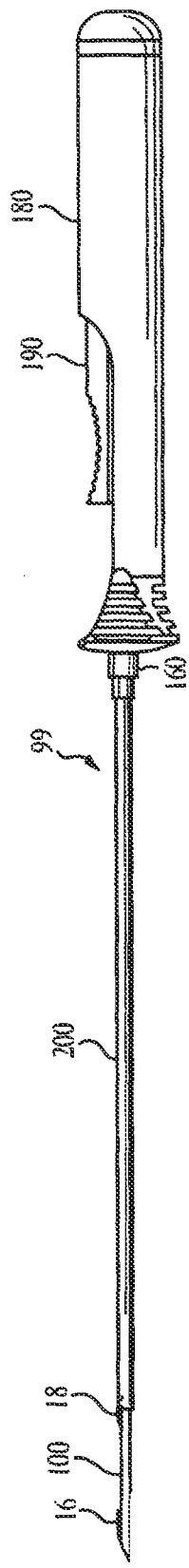
FIG. 5 is side view of the delivery device of FIG. 3.

Referring also to FIG. 5, the needle 100 has a proximal end 160 mounted to a handle 180. Located within the needle 100, proximal of the fixation member 18, is a push rod 170 (FIG. 4) used to advance the fixation member 18, as described below. The handle 180 includes an actuating slider 190 attached to the push rod 170 for advancing the push rod 170. Once the device 8 is secured to the needle 100, as described above, the sheath 200 is placed over the needle 100, with the majority of suture 10 located within and protected by the sheath 200. The sheath 200 also covers the majority of the fixation member 18 and helps keep the fixation member 18 in position. The sheath 200 is then secured to the handle 180 by an interference fit. The distance that the needle 100 extends from the sheath 200 determines the penetration depth of the needle 100 into the tissue. The delivery device 99 is supplied to the surgeon with the device 8 preloaded in the needle 100.

Figure 5A:
FIG. 5A is a side view of a variable length depth stop for use with the delivery device of FIG. 3.

Referring to FIG. 5A, an outer protective tube 200a can be placed over the sheath 200. The tube 200a protects the needle tip during shipping. If it is desired to supply the surgeon with a variable length depth stop, the tube 200a can be provided with gradations 201. The surgeon scores the tube 200a to provide the tube with the desired length for the surgical procedure. The tube 200a is coupled to the handle 180 by a loose interference fit to allow the surgeon to remove the tube 200a if the tube 200a is not being used during surgery.

Figure 5B:
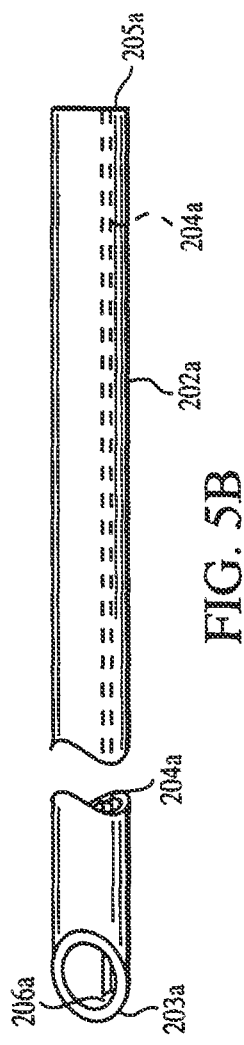
FIG. 5B is a perspective view of a cannula for use with the delivery device of FIG. 3.

Referring to FIG. 5B, to eliminate the need for placement of the delivery device 99 through an arthroscopy cannula, a removable cannula 202a, formed, for example, of a plastic material, can be placed over the sheath 200. The cannula 202a has a distal, tissue penetrating tip 203a and a slot 204a extending from a proximal end 205a of the cannula 202a to within about 0.02 inches of the distal tip 203a to define a distal region 206a. The slot 204a permits the removal of the cannula 202a from the delivery device 99 after placement of the delivery device in the joint. To remove the cannula 202a, the surgeon grasps the cannula and moves it laterally relative to the sheath 200, until the sheath 200 slides through the slot 204a. The surgeon then pulls the cannula 202a proximally, thus breaking the cannula region 206a and permitting complete removal of the cannula 202a.

Figure 8:
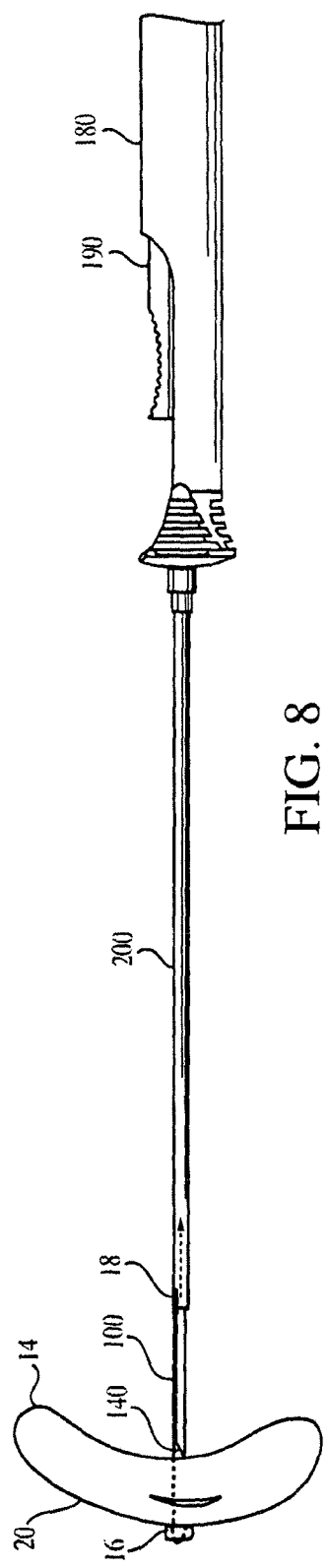

Referring to FIGS. 6-11, in use, preferably under arthroscopic guidance, the user inserts the delivery device 99 into, for example, the knee joint, and passes the needle 100 through soft tissue 14 and across the tear 12, until the needle tip 108 and the fixation member 16 extend through the tissue surface 20. The dimple 130 prevents the fixation member 16 from sliding proximally in response to forces acting on the fixation member 16 during insertion through tissue 14. The fixation member 16 is now positioned with the flat, tissue facing surface 154a of the portion 154 of the fin 152 extending beyond the needle surface 106 engaging the tissue surface 20 (FIG. 7). The user then pulls the delivery device 99 proximally removing the needle 100 from tissue 14 (FIG. 8). The force of the engagement of the fixation member 16 with the tissue surface 20 during removal of the needle 100 overcomes the retention force of the crimp 150. The fixation member 16 slides distally out of the open end 111 of the needle 100 and remains at the surface 20. During the retraction of the needle 100, a portion of suture 10 with the knot 28 is played out of the delivery device 99, with the suture 10 extending through soft tissue 14 across the tear 12.

Figure 9:
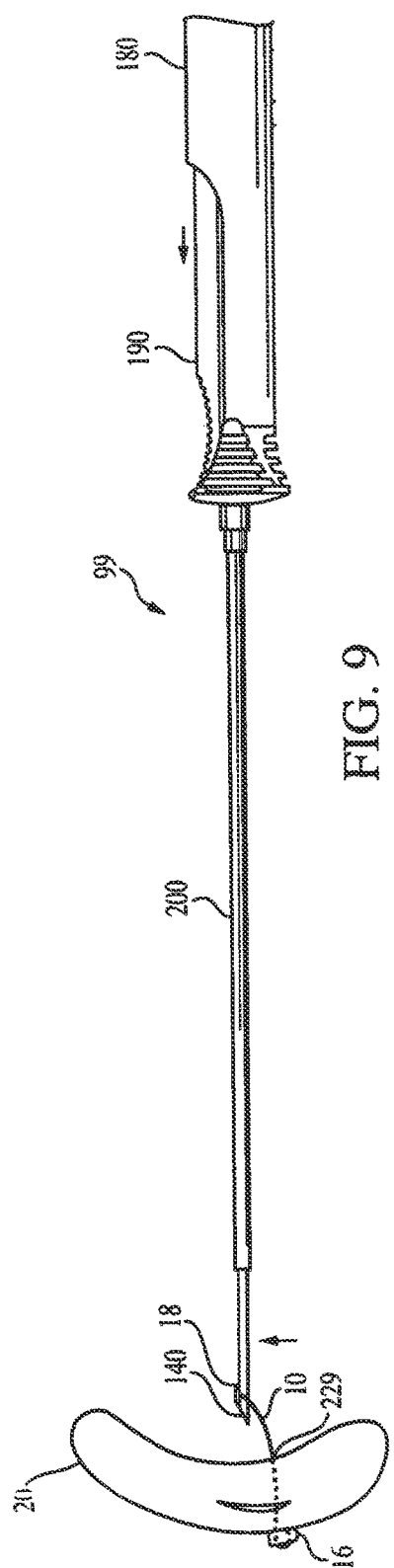
Figure 10:
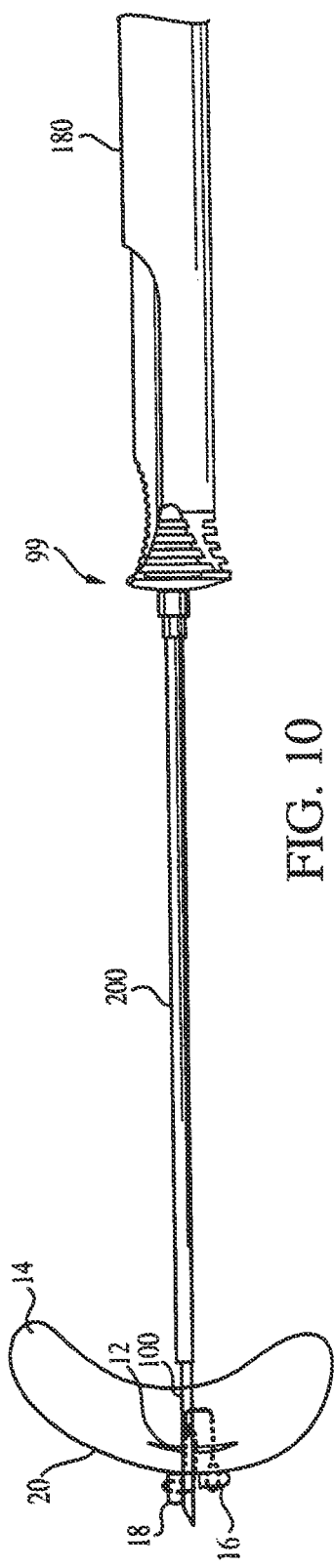

The user then advances the slider 190, advancing the rod 170 to push the fixation member 18 distally, over the dimple 130, to reside in the region 112 between the dimple 130 and the crimp 150 (FIG. 9). The user then moves the needle 100 to a spaced location to the side of and exit point 229 of suture 10 from tissue 14, and reinserts the needle 100 into soft tissue 14, across the tear 12, and through the surface 20, until the needle tip 108 and the fixation member 18 extend through tissue surface 20 (FIG. 10). The user then pulls the delivery device 99 proximally removing the needle 100 from tissue 14 (FIG. 11). The force of the engagement of the fixation member 18 with tissue surface 20 during removal of the needle 100 overcomes the retention force of the crimp 150 such that the fixation member 18 slides distally out of the open end 111 of the needle 100 and remains at surface 20, as described above with reference to the fixation member 16.

The free end 30 of suture 10 extends from the sheath 200, as shown in FIG. 11. The user grasps the free end 30 of suture 10 with forceps or by hand and pulls on the free end 30 of suture 10. This shortens the length of suture between the fixation members 16 and 18 (at suture portions 10a-10c), bringing the sides 22, 24 of the tear 12 into juxtaposition, as shown in FIG. 11. When the free end 30 of suture 10 is pulled, the slip knot 28 moves closer to the fixation member 18. Depending on the length of suture between the fixation members 16 and 18, the slip knot 28 is either on the tissue surface 26 or within tissue 14. The slip knot 28 allows suture 10 to slide in the direction of arrow 32, but does not allow suture 10 to slide in the opposite direction. The tension placed on suture 10 by pulling on the suture relative to the fixation members 16, 18, acts to turn the fixation members such that their long sides 255 are in contact with the tissue surface 20. Excess suture 10 can then be cut off. Further manipulation of suture 10 is not needed to secure the fixation members 16, 18, although the surgeon may wish to provide additional fastening as a back-up securement measure.

Figure 12:
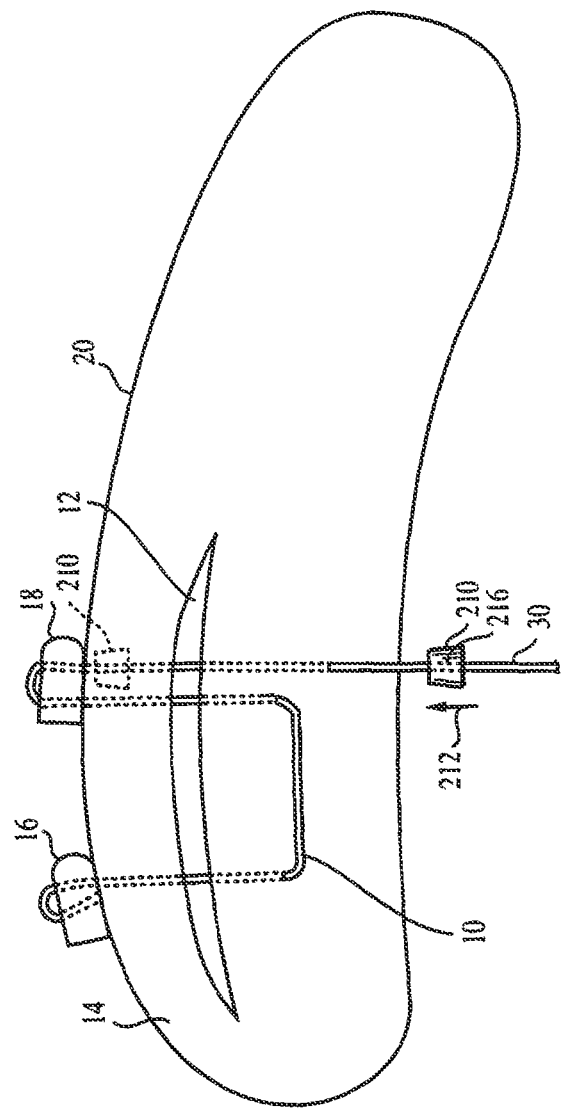
FIG. 12 is an illustration of the closure device of FIG. 1 with an alternative embodiment of a limiting element, shown mending a tear in soft tissue.

Referring to FIG. 12, rather than a slip knot 28 acting as a limiting element allowing suture 10 to be tightened while resisting loosening of suture 10, here, a separate limiting element 210 is positioned on the free end 30 of suture 10. While pulling on the free end 30, the surgeon advances the limiting element 210 through the tissue 14, in the direction of arrow 212, until the limiting element 210 is positioned against the fixation member 18, as shown in dashed line. This action acts to close tear 12 and secure the device 8 in place.

The limiting element 210 defines a through bore 216 for receiving suture 10. The material of the limiting element 210, for example, acetal, is selected, and the diameter of the through bore 216 is sized relative to suture 10 to provide the desired amount of friction between suture 10 and the limiting element 210 for adequate securement. Thus, the user can slide suture 10 in the direction of arrow 212, but adequate friction is provided between suture 10 and the limiting element 210 to limit sliding of the limiting element 210 in the opposite direction under normal loads in the knee joint.

Figure 12C:
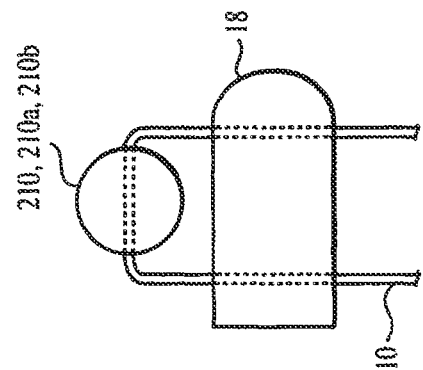
FIG. 12C shows the limiting element of FIG. 12 in an alternative position.
Figure 12B:
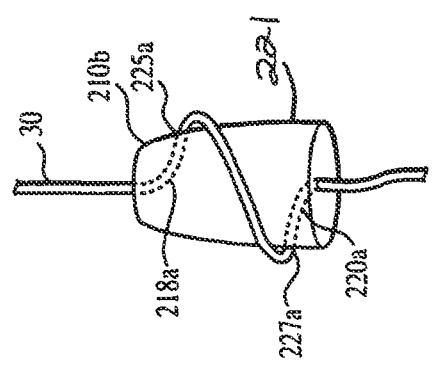
FIGS. 12A and 12B show alternative embodiments of the limiting element of FIG. 11.
Figure 12A:
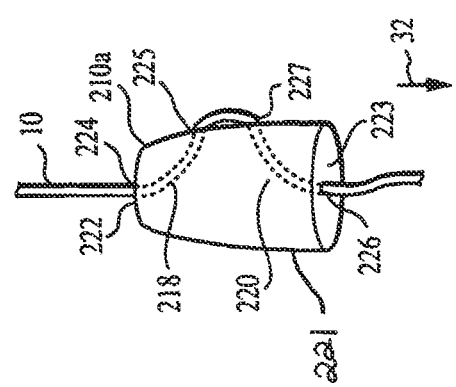

Referring to FIG. 12A, a limiting element 210a defines two angled channels 218, 220 for receiving the free end 30 of suture 10. The limiting element 210a has a generally cylindrical surface 221 and ends 222, 223. The channel 218 has a first opening 224 at end 222 and a second opening 225 on the surface 221. The channel 220 has a first opening 226 at end 223 and a second opening 227 on the same side of the surface 221 as the channel 218. Suture 10 follows a tortuous path through the channel 218, over the surface 221 between the openings 225 and 227, and then through the channel 220 with the free end 30 extending from the opening 226. The tortuous path aids in securement of the device 8.

In FIG. 12B, instead of the channel openings 224, 225 on the surface 221 being on the same side, a limiting element 210b defines two angled channels 218a, 220a each having a channel end 225a, 227a, respectively, on opposite sides of the surface 221. Suture 10 thus wraps part of the way around the element 210b to aid in securement of the device 8.

Referring to FIG. 12C, rather than positioning the limiting element on suture 10 after suture 10 exits from the fixation member 18, here, the limiting element 210, 210a, or 210b is positioned along suture 10 between the portions of suture 10 passing through the fixation member 18.

The limiting elements 210, 210a, 210b are slidably received on suture 10. In the embodiments of FIGS. 12-12B, the limiting element slides over suture 10, changing position relative to the fixation member 18, while in the embodiment of FIG. 12C, suture 10 slides within the limiting element with the position of the limiting element being relatively unchanged relative to the fixation member 18.

Referring to FIG. 13, the device 8 can be secured to tissue 14 using a limiting element such as a simple overhand knot 230. The knot 230 is first tied in the free end 30 of suture 10 and pushed, in the direction of arrow 240, through tissue 14 and against the fixation member 18, as shown in dashed line. Referring to FIGS. 13A and 13B, the knot 230 includes three crossing points, labeled, 230a, 230b, and 230c. When under tension, T, the knot 230 tends to tighten upon itself, rather than slide in the direction of arrow 240 making it difficult to advance the knot 230 along suture 10. To enable tension, T, to be applied to suture 10 at the same time that the knot 230 is advanced in the direction of arrow 240, a knot pusher 250 is used. The knot pusher 250 is configured to keep suture at crossing points 230a, 230b, and 230c from touching, such that the knot 230 does not tighten upon itself under tension, T. This permits the knot 230 to slide along the tensioned suture when the knot pusher 250 is advanced in the direction of arrow 240.

The knot pusher 250 has a cylindrical body 252 and an end post 254. The body 252 defines a first groove 254 and a second groove 256 on one surface, and a third groove 258 that is an extension of groove 256 on an opposite surface. The grooves 254 and 256 form an X pattern, and the grooves 256 and 258 define a loop 260 extending around the body 252. The three grooves differ in depth, with the groove 256 being the shallowest and the groove 258 being the deepest. Thus, when suture 10 is formed into an overhand knot and positioned within the grooves 254, 256, and 258, the suture at crossing points 230a, 230b, and 230c does not touch. Once the knot 230 is advanced against the fixation member 18, the knot pusher 250 is removed by pulling retrograde on the knot pusher. To aid in removal of the knot pusher 250, a tube (not shown) can be advanced over the knot pusher 250 between the knot pusher and the suture. As the tube is advanced past suture crossing point 230a, the suture is stripped from the knot pusher 250.

Figure 14:
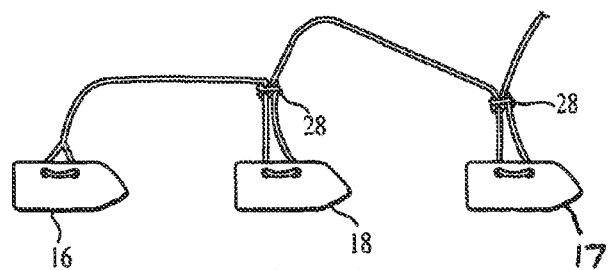
FIG. 14 is an illustration of an alternative embodiment of a closure device.

Referring to FIG. 14, one or more additional fixation members 17 with a slip knot 28 formed in suture 10 can be added to the device 8. In use, the fixation members 16 and 18 are implanted as described above, with suture 10 being tightened to secure the fixation members 16 and 18 in place. The additional fixation member 17 is then implanted and suture 10 tightened to secure the fixation member 17 in place. To accommodate the additional fixation members, the slot 110 in the needle 100 of the delivery device 99 is extended. To permit access to the fixation member 18 by the push rod 170, the additional fixation members 17 preferably include a through bore (not shown) for passage therethrough by the push rod 170. The push rod 170 preferably is biased off angle such that when the push rod 170 is pulled out of the passage in the fixation member 17, the push rod is no longer aligned with the passage. Subsequent advancement of the push rod 170 then engages an end face of the fixation member 17 to push the fixation member 17 toward the tip of the needle 100, rather than back through the passage. The slider 190 is preferably spring loaded such that after the fixation member 18 is pushed out of the needle 100, the push rod 170 springs back to engage the next fixation member 17.

Figure 14A:
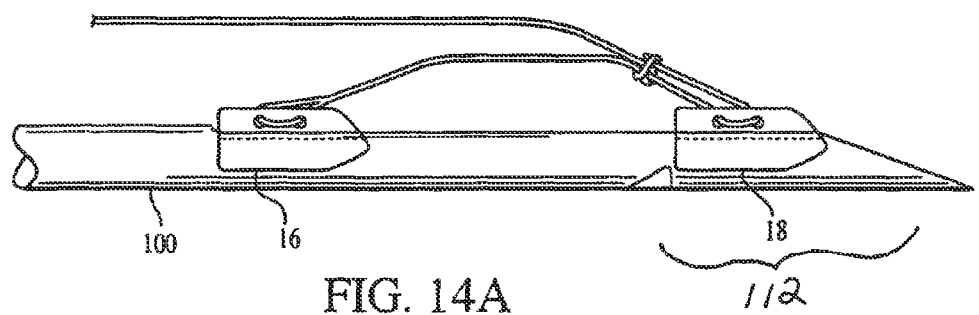
FIG. 14A shows an alternative arrangement of the closure device and delivery device of FIG. 14.
Figure 14B:
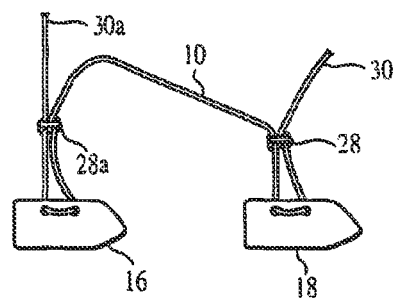
FIG. 14B is an illustration of an alternative embodiment of a closure device.

Referring to FIG. 14A, the positions of the fixation members 16 and 18 in the needle 100 can be swapped, with the fixation member 18 located in the distal region 112 such that the fixation member 18 is implanted in the tissue prior to implantation of the fixation member 16. Referring to FIG. 14B, rather than suture 10 being fixed to the fixation member 16, here suture 10 is attached to the fixation member 16 the same as the attachment to the fixation member 18, such that a second slip knot 28a is formed and a second free end 30a of suture extends from the fixation member 16. To secure the fixation members 16 and 18, both ends 30 and 30a of suture 10 are pulled.

Referring to FIGS. 15A-15C, a wound closure device 1010 includes a first fixation member, for example, a first retainer 1012, a second fixation member, for example, a second retainer 1014, and a flexible member, for example, suture 1016. Suture 1016 connects the first retainer 1012 to the second retainer 1014. Suture 1016 is tied to the first retainer 1012 with a conventional knot, but movably attached to the second retainer 1014, allowing a surgeon to shorten the length of suture between the retainers 1012 and 1014, and thereby close a wound. The first retainer 1012 has a generally solid cylindrical body 1018 extending axially from a distal surface 1019a to a flat proximal surface 1019b. To facilitate passage of the first retainer 1012 into tissue, both an upper portion 1022a and a lower portion 1022b of the surface 1019a are beveled relative to the axis of the cylindrical body 1018, forming a rounded distal tip 1022c. The upper portion 1022a is beveled at an angle a relative to the axis of the cylindrical body 1018, and the lower portion 1022b is beveled at an angle b relative to the axis.

Attached to the cylindrical body 1018 is a fin-shaped projection 1020 that extends from the upper portion 1022a of the distal surface 1019a to the proximal surface 1019b. The fin 1020 defines two horizontally transverse holes, 1024a and 1024b. Suture 1016 is attached to the first retainer 1012 by passing the suture through a hole 1024a in a first direction (for example, out of the page in FIG. 15A), through a hole 1024b in a second direction (for example, into the page in FIG. 15A), and then forming a conventional knot 1025 near the fin 1020. The conventional knot 1025 rigidly fixes suture 1016 to the first retainer 1012.

The second retainer 1014 has a distal surface 1029a, a proximal surface 1029b, and a generally cylindrical body 1028 extending axially from the surface 1029a to the surface 1029b. Attached to the body 1028 is an appendage 1026. The appendage 1026 is generally L-shaped in cross-section, and extends along an axial length of the body 1028, from the surface 1029a to the surface 1029b.

The distal surface 1029a of the second retainer 1014 is beveled in a manner similar to the first retainer 1012: an upper portion 1031a of the surface 1029a forms an angle q relative to an axis of the body 1028, and a lower portion 1031b of the surface 1029a forms an angle f relative to the body's axis, forming a rounded distal tip 1031c. The proximal surface 1029b of the second retainer 1014 is flat.

The L-shape of the appendage 1026 is formed by two perpendicular sections: a stem 1036 attached to the cylindrical body 1028 along an axial length of the body, and a base 1032 attached to the stem. The base 1032 defines a vertically transverse hole 1030, and the stem 1036 defines two horizontally transverse holes 1034a and 1034b. The holes 1034a and 1034b are perpendicular to the hole 1030, but all three holes pass through the second retainer 1014 in a direction generally parallel to the sides 1029a and 1029b.

Each of the three holes 1034a, 1034b, and 1030 connects the exterior of the second retainer 1014 to an interior, partially enclosed, protected region 1039. The region 1039 is defined by the base 1032, an interior surface 1037 of the stem 1036, and a concave groove 1035 within the cylindrical body 1028. The groove 1035 extends axially across the body 1028, along the line where the interior surface 1037 connects to the body 1028.

Suture 1016 is movably attached to the second retainer 1014 with a limiting element such as a one-way knot 1040. The one-way knot 1040 includes a first portion of suture 1016 that forms a loop 1042, and a second portion of suture that passes around the body 1028 and through the loop 1042. The loop 1042 is formed within the protective region 1039 defined by the groove 1035, the surface 1037, and the base 1032. The region 1039 acts to separate the loop 1042 from tissue when the device 1010 is implanted within tissue, preventing the tissue from interfering with the sliding action of the one-way knot 1040.

To form the one-way knot 1040, suture 1016 is first passed from an exterior of the second retainer 1014, through the hole 1034a into the region 1039, and then back out the hole 1034b to the exterior, forming the loop 1042 within the region 1039. The suture is then passed over the rounded, exterior surface 1041 of the cylindrical body 1028, back into the region 1039, through the loop 1042, and then to the exterior through the hole 1030. Suture 1016 terminates at a free end 1044.

The one-way knot 1040 allows the length of suture between the first retainer 1012 and the second retainer 1014 to be shortened, but not lengthened. A surgeon can shorten the length of suture between the retainers 1012 and 1014 by pulling on the free end 1044, which draws additional suture in the direction of the arrows in FIG. 15A, through the holes 1030, 1034b, and 1034a, thereby reducing the length of suture between the retainers 1012 and 1014. If, however, the surgeon attempts to lengthen the distance between the retainers, for example, by pulling the first retainer 1012 away from the second retainer 1014 (that is, pulling suture 1016 in the opposite direction of the arrows), then the loop 1042 squeezes the portion 1046 of suture 1016 against an interior compression surface 1043 of the stem 1036, preventing further lengthening of the distance between the retainers.

If suture 1016 is a braided suture, as opposed to a smooth suture, then suture 1016 should be threaded through the second retainer 1014 in a particular direction. Referring to FIG. 15D, a braided suture 1016a is formed from numerous threads 1017a braided from left to right in FIG. 15D. Braided suture 1016a slides more easily if it is pulled in the direction of braiding (that is, in the direction of arrow S in FIG. 15D) than if it is pulled against the braiding (that is, in the direction of arrow L in FIG. 15D). Thus, if suture 1016 is a braided suture, then suture 1016 should be threaded through the second retainer 1014 in the direction of braiding. If threaded in the direction of braiding, the suture will slide more easily in the direction of the arrows in FIG. 15A, and less easily in the direction opposing the arrows.

The cylindrical portions of the retainers 1012 and 1014 are sized and shaped to fit within a hollow bore of a needle (described below), facilitating arthroscopic implantation of the device 1010. For example, the cylindrical body 1018 has a diameter D1 of about 0.04 inches, and the cylindrical body 1028 has a diameter D2 approximately equal to diameter D1. The fin-shaped projection 1020 and the L-shaped appendage 1026, however, are configured to protrude through a longitudinal slit in the needle. Delivery of the device 1010 using a hollow needle is described below, with reference to FIGS. 19A-19D and 20A-20D.

The first retainer 1012 has an overall axial length L1 of, for example, about 0.19 inches, and the fin 1020 has a height H1 of, for example, about 0.03 inches. The second retainer 1014 has an overall axial length L2 of, for example, about 0.22 inches, a width W2 of, for example, about 0.06 inches, and a height H2 of, for example, about 0.07 inches. Angle a is, for example, about 30 degrees, angle b is, for example, about 40 degrees, angle q is, for example, about 30 degrees, and angle f is, for example, about 40 degrees.

The retainers 1012 and 1014 are made from rigid, biocompatible materials, such as polyethylene, an acetal, or polypropylene. Alternatively, the retainers 1012 and 1014 can be made from resiliently deformable materials, as described in Hayhurst, supra, or from bioabsorbable materials. The retainers 1012 and 1014 are preferably unitary, injection molded pieces, but can also be manufactured by other methods.

FIG. 16 illustrates the use of the wound closure device 1010 to repair a torn meniscus 1050. The meniscus 1050 has a tear 1052 that unnaturally separates distal meniscal tissue 1054 from proximal meniscal tissue 1056. A width WM of the meniscus 1050, as measured from points 1060a and 1060b to an exterior surface 1058 of the meniscus is, for example, about 0.25 inches.

When the device 1010 is implanted within the meniscus 1050, both the retainers 1012 and 1014 abut the surface 1058, separated by a distance of, for example, about 1 cm. Suture 1016 passes from the first retainer 1012, into distal tissue 1054, across tear 1052, and emerges from proximal tissue 1056 at point 1060a. Suture 1016 then passes again into proximal tissue 1056 at point 1060b, again traverses tear 1052, and emerges out at surface 1058, where it attaches to the second retainer 1014 by means of the one-way knot 1040. From the second retainer 1014, suture 1016 passes again into distal tissue 1054, traverses tear 1052, and emerges from proximal tissue 1056 at or near point 1060b. The free end 1044 of suture 1016 emerges from proximal tissue 1056.

Referring to FIGS. 16, 17A, and 17B, once the device 1010 is implanted, a surgeon can close tear 1052 by pulling on the free end 1044 of suture 1016. When the surgeon pulls on the free end 1044, four separate movements occur in succession. First, friction between suture 1016 and the body 1028 rotates the second retainer 1014 until a lower surface 1033 of the base 1032 is flush against meniscal surface 1058, as shown in FIG. 17A. Second, tension in suture 1016 pulls the center of the fin 1020 towards surface 1058, causing the first retainer 1012 to align against surface 1058 transversely to the portion of suture 1016 that exits the first retainer 1012, with both the fin 1020 and the axial length of the body 1018 pressing against the meniscal surface 1058. Third, continued pulling on the free end 1044 draws additional suture through the holes 1030, 1034b, and 1034a, by means of the knot 1040, in the direction of the arrows of FIG. 15A, lengthening the free end 1044 and shortening the length of suture between the retainers 1012 and 1014. Shortening the length of suture between the retainers 1012 and 1014 increases the tension in suture 1016 between the retainers, which pulls distal tissue 1054 and proximal tissue 1056 together, closing tear 1052. Since the loop 1042 remains within the protected region 1039 as the surgeon pulls on the free end 1044, the base 1032 separates the loop 1042 from tissue, and suture 1016 does not become wedged between tissue and the second retainer 1014 when the surgeon pulls on the suture's free end. Once tear 1052 has been closed, the one-way knot 1040 prevents the two retainers from pulling apart, and prevents the tear from reopening.

The final successive movement occurs when the surgeon releases the free end 1044, after closing tear 1052. When the surgeon releases the free end, the tension in suture 1016 between the two retainers pulls the body 1028 of the second retainer 1014 away from the free end 1044, causing the second retainer 1014 to rotate in the direction of arrow R (FIG. 17B), until the body 1028 abuts the meniscal surface 1058, trapping a portion 1062 of suture 1016 between the body 1028 and the surface 1058. (For clarity, suture 1016 is shown spaced slightly from the body 1028 and the stem 1036 in FIG. 17B. In actuality, suture 1016 is flush against the surfaces of the second retainer 1014 after suture 1016 is tensioned by the surgeon.)

When the second retainer 1014 is in its final position, as shown in FIG. 17B, suture 1016 is locked in place. The length of suture between the retainers 1012 and 1014 cannot be increased, because the loop 1042 of the one-way knot 1040 presses the portion 1046 of the suture against the surface 1043 of the stem 1036. In addition, the length of suture between the retainers resists being further shortened, since the portion 1062 of suture 1016 is wedged between the body 1028 and the surface 1058 of the meniscus.

Figure 18:
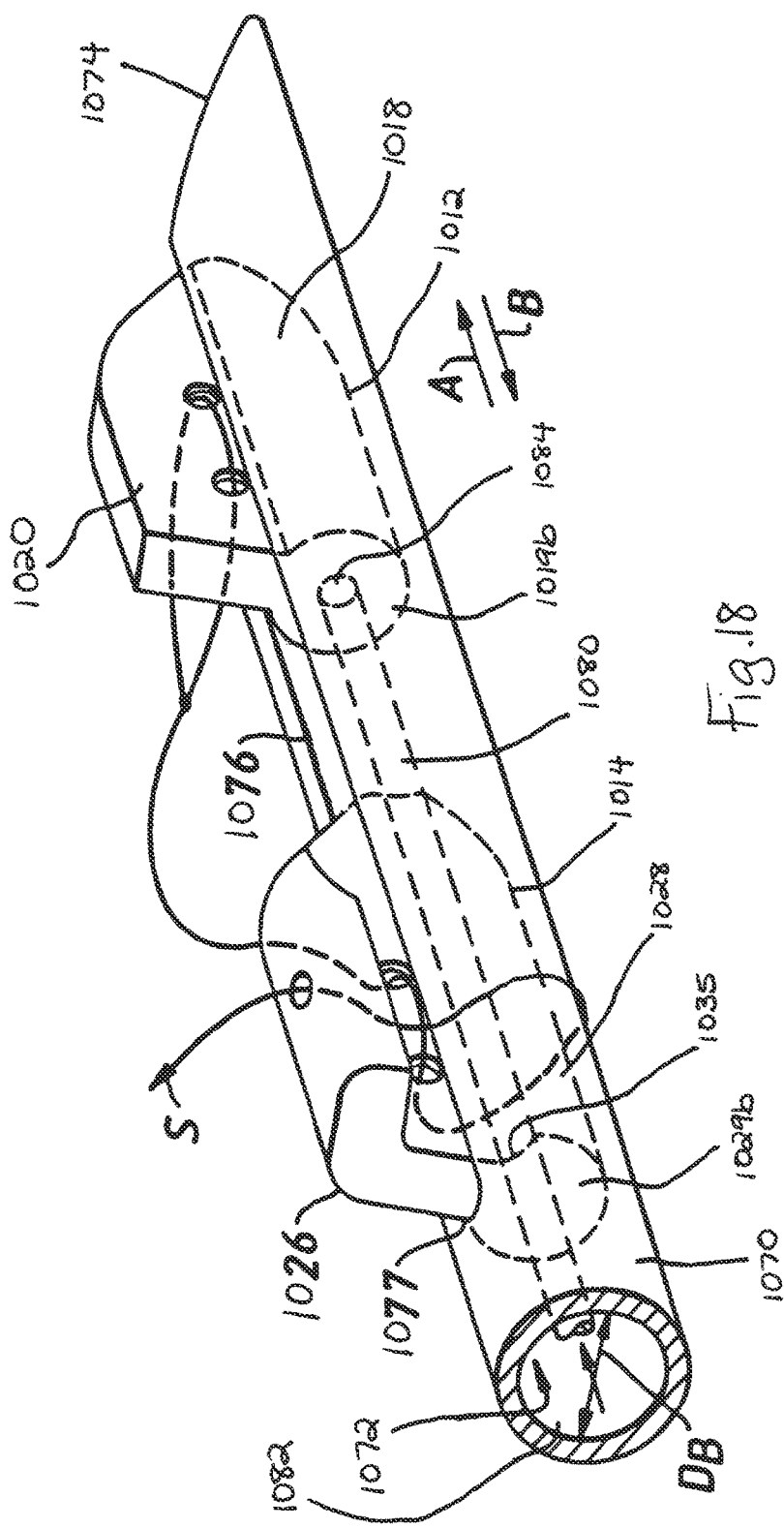
FIG. 18 is a perspective view of a hollow needle, with the wound closure device of FIG. 15A disposed within a bore of the needle.

The wound closure device 1010 is preferably deployed within meniscus 1050 arthroscopically, using a hollow needle 1070. Referring to FIG. 18, the hollow needle 1070 defines a bore 1072 and an open distal tip 1074. The diameter DB of the bore 1072 is slightly larger than the diameter D1 of the body 1018 of the first retainer 1012, and the diameter D2 of the body 1028 of the second retainer 1014, allowing the body 1018 and the body 1028 to fit slidably within the bore. The needle 1070 also includes a longitudinal slit 1076 through a wall of the needle. The slit 1076 extends proximally from the open tip 1074, and communicates with the bore 1072. The slit 1076 is sized and shaped to allow the fin 1020 of the first retainer 1012 and the L-shaped appendage 1026 of the second retainer 1014 to protrude from the needle 1070.

The needle 1070 also includes a plunger 1080. The plunger 1080 enters the bore 1072 through a proximal opening 1082 in the needle 1070, and extends to the proximal surface 1019b of the first retainer 1012. The plunger 1080 passes by the second retainer 1014 by sliding along the groove 1035. When the plunger 1080 is positioned as shown in FIG. 18, sliding the plunger 1080 in the direction of arrow A pushes the first retainer 1012 distally, but does not move the second retainer 1014.

Prior to surgery, suture 1016 is attached to the retainers 1012 and 1014, in the manner described above with reference to FIG. 15A. The two retainers 1012 and 1014 are then loaded into the bore 1072 of the needle 1070. The second retainer 1014 is loaded first, by inserting the cylindrical head 1028 into the bore 1072, through the open tip 1074, such that the appendage 1026 protrudes through the slit 1076. The second retainer 1014 is pushed proximally into the slit 1076, until the stem 1036 abuts a proximal surface 1077 of the slit. Next, the first retainer 1012 is loaded into the distal most position in the needle 1070 by inserting the cylindrical body 1018 through the tip 1074, into the bore 1072, such that the fin 1020 protrudes through the slit 1076. Both the retainers 1012 and 1014 are loaded with their respective beveled distal surfaces 1019a and 1029a facing the open distal tip 1074.

After the retainers have been loaded, the plunger 1080 is inserted into the bore 1072 through the proximal opening 1082. The plunger 1080 is slid past the second retainer 1014 along the groove 1035, until a tip 1084 of the plunger abuts the proximal surface 1019b of the first retainer 1012.

Attachment of suture 1016 to the retainers 1012 and 1014 and loading of the retainers and the plunger into the needle 1070 can be performed at the time of manufacture, that is, pre-loaded, or immediately prior to surgery.

During surgery (or prior to surgery), the surgeon first pushes the plunger 1080 in the direction of arrow A to separate the retainers 1012 and 1014 within the bore 1072. The surgeon pushes the plunger until the retainers are separated by at least a distance L, as shown in FIG. 18, where L is greater than width WM of meniscus 1050. Distance L is, for example, about 0.35 inches.

Referring to FIGS. 16 and 19A-19D (not to scale), the surgeon next pushes the needle 1070 through meniscus 1050, in the direction of arrow A, until the fin 1020 of the first retainer 1012 passes entirely through the exterior surface 1058 of the meniscus. As the surgeon pushes the needle 1070 through the tissue, he or she holds the plunger 1080 steady, to prevent the first retainer 1012 from sliding in the direction of arrow B as the needle is pushed through the meniscal tissue. Since the separation distance L is greater than the width WM of meniscus 1050, the second retainer 1014 does not enter the meniscus at this point in the procedure.

The surgeon next forces the first retainer 1012 out of the needle 1070 through the tip 1074 by pushing the plunger 1080 in the direction of arrow A, and then seats the retainer 1012 against the surface 1058 of the meniscus by pulling on the free end 1044 of suture 1016. Once the first retainer 1012 has been seated, the needle 1070 is pulled in the direction of arrow B, back through meniscus 1050, across tear 1052, and out the hole at the point 1060a (FIG. 19B).

The surgeon then reinserts the needle 1070 into meniscus 1050 at the point 1060b, and again passes the needle through the meniscus in the direction of arrow A, across tear 1052, until the tip 1074 passes through surface 1058. To eject the second retainer 1014, the surgeon withdraws the plunger 1080 in the direction of arrow B until the tip 1084 of the plunger is proximal to the surface 1029b of the second retainer 1014. The surgeon then maneuvers the plunger 1080 until the tip 1084 contacts the surface 1029b, and then pushes the plunger in the direction of arrow A, forcing the second retainer 1014 through the tip 1074. The plunger 1080 and the needle 1070 are then fully withdrawn in the direction of arrow B, leaving both the retainers 1012 and 1014 resting against surface 1058, as shown in FIG. 19D. The surgeon can then tension suture 1016, positioning the retainers against the surface 1058 and closing tear 1052, by pulling on the free end 1044, as described above with reference to FIG. 16.

Alternative deployment methods are possible. For example, the device 1010 can be extracted from the needle 1070 by engaging the fin 1020 with the surface 1058, rather than by using a plunger 1080. Referring to FIGS. 20A-20D (not to scale), in this embodiment, the plunger 1080 is not passed through the groove 1035 to the first retainer 1012. Instead, the tip 1084 of the plunger 1080 always remains proximal to the second retainer 1014.

When the two retainers are loaded into the bore 1072 of the needle 1070, a spacer 1086 is placed between the retainers. The spacer 1086 is a simple cylindrical bar, preferably made from a material that degrades quickly in the body, such as salt. The spacer 1086 has a longitudinal length LS greater than a width WM of meniscus 1050. Length LS is, for example, about 0.35 inches.

During surgery, the surgeon first pushes the needle 1070 through meniscus 1050, in the direction of arrow A, until the fin 1020 passes entirely through the exterior surface 1058 of the meniscus (FIG. 20A). As the surgeon pushes the needle 1070 through the tissue, the surface 1077 of the slit 1076 engages the stem 1036 of the second retainer 1014, preventing the two retainers and the spacer from sliding in the direction of arrow B within the bore 1072. (In addition, the surgeon can hold the plunger 1080 steady to prevent the two retainers from sliding in the direction of arrow B.)

The surgeon next pulls the needle in the direction of arrow B, back through meniscus 1050, across tear 1052, and out the hole at point 1060a (FIG. 20B). As the surgeon withdraws the needle, the fin 1020 engages the surface 1058, and the first retainer 1012 is pulled out of the needle 1070, through the tip 1074. As before, the surgeon then seats the first retainer 1012 against the surface 1058 by pulling on the free end 1044 of suture 1016. Since the spacer 1086 is larger than the width WM of meniscus 1050, the spacer prevents the second retainer 1014 from entering meniscus 1050, and therefore prevents the second retainer 1014 from also being pulled out of the needle 1070 as the needle 1070 is pulled in the direction of arrow B.

Next, the surgeon reinserts the needle 1070 into meniscus 1050 at point 1060b, and again passes the needle through the meniscus in the direction of arrow A, across tear 1052, until the tip 1074 passes through surface 1058. The surgeon then pushes the plunger 1080 in the direction of arrow A, ejecting both the spacer 1086 and the second retainer 1014 out of the needle 1070 through the tip 1074 (FIG. 20C). The needle is then fully withdrawn from meniscus 1050, in the direction of arrow B, leaving both the retainers 1012 and 1014 resting against the surface 1058, as shown in FIG. 20D. The surgeon then pulls on the free end 1044 to position the retainers and close the tear, as described above. The spacer 1086 can either be removed by the surgeon, or left within the body to degrade.

Figure 21A:
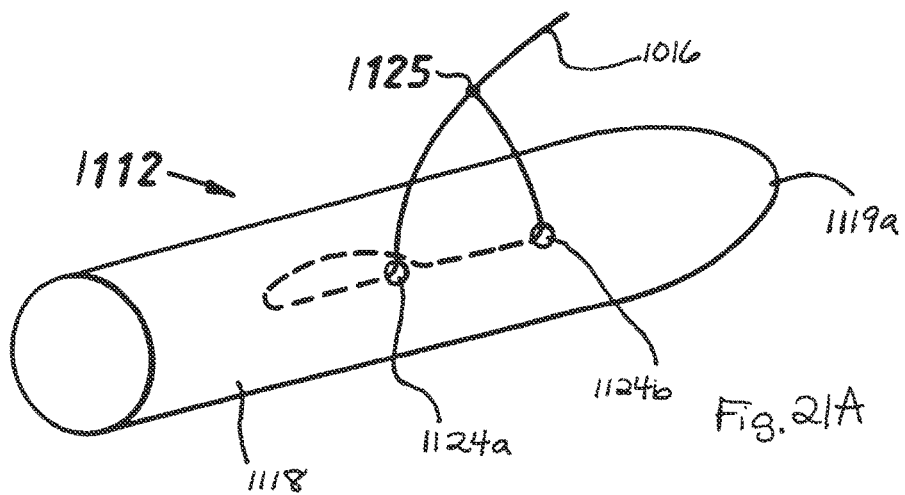
FIG. 21A is a perspective view of an alternative first fixation member design for a wound closure device, used in reverse deployment of the device.

In another alternative deployment method, a modified wound closure device is deployed in meniscus 1050 in reverse, with the second retainer being deployed first. Referring to FIG. 21A, a modified wound closure device includes a first retainer 1112 that has a beveled face 1119a, but lacks a fin. The first retainer 1112 has an axial, generally cylindrical body 1118 that defines two transverse holes 1124a and 1124b. Suture 1016 is attached to the first retainer 1112 by threading the suture through the hole 1124a in a first direction, through the hole 1124b in a second direction, and then tying a conventional knot 1125.

Referring to FIGS. 21B-21E (not to scale), in this reverse deployment embodiment, the second retainer 1014 is positioned distally in the bore 1072, with the first retainer 1112 directly proximal. The tip 1084 of the plunger 1080 resides immediately proximal to the first retainer 1112 in the bore 1072. In operation, the surgeon first pushes the needle 1070 through meniscus 1050, in the direction of arrow A, until the tip 1074 passes through the surface 1058. The surgeon then pushes the plunger 1080 in the direction of arrow A far enough to force the second retainer 1014 through the tip 1074, but not far enough to eject the first retainer 1112.

Figure 21B:
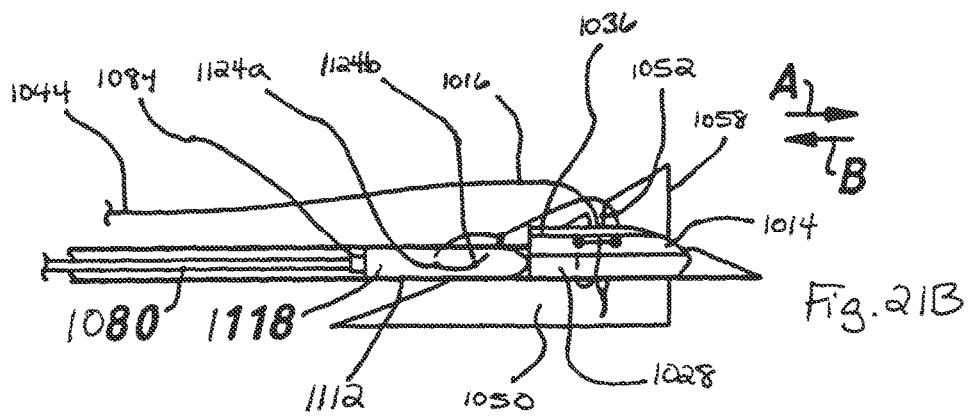
FIGS. 21B-21E are schematics illustrating reverse deployment of a wound closure device.
Figure 21C:
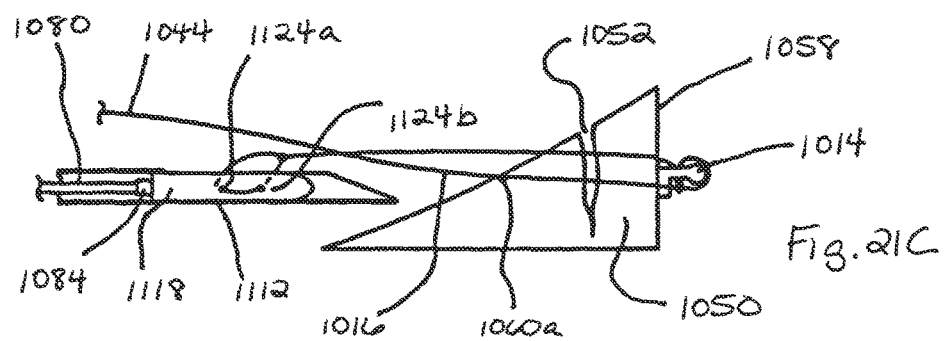
Figure 21D:
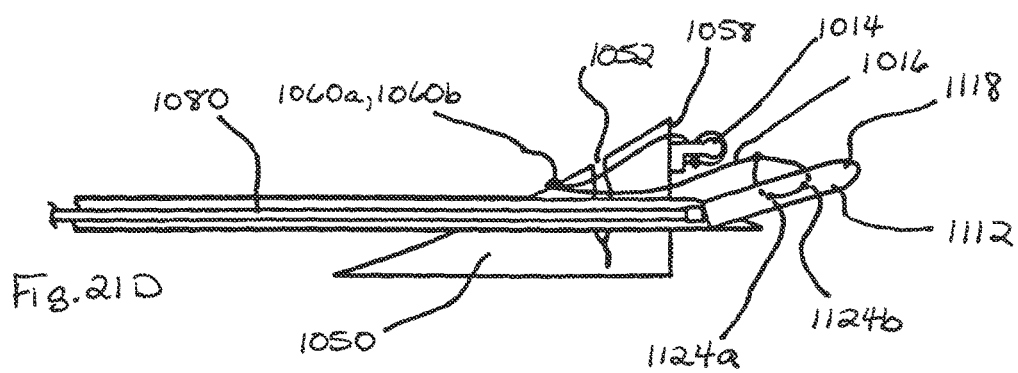
Figure 21E:
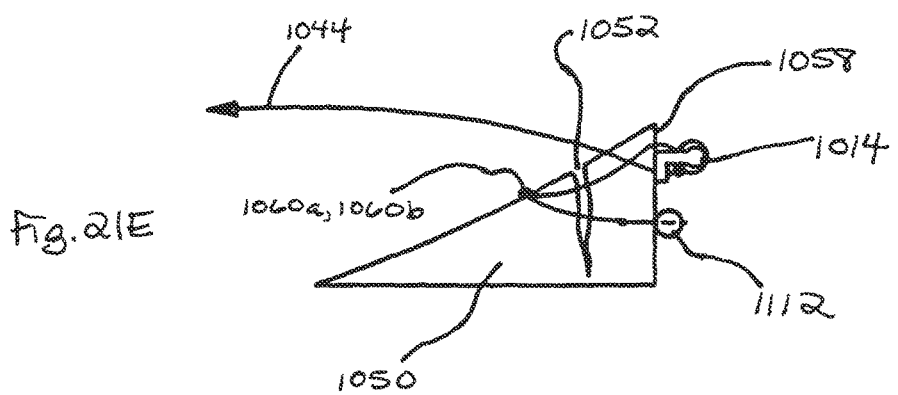

After the second retainer 1014 has been ejected, the surgeon pulls the needle in the direction of arrow B, back through meniscus 1050, across tear 1052, and out point 1060a (FIG. 21C). Since the first retainer 1112 does not include a fin, it does not protrude through the slit 1076, and does not engage tissue when the needle is pulled in the direction of arrow B. Next, the surgeon reinserts the needle 1070 into the meniscus at point 1060b, and again passes the needle through meniscus 1050 in the direction of arrow A, across tear 1052, until the tip 1074 passes through the surface 1058. The surgeon then ejects the first retainer 1112 by pushing the plunger 1080 in the direction of arrow A, (FIG. 21D), and withdraws the needle 1070 from meniscus 1050. The surgeon then positions the retainers and closes the tear 1052 by pulling on the free end 1044 (FIG. 21E), as described above.

Alternative configurations of the second retainer 1014 and the one-way knot 1040 are possible.

Figure 22A:
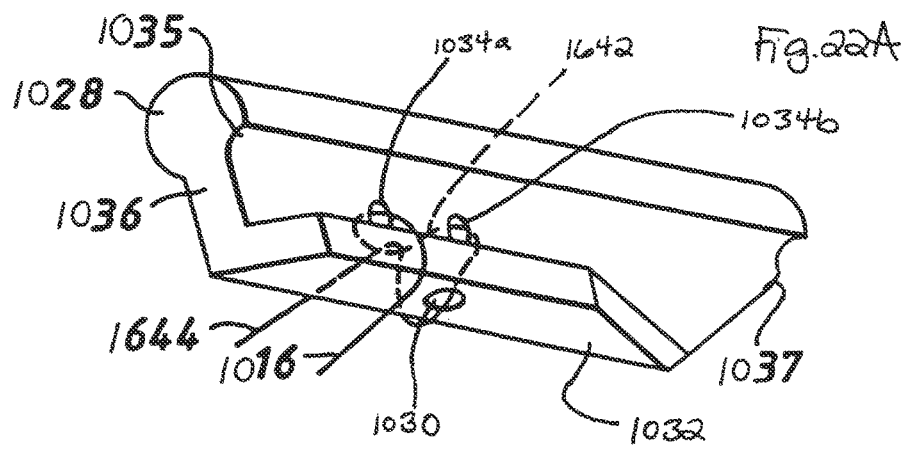
FIGS. 22A and 22B are perspective views of the second fixation member of FIGS. 15A and 15C, showing an alternative one-way knot configuration for the fixation member.
Figure 22B:
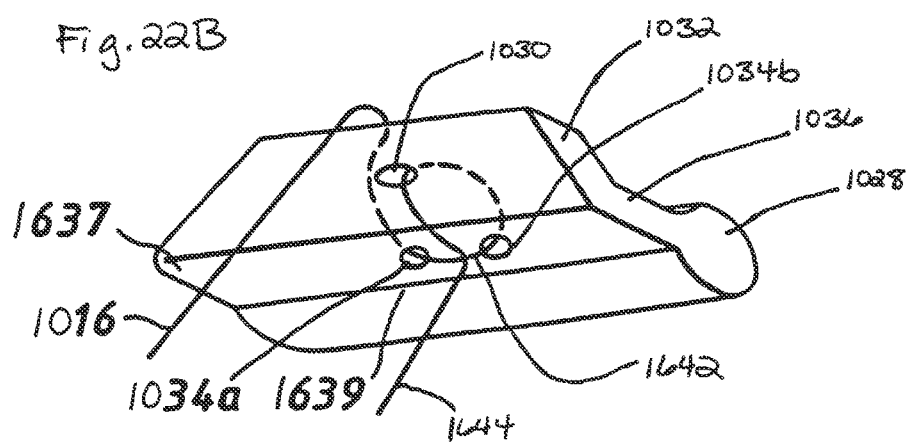

For example, referring first to FIGS. 22A and 22B, suture 1016 can be threaded through the second retainer 1014 so that the loop is located against an exterior surface 1637 of the stem 1036, rather than within the region 1039. In this embodiment, suture 1016 is threaded through the second retainer 1014 by first passing the suture around the base 1032, into the region 1039, and then out of the region 1039 through the hole 1034a. The suture then passes back into the region 1039 through the hole 1034b, forming a loop 1642 adjacent the surface 1637. After forming the loop, the suture passes through the hole 1030 to the exterior, and then through the loop 1642, terminating at the free end 1644.

When the surgeon pulls the free end 1644 of suture 1016, the retainer rotates until the surface 1637 faces the surface 1058 of meniscus 1050 (FIGS. 16 and 17A-17B). The cylindrical body 1028 causes part of the surface 1637 to remain elevated above the surface 1058, creating a small gap 1639 that contains the loop 1642. The loop 1642, therefore, does not become wedged between tissue and the surface 1637 when the surgeon pulls the free end 1644 to tension the suture.

Figure 23:
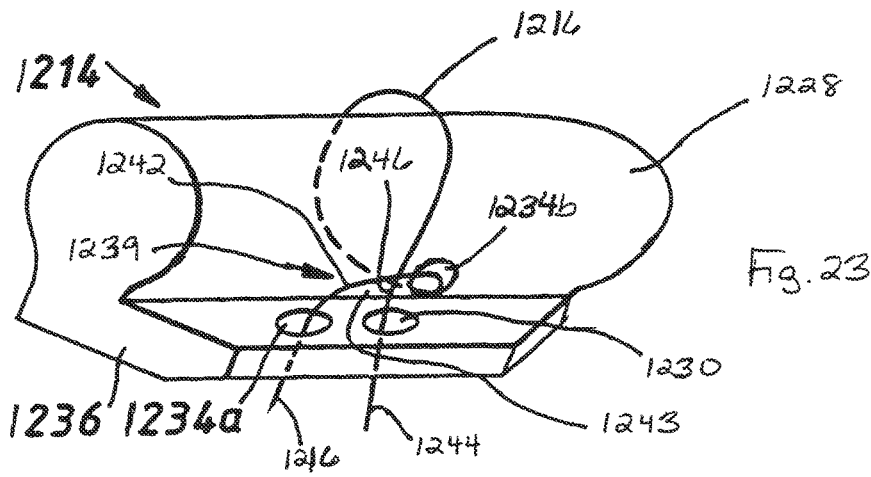
FIGS. 23-26 are perspective views of alternative configurations of the fixation member and one-way knot of FIGS. 17A and 17B.

Referring to FIG. 23, a second retainer 1214 has a structure similar to the retainer 1014, except that the retainer 1214 lacks a base 1032. The retainer 1214 includes a cylindrical body 1228 and a stem 1236 that define a wedge-shaped, partially enclosed region 1239 therebetween. The stem 1236 defines two holes, 1234a and 1230, and the body 1228 defines one transverse hole 1234b. Holes 1234a and 1230 are generally parallel, and are both generally perpendicular to hole 1234b. A suture 1216 passes from a first retainer (not shown) through hole 1234a into the region 1239, and then through hole 1234b to the exterior of the retainer, forming a loop 1242 within the region 1239. The suture then wraps around the body 1228 back into the region 1239, through the loop 1242, and out of the region 1239 through hole 1230, terminating at the free end 1244. Alternatively, suture 1216 can wrap around the body 1228 two or more times before passing back into the region 1239.

As in the previous embodiments, pulling on the free end 1244 tensions suture 1216 and shortens the length of suture between the retainers. Pulling on suture 1216 in an opposite direction, however, causes the loop 1242 to press a portion 1246 of the suture against a compression surface 1243. Since the loop 1242 is located within the protected region 1239, and is therefore spaced from the meniscal surface, the loop 1242 does not become wedged between tissue and the retainer when the surgeon tensions suture 1216. Unlike the previous embodiments, however, the retainer 1214 does not rotate after the surgeon tensions the suture and releases the free end 1244.

Figure 24:
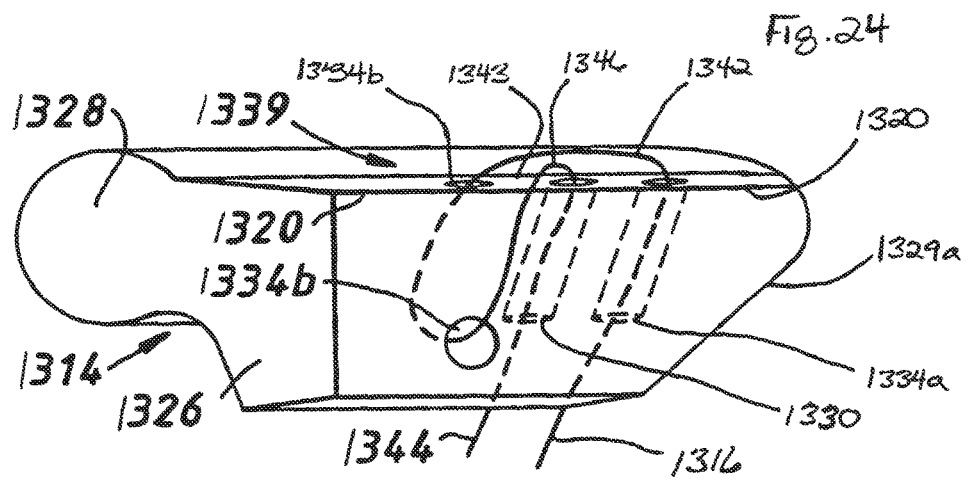

Referring to FIG. 24, a second retainer 1314 includes a generally cylindrical body 1328 and an offset, generally rectangular appendage 1326. The appendage 1326 and the body 1328 define a partially protected region 1339. As with the retainer 1014, a front surface 1329a of the retainer 1314 is beveled.

The appendage 1326 defines three holes, 1330, 1334a, and 1334b. Holes 1334a and 1330 are generally straight, while hole 1334b defines an arc through an inside of appendage 1326. A suture 1316 passes from a first retainer (not shown) through straight hole 1334a into the region 1339. Suture 1316 then passes out of region 1339 through arc-shaped hole 1334b, forming a loop 1342 within the region 1339. The suture then wraps around a corner 1320 of the body 1326, passes through the loop 1342, and through hole 1330, terminating at a free end 1344. As with the embodiments of FIGS. 15, 21A-21B, and 22, pulling on the free end 1344 shortens the length of suture between the retainers, but pulling on suture 1316 in an opposite direction causes the loop 1342 to squeeze a portion 1346 of the suture against a compression surface 1343 of the appendage 1326, preventing further movement. Like the embodiment of FIG. 22, the retainer 1314 does not rotate after the suture is tensioned and released.

Figure 25:
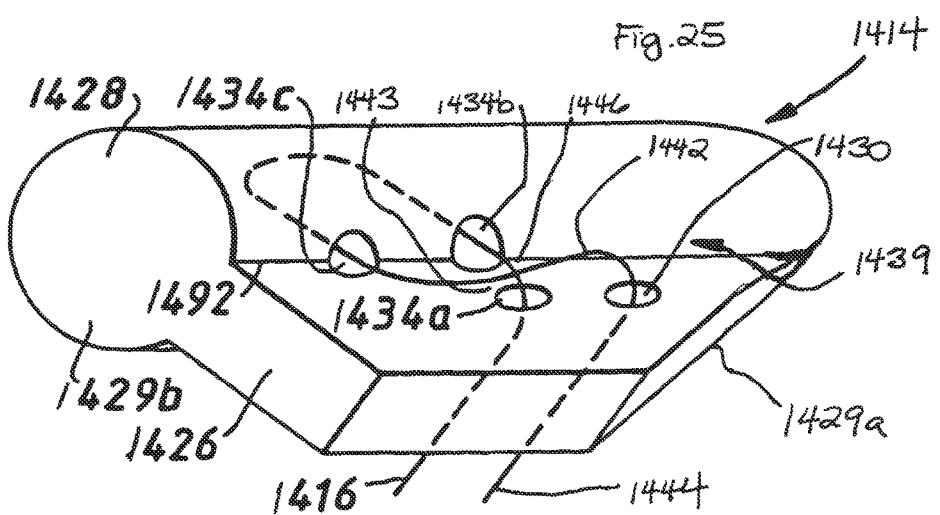

Referring to FIG. 25, a second retainer 1414 includes a generally cylindrical body 1428 extending from a beveled distal surface 1429a to a flat proximal surface 1429b. A generally rectangular appendage 1426 also extends from the surface 1429a to the surface 1429b. The rectangular appendage 1426 is attached to the body 1428 along the long side of the rectangle, and is centered along an axial length of the body 1428. The body 1428 and the appendage 1426 define a protected region 1439.

The appendage 1426 defines two holes, 1434a and 1430, and the body 1428 defines two transverse holes, 1434b and 1434c. Hole 1434b is located entirely within the body 1428, but hole 1434c is located at a juncture 1492 between the body 1428 and the appendage 1426. Holes 1434a and 1430 are generally parallel, and are both generally perpendicular to holes 1434b and 1434c.

A suture 1416 extends from a first retainer (not shown), through hole 1434a into the region 1439, and then out of the region 1439 through hole 1434b, forming a loop 1442 within the region 1439. The suture then passes back into the region 1439 through hole 1434c, through the loop 1442, and out of the region 1439 through hole 1430, terminating at a free end 1444.

As with the other described second retainer embodiments, pulling on the free end 1444 tensions suture 1416 and shortens the length of suture between the retainers, but pulling on suture 1416 in an opposite direction causes the loop 1442 to squeeze a portion 1446 of the suture against a compression surface 1443 of the appendage 1426, preventing further movement. The region 1439 is separated from the meniscal tissue by the body 1428, preventing the loop 1442 from wedging between the retainer 1414 and tissue when the surgeon pulls on the free end 1444. The retainer 1414 does not rotate after the surgeon tensions and releases the suture.

Figure 26:
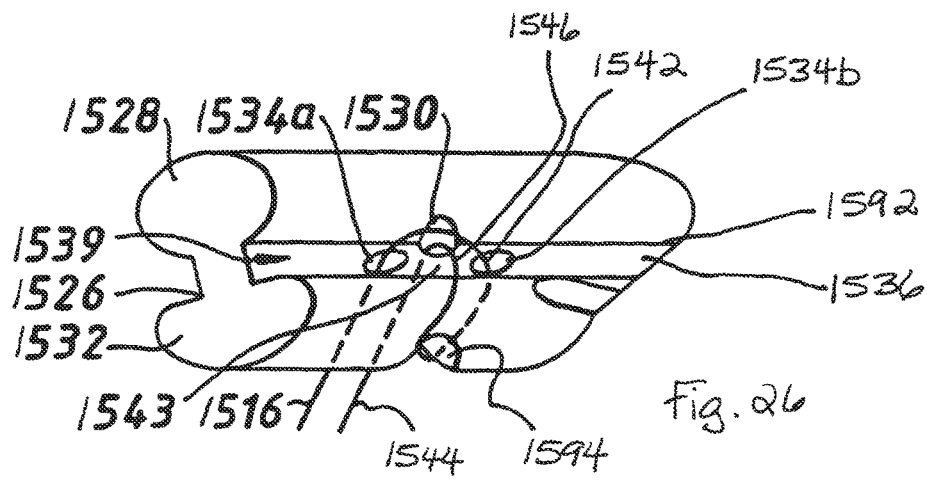

Referring to FIG. 26, a second retainer 1514 includes a generally cylindrical body 1528 and an appendage 1526. Both the body 1528 and the appendage 1526 extend from a beveled distal surface 1529a to a flat proximal surface 1529b. The appendage 1526 includes a stem 1536 attached to the body 1528, and a head 1532 attached to the stem 1536. The stem 1536 is rectangular in cross-section and the head 1532 is D-shaped in cross-section, giving the appendage 1526 a mushroom-shaped cross-section. The stem 1536, the head 1532, and the body 1528 define a partially enclosed, protected region 1539.

The stem 1536 defines two transverse holes 1534a and 1534b, and the body 1528 defines a single transverse hole 1530 located at a juncture 1592 between the body 1528 and the stem 1536. A suture 1516 passes from a first retainer (not shown), through hole 1534a into the protected region 1539, and then out of region 1539 through hole 1534b, forming a loop 1542 within the region 1539. Suture 1516 then passes around the D-shaped head 1532 through a transverse groove 1594 in the head 1532, back into the region 1539, through the loop 1542, and out hole 1530, terminating at a free end 1544. As with the other described embodiments of the second retainer, pulling on the free end 1544 shortens the distance between the two retainers, but pulling on suture 1516 in an opposite direction causes the loop 1542 to squeeze a portion 1546 of the suture against a compression surface 1543 of the stem 1536, preventing further movement. Because the loop 1542 is located within the region 1539, the loop is prevented from becoming wedged between the retainer and tissue when the surgeon pulls on the free end 1544. The retainer 1514, like the retainers 1214, 1314, and 1414, does not rotate after the surgeon tensions and releases the suture.

Figures 27A, 27B:
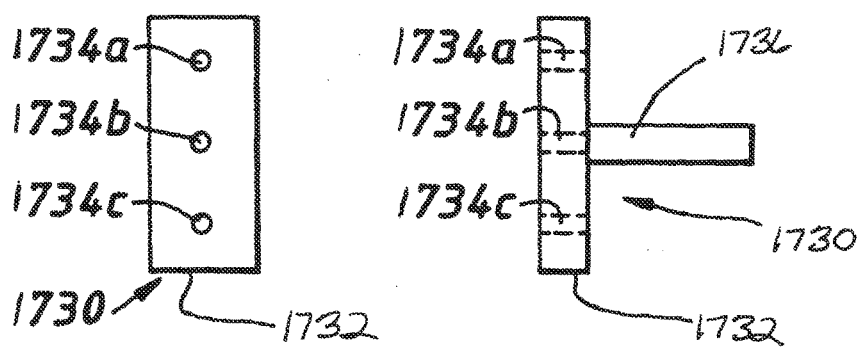
FIG. 27A is a top view of a T-shaped second fixation member.
FIG. 27B is a side view of the T-shaped fixation member of FIG. 27A.
Figures 27C, 27D:
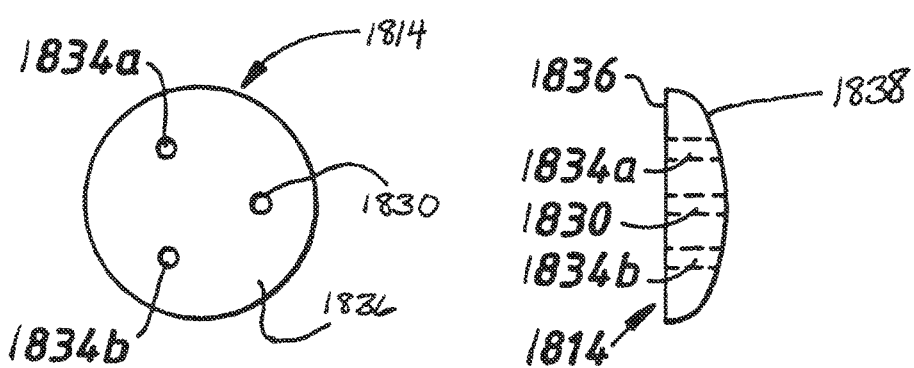
FIG. 27C is a front view of a crescent-shaped second fixation member.
FIG. 27D is a side view of the crescent-shaped fixation member of FIG. 27C.

Referring to FIGS. 27A-27D and FIGS. 28-30, the second retainer can have a T shape or a crescent shape, and can be deployed at a surface of the meniscus or inter-body. Referring to FIGS. 27A and 27B, a second retainer 1730 has a T-shape. The base 1732 of the T defines three through-holes, 1734a, 1734b, and 1734c, and the stem 1736 of the T is configured to penetrate meniscal tissue. The stem 1736 is offset from the base 1732 so that the stem does not block hole 1734b. Referring to FIGS. 27C and 27D, a second retainer 1814 has a flat, generally circular proximal surface 1836, and a rounded distal surface 1838, giving the retainer a generally hemispherical or "crescent" shape. (Alternatively, the surface 1836 can be concave.) The retainer 1814 defines three through-holes, 1830, 1834a, and 1834b. The holes pass in an axial direction from the retainer's proximal circular surface 1836 to its distal rounded surface 1838.

FIG. 28 illustrates deployment of a device 1810 that has a crescent-shaped second retainer 1814, and a "pulley" retainer 1813. The pulley retainer 1813 does not act as a dead-end for a suture, nor does it include a one-way knot. Instead, the pulley retainer 1813 includes two through-holes, 1824a and 1824b. A suture 1816 passes through hole 1824a in a first direction, and then through hole 1824b in a second direction, such that suture 1816 can slide over the pulley retainer 1813 in either direction. The pulley retainer 1813 can have the shape and structure of the retainer 1012 (that is, the holes are located on a fin), the simple cylindrical structure of the retainer 1112 of FIG. 21A, or numerous other structures.

In operation, the retainers 1813 and 1814 are deployed using, for example, a hollow needle 1070, such that the retainer 1814 is positioned on a proximal side of meniscus 1050, and the retainer 1813 is deployed against the distal surface 1058. When deployed, suture 1816 passes through hole 1834a of the crescent-shaped retainer 1814 in a generally proximal direction (arrow P), from rounded surface 1838 to circular surface 1836, and then through hole 1834b in a generally distal direction (arrow D), forming a loop 1842. From the loop 1842, the suture passes through meniscal tissue, through hole 1824a of the pulley retainer 1813, through hole 1824b of the retainer 1813, and back through meniscal tissue to the crescent shaped retainer. The suture then passes through the loop 1842, terminating at a free end 1844. The opposite end 1845 of suture 1816 includes a knob or a knot 1847 that prevents end 1845 from passing through hole 1834a. Thus, suture 1816 begins at the retainer 1814, in addition to forming the one-way knot at the retainer 1814.

Referring to FIG. 29, rather than beginning at retainer 1814, the suture can be affixed to a first retainer 1012. In FIG. 29, a device 1811 includes a first retainer 1012 and a crescent-shaped second retainer 1814. Suture 1816 passes through holes 1024a and 1024b of the retainer 1012, forming a knot 1025 as shown in FIG. 15A. From the knot 1025, suture 1816 passes through meniscal tissue and then through holes 1834a and 1834b of the retainer 1814, forming a loop 1842. From the loop 1842, the suture passes back through meniscal tissue to the first retainer 1012, and then through a fixed loop 1843 located between the knot 1025 and the first retainer 1012. The suture then passes back through meniscal tissue, through hole 1830 of the retainer 1814, and through the loop 1842, terminating at the free end 1844.

When a surgeon pulls on the free end 1844 in the device 1811, the mechanical advantage is 3:1, since suture 1816 passes between the two retainers three times. By comparison, in the device 1810, the mechanical advantage is 2:1.

Referring to FIG. 30, the crescent shaped retainer 1814 of the device 1810 can be deployed inter-body (that is, embedded within meniscal tissue), rather than against a surface of the meniscus. In this deployment method, the device 1810 is deployed in the manner described above with reference to FIG. 28, or using another deployment method. After positioning the retainers and tensioning the free end 1844, however, the surgeon pushes the retainer 1814 into the meniscal tissue, using, for example, a needle. To facilitate pushing the retainer 1814 into the tissue, a point 1817 of the retainer 1814 can be sharp.

Other types of second retainers described herein, whether or not they include a sharp point, can also be positioned inter-body.

In each of the described embodiments of the second retainer, the one-way knot can be left "loose" until after both the first and second retainers are positioned against the meniscus. In such an embodiment, the suture would be very long, for example, more than 12 cm long, such that the one-way knot includes considerable slack, and the loop portion of the knot is accessible to the surgeon's fingers. In this embodiment, the surgeon can position the first and second retainers against the backside 1058 by pulling on both the free end and the loop itself. Once the retainers are satisfactorily positioned, the surgeon tightens the knot by pulling on the free end.

The second retainer can employ one-way tightening schemes other than a "one-way knot." For example, referring to FIG. 31, a device 1650 includes the first retainer 1012, a second retainer 1652, and two sutures 1616 and 1654. The second retainer 1652 has a generally cylindrical shape, and defines two through-holes 1656 and 1658. When the retainers 1012 and 1652 are positioned against the backside 1058 of meniscus 1050, suture 1616 passes from the first retainer 1012, through holes 1060a and 1060b in the meniscus, and then through holes 1656 and 1658 of the retainer 1652, terminating at a free end 1660. Suture 1616 does not form a one-way knot at the second retainer 1652. Instead, suture 1616 simply passes through holes 1656 and 1658 in succession, such that the second retainer 1652 acts as a pulley retainer.

The second suture, suture 1654, passes only through hole 1656 of the second retainer 1652, and through hole 1060b of the meniscus. A portion 1662 of suture 1654, distal to hole 1656, is thicker than the remainder of suture 1654. This thicker portion 1662 cannot pass through hole 1656. (The thickness of portion 1662 is exaggerated in FIG. 31.)

In operation, a surgeon deploys the two retainers as described above with respect to other embodiments, and then pulls on the free end 1660 of suture 1616 to position the retainers against the backside 1058 and close the tear in the meniscus. Once suture 1616 is tensioned to the surgeon's satisfaction, the surgeon pulls on suture 1654 in the proximal direction (arrow P), until a segment of the portion 1662 wedges into hole 1656. The portion 1662 wedges suture 1616 in place within hole 1656, preventing the length of suture 1616 between the two retainers from increasing, and thereby locking the two retainers in place.

Modifications of other portions of the wound closure device 1010 are also possible. For example, the fin-shaped projection 1020 of the first retainer need not have the shape shown in the figures. Other types of projections capable of protruding through a needle opening and engaging tissue can be used. In addition, as described above with reference to FIG. 20A, the first retainer need not include any projection, but can instead be a simple cylinder defining holes for affixation of the suture.

Instead of attaching the suture to the first retainer using a conventional knot 1025, the suture can be welded or glued to the retainer, or can be spliced.

Referring to FIG. 32A, the first retainer need not include an extended, cylindrical body, but can instead have a button-shaped body. Button-shaped first retainer 1712 includes a circular distal side 1719a and a circular proximal side 1719b. Two axial holes 1724a and 1724b pass from side 1719a to side 1719b. A suture 1716 is attached to the retainer 1712 by passing through hole 1724a in a first direction, through hole 1724b in a second direction, and then forming a conventional knot 1725 on the distal side of the retainer.

Referring to FIG. 32B, the button-shaped first retainer 1712 is deployed against a proximal surface 1796 of meniscus 1050, and the second retainer 1014 is deployed against the surface 1058. Suture 1716 passes from the first retainer 1712 into proximal tissue 1056 at point 1760, such that the knot 1725 is located within the tissue. From point 1760, suture 1716 passes across the tear 1052 to the second retainer 1014, then through the second retainer 1014 in the manner described above with reference to FIG. 15. From the second retainer 1014, the suture passes back into the distal tissue 1054, across the tear 1052, and emerges from proximal tissue 1056 at point 1760. The suture then terminates at the free end 1744. As with the embodiments described above, pulling on the free end 1744 tensions the suture and closes the tear.

Alternatively, the button-shaped retainer 1712 can be deployed on the distal side of the tear adjacent the second retainer 1014, using the methods described above with reference to FIGS. 16, 19A-19D, 20A-20D, and 21A-21D.

The second retainer need not include a groove 1035 to allow passage of a plunger. Instead, the second retainer can define an axial through-hole for passage of the plunger.

Rather than a suture, the first and second retainers can be connected with other types of flexible members.

The wound closure device can include more than two retainers. For example, in addition to the first and second retainers, the device can include a third retainer identical in structure and function to the second retainer. In operation, after deploying the second retainer against the surface 1058 of meniscus 1050, the surgeon could again pass the suture across the tear 1052, adding an additional stitch, and then deploy the third retainer against the surface 1058. After deploying all three retainers, the surgeon would pull on the free end of the suture, causing the suture to slide over both the second and third retainers, shortening the length of suture between the third and first retainers, and thereby closing the wound.

When more than two retainers are used, one or more of the retainers can be a pulley, such as the pulley retainer 1813 described above with reference to FIG. 28. For example, the device could include a first retainer 1012, a pulley retainer 1813, and a second retainer 1014. The suture would be affixed to the first retainer, would slide over the pulley retainer, and form a one-way knot at the second retainer.

Referring to FIGS. 33-35, a device 308 for repairing a tear 12 in tissue 14 includes a suture 310 attached to a single fixation member 326. The fixation member 326 defines through holes 330, 332 for receiving suture 310. Suture 310 has a first end 312 attached to suture 310 at point 314 (as described above with reference to FIG. 2B) to form a looped end 316 remote from fixation member 326, and a second, free end 334.

When implanted in the knee joint, the fixation member 326 lies on a surface 20 of tissue 14. The looped end 316 is located in tear 12 and extends along the surface 26 of tissue 14. Suture 310 extends through tissue 14, passing through the looped end 316 in tear 12, and emerging at the tissue surface 20 where suture 310 loops through the fixation member 326. Suture 310 extends back through tissue 14, passing through the looped end 316 in tear 12 and through a limiting element such as a slip knot 321 formed in suture 310, and emerging at the tissue surface 26. As described further below, after the device 308 is positioned in tissue 14, the user pulls on the free end 334 of suture 310, in the direction of arrow 520, to bring the sides 22, 24 of tear 12 together into juxtaposition (as shown in FIG. 33). The slip knot 321 limits loosening of suture 310. Alternatively, the looped end 316 is located on the surface 20 between the fixation member 326 and surface 20, as shown in dashed line in FIG. 33.

Referring to FIGS. 36-36B, a delivery device 399 for implanting device 308 includes a suture holder 400 and a needle 460. The suture holder 400 includes a tube 410 defining a lumen 415 through which the needle 460 extends, a shaft 420, and a distal portion 430. The distal portion 430 has a first tine 440 defining grooves 445 and 446, and a second tine 450 defining grooves 455, 456. The needle 460 has a beveled tip 461 and a slot 462 in a top portion 463 of the needle 460.

When assembled, the fastening member 326 with attached suture 310 is positioned in the slot 462 with suture 310 preformed with the looped end 316 and the slip knot 321. The slip knot 321 is formed as described above with reference to FIGS. 2A-21, though where the fixation member 16 is positioned in FIGS. 2A-21, suture 310 is formed as the looped end 316 (FIG. 36C). The looped end 316 is positioned on the suture holder 400 within the grooves 445, 446, 455 and 456 of the tines 440, 450 (FIG. 36B), and extends along a bottom side 480 of the shaft 420. As shown in FIG. 36, the delivery device 399 includes a handle 451 with a push knob 453 for advancing the needle 460 relative to the suture holder 400.

Referring to FIG. 37, in use, the user inserts the distal portion 430 of the suture holder 400 into tear 12 of tissue 14, and then advances the needle 460 through tissue 14, traversing tear 12, and exiting tissue 14 at the tissue surface 20. The needle 460 passes between the tines 440 and 450, and thus through the looped end 316 of suture 310 (FIG. 38). The user then retracts the needle 460 from tissue 14 (FIG. 39). The contact of the fastening member 326 with tissue surface 20 during the retraction of the needle 460 acts to push the fastening member 326 out of the needle 460 such that the fastening member 326 remains at surface 20, as described above with reference to FIG. 7. Pulling on the free end 334 of suture 310 brings the sides 22, 24 of tear 12 into juxtaposition. The slip knot 321 secures the device 308 in place. Excess suture 310 can then be cut off.

Referring to FIG. 40, rather than the securing device 308 with a slip knot, suture 310 includes a limiting element in the form of a Chinese trap or hand cuff 495, that is, an element that when pulled on, tightens around something disposed within the element. The free end 334 of suture 310 is slidably received within the trap 495. When the free end 334 of suture 310 is pulled in the direction of arrow 520, the trap 495 is stretched, eventually gripping suture passing therethrough to secure suture 310 and the device 308. The limiting element can also take the form of limiting elements described above with reference to FIGS. 12-12C and 13.

Referring to FIG. 41, a device 799 for repairing tear 12 in tissue 14 includes a fixation member such as a barbed fixation member 800 and a suture 820. Suture 820 has an end 810 attached to the fastening member 800. Suture 820 is formed in a loop 830 with a second end 832 of suture 820 attached to suture 820. The delivery device 399 (FIG. 36) can be used to deploy the device 799 with suture 820 being tightened to close tear 12 by pushing the fastening member 800 in the direction of arrow 840, rather than pulling on a free end of suture. The barbed fixation member 800 limits loosening of suture 820.

Figure 42:
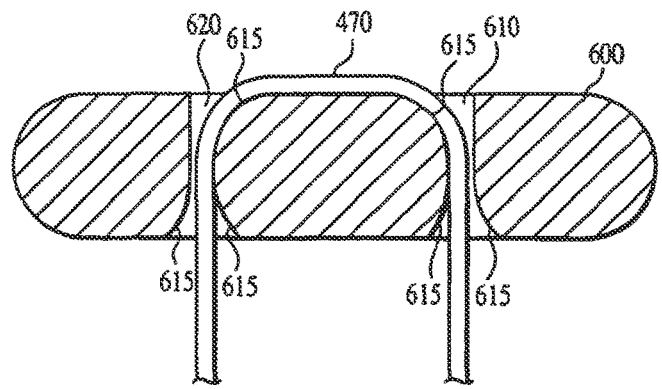
FIGS. 42 and 43 are alternative embodiments of a fixation member of the closure device of FIG. 33.
Figure 43:
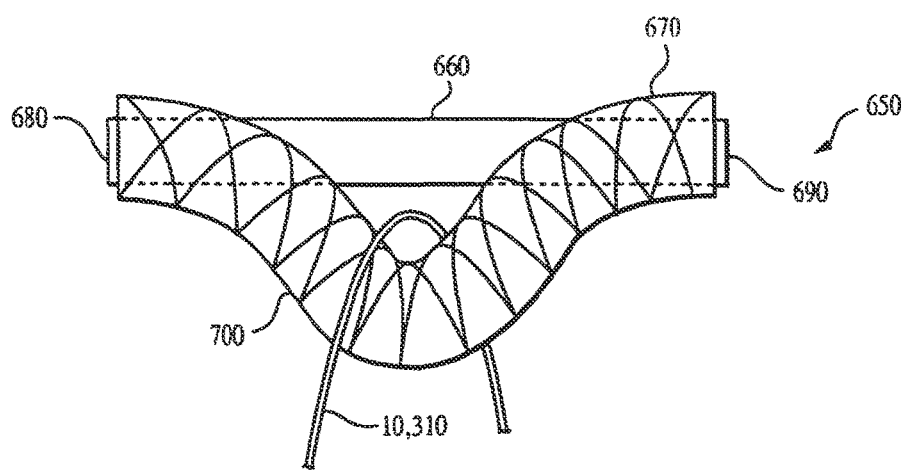

Referring to FIG. 42, an alternative embodiment of a fixation member 600 includes through bores 610, 620 with radiused corners 615 to reduce friction between suture 470 and the fixation member 600. Referring to FIG. 43, another embodiment of a fixation member 650, which can be used in any of the above embodiments, includes a solid rod 660 with ends 680, 690, and a braided suture 670 attached to the ends 680, 690. Suture 670 forms a loop 700 for receiving suture 10 or suture 310. The loop 700 lines up with suture 10, 310 to act as a pulley and reducing friction between the suture and fixation member.

Figure 44:
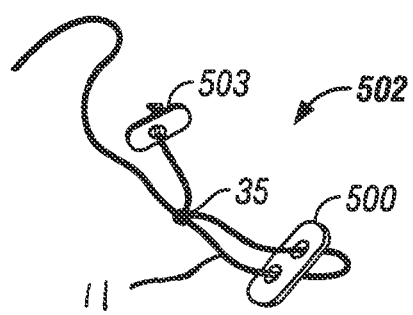
FIG. 44 illustrates an alternative embodiment of a surgical device that includes two fixation members, a suture, and a slip knot.
Figure 45:
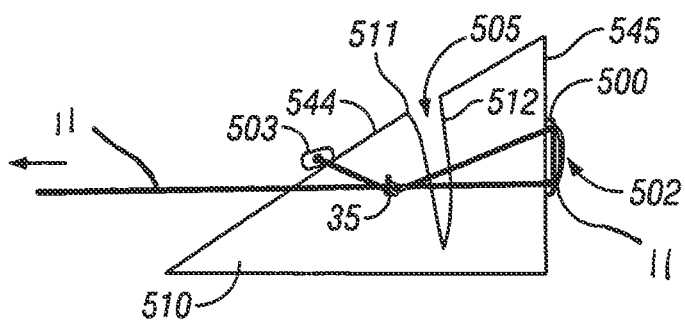
FIG. 45 illustrates the surgical device of FIG. 44 used to repair a meniscal tear.

Referring to FIGS. 44 and 45, a surgical device 502 for repairing a tear 505 in soft tissue, for example, meniscal tissue 510, includes a first fixation member 500 and a second fixation member 503 connected by a flexible member such as suture 11 that is tied in a limiting element such as a slip knot 35 such that the distance between the fixation members 500, 503 can be shortened but not lengthened. The slip knot 35 is moved to shorten the distance between the fixation members 500, 503 to appose the two edges 511, 512 of the meniscal tear 505. The slip knot 35 of FIG. 44 is positioned between the first fixation member 500 and the second fixation member 503. Thus, when the surgical device 502 is implanted, the slip knot 35 is positioned within tissue between the first fixation member 500 and the second fixation member 503 (as shown in FIG. 45).

The first fixation member 500 is positioned on an anterior surface 545 of the meniscal tissue 510 and the second fixation member 503 is positioned on a posterior surface 544 of the meniscal tissue 510. The free end 115 of the suture 11 extends out of the posterior surface 544 and the slip knot is within the meniscal tissue 510. When the slip knot 35 is moved to appose the two edges 511, 512, the slip knot 35 remains within the meniscal tissue 510.

Referring to FIGS. 46 and 47, the first fixation member 500, the second fixation member 503, the suture 11, and the slip knot 35 (shown as a block for simplicity) are delivered to a surgical site in a delivery device 517 that includes a handle 520, a needle 525, and a pusher tube 530. The needle 525 extends from the handle 520 and includes a longitudinal slot 535 extending along the length of the needle 525 except for a proximal portion 534 of the needle. The needle 525 includes a distal end 536 that tapers to a sharp distal point 537. The pusher tube 530 is positioned within a lumen 538 of the needle 525 and includes a proximal thumb switch 540 that is positioned outside of the needle 525 but is connected to the tube 530 by a connecting plate 541 that passes through the slot 535. The pusher tube 530 also includes a distal end 542 for contacting and pushing the first fixation member 500. The thumb switch 540 is used to advance and retract the pusher tube 530. For example, the thumb switch is advanced to contact and dislodge the first fixation member 500 from the needle 525. The needle 525 can be withdrawn from the pusher tube 530 such that the pusher tube 530 can function alone as a knot pusher.

In use, the first fixation member 500 is positioned within the needle lumen 538 in a position adjacent to the distal end 542 of the pusher tube 530. The slip knot 35 and the second fixation member 503 are positioned outside of the needle 525. The suture 11 extends from the slip knot 35 through the slot 535 into the needle lumen 538 and passes proximally through a lumen 543 in the pusher tube 530 and a channel 546 in the handle 520.

Figure 48:
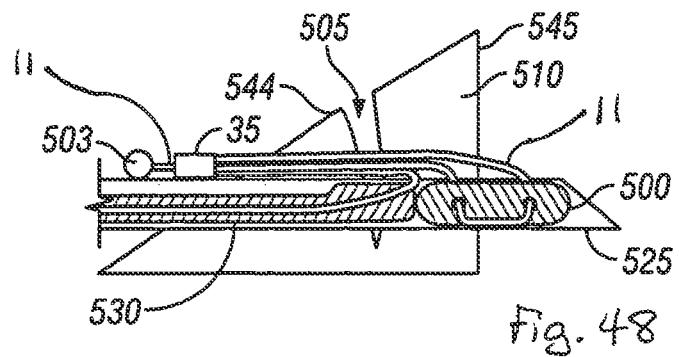
FIGS. 48-51 illustrate the surgical device and delivery device of FIG. 46 in use repairing a tear in meniscal tissue.
Figure 49:
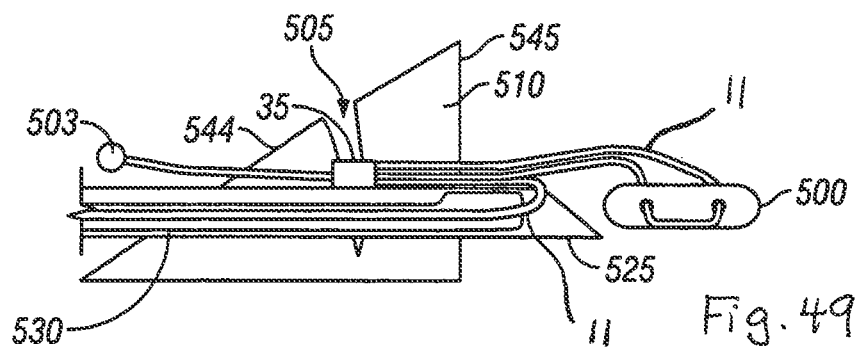

Referring to FIGS. 48-51, the meniscal tear 505 is repaired in a simple insertion and removal operation in which the needle 525 is inserted into and through the meniscal tissue 510, the first fixation member 500 is deployed, and the needle 525 is withdrawn. Referring specifically to FIGS. 48 and 49, initially the needle 525 is passed from the posterior surface 544 of the meniscus 510 to the anterior surface 545 of the meniscus 510. The suture 11 and the slip knot 35 are pulled into the meniscus 510 with the needle 525 such that the slip knot 35 is positioned within the meniscal tissue 510. The second fixation member 503 remains positioned outside of the meniscus 510 against the posterior surface 544. The physician then advances the pusher tube 530 to dislodge the first fixation member 500 from the needle 525 to a position adjacent to the anterior surface 545 of the meniscus 510. This action further pulls the slip knot 35 such that the slip knot remains in the meniscal tissue 510.

Figure 50:
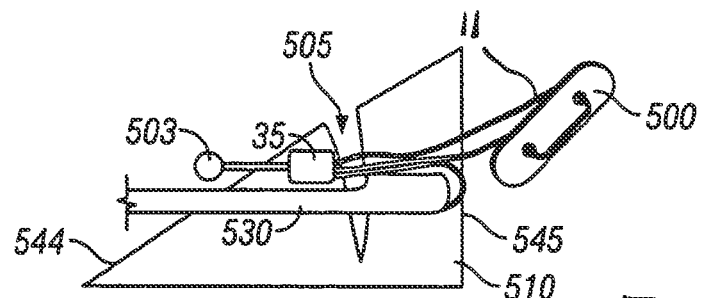
Figure 51:
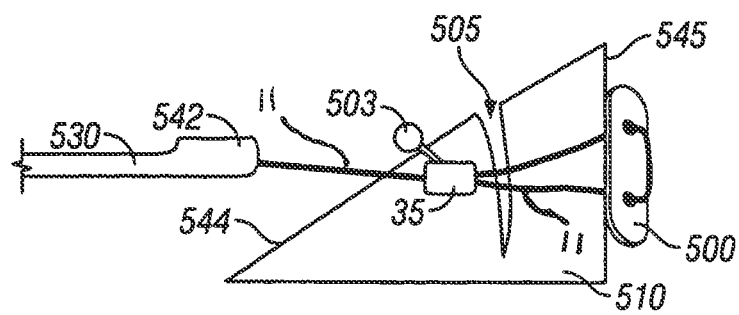

Referring to FIG. 50, the physician withdraws the needle 525 from the meniscus 510 leaving the pusher tube 530 within the meniscus 510. By next advancing the pusher tube 530 while holding the suture 11 to apply tension to the suture 11, the physician uses the pusher tube 530 as a knot pusher to push or advance the slip knot 35 to shorten the length of the suture 11 between the first fixation member 500 and the second fixation member 503, closing the meniscal tear 505. Using the pusher tube 530 as a knot pusher aids the physician in seating the knot 35 deep within the tissue. Referring to FIG. 51, the physician next withdraws the pusher tube 530 from the meniscus 510 and, to complete the repair, cuts the suture 11 adjacent to the posterior surface 544 of the meniscus 510. If necessary, the physician inserts additional fixation members 500 and 503 to further repair the tear.

Figure 52:
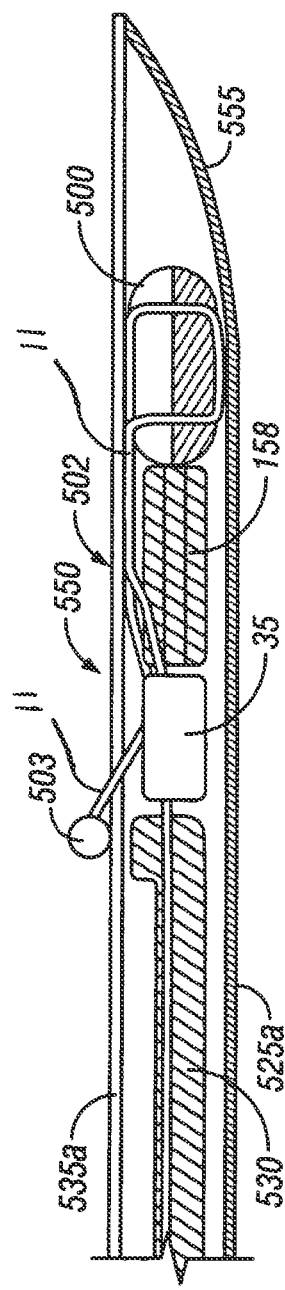
FIG. 52 is a cross-sectional side view of an alternative embodiment of a delivery device for the surgical device of FIG. 44.

Referring to FIG. 52, in another implementation, an atraumatic device 550 for delivering the surgical device 502 has a needle 525a with a curved distal end 555 rather than the tapered distal end 536 of the needle 525. The needle 525a also has a slot 535a. The curved delivery device 550 is used to deliver the first fixation member 500, the second fixation member 503, the suture 11, and the slip knot 35. The curved distal end 555 is used to avoid neuromuscular tissue, for example, in the knee joint when inserting the needle 525a. The curved delivery device 550 is loaded with the fixation members 500, 503, the suture 11, and the slip knot 35 in a different manner than the delivery device 517. In particular, while the second fixation member 503 remains positioned external to the needle 525a, the slip knot 35 is placed within the needle 525a and the suture 11 extends from the slip knot 35 through the slot 535a to the second fixation member 503 and back through the slot 535a to the slip knot 35 and proximally through the pusher tube 530. Positioning the slip knot 35 within the needle 525a advantageously reduces the profile of the device 550 and also protects the slip knot 35 from contacting any surfaces that could possibly damage the slip knot 35. The slip knot 35 and the first fixation member 500 are separated by the block 158, having features described above.

If there is no block 158 positioned between the first fixation member 500 and the slip knot 35, the physician can accidentally dislodge the slip knot 35 prematurely if he or she pushes the pusher tube 530 too far distally. By including the block 158 to separate the first fixation member 500 and the slip knot 35, the physician has more distance that he or she can push the pusher tube 530 forward without accidentally dislodging the slip knot with the first fixation member 500. When the pusher tube 530 is advanced to an extended position, the block 158 is pushed out of the needle 525 with the first fixation member 500. Because the block 158 is bioabsorbable, it will be absorbed and thereby not remain adjacent to the tissue as a long-term irritant.

The delivery device 555 is used to deliver the first fixation member 500, the second fixation member 503, the slip knot 35, and the suture 11 in the same manner as the delivery device 517. A primary difference in the manner of delivery is the ability to direct the curved distal end 555 around neuromuscular tissue. Although the slip knot 35 is delivered within the needle 525, this does not affect the manner in which the physician delivers the first fixation member 500 or the second fixation member 503. Although shown having a curved distal end 555, the needle 525a also will function with a straight end.

Figure 53:
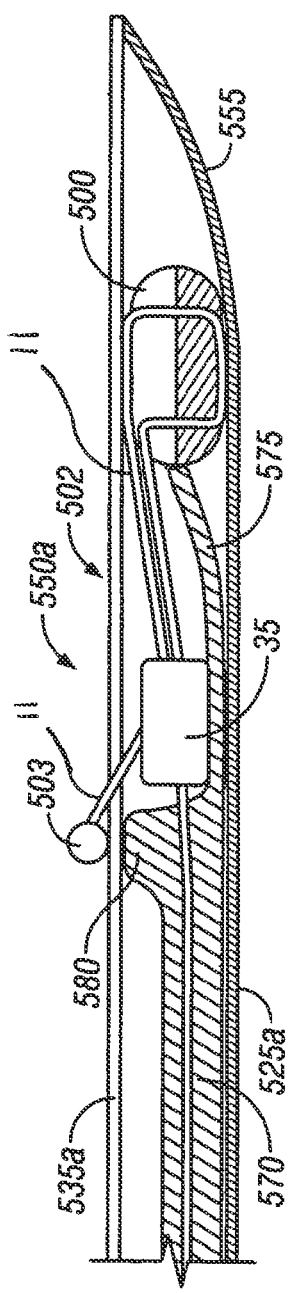
FIG. 53 is a cross-sectional side view of another alternative embodiment of a delivery device for the surgical device of FIG. 44.

Referring to FIG. 53, as an alternative to the block 158, a delivery device 550a includes a pusher tube 570 having a narrow distal section 575 and a wider middle section 580. Like the block 158 described above with respect to FIG. 52, the narrow distal section 575 is used to increase the distance that the physician can advance the pusher tube without accidentally dislodging the slip knot 35. The slip knot 35 is positioned on the narrow distal section 575 at a position adjacent to the wider middle section 580. In use, the physician advances the pusher tube 570 to push the first fixation member 500 out of the needle 525. By advancing the pusher tube 570 further, the middle section 580 aids in pushing the slip knot 35 out of the needle 525a. Although the slip knot 35 will be pulled out by merely retracting the needle 525 after placing the first fixation member 500, the middle section 580 provides the physician extra control in placing the slip knot. Moreover, the middle section 580 functions as a knot pusher to push or advance the slip knot 35 deeper into the meniscal tissue. Otherwise, the first fixation member 500, the second fixation member 503, and the slip knot 35 are delivered in the same manner as described above. Namely, the needle 525a is inserted through the meniscus 510 and the meniscal tear 505, the pusher tube 570 is advanced to an extended position to place the first fixation member 500 against the anterior surface 545 of the meniscus 510, thereby advancing the wider section 580. Finally, the needle 525a is withdrawn, which leaves the slip knot 35 in the meniscal tissue 510 and the second fixation member 503 positioned against the posterior surface 544 of the meniscus 510. The pusher tube 570 then is advanced to use the wider section 580 as a knot pusher to push the slip knot 35 to shorten the length of suture 11 between the first fixation member 500 and the second fixation member 503, which apposes the edges of the tear 505. The pusher tube 570 then is withdrawn and the suture 11 is cut proximally to the slip knot 35.

Referring to FIG. 54, a surgical device 2000 includes a first fixation member 2005, a second fixation member 2010, and a flexible member, such as a suture 2015. The suture 2015 couples the first fixation member 2005 and the second fixation member 2010, and has a knot 2020 formed at each end 2025 of the suture 2015 to prevent the respective fixation member from being separated from the suture 2015. The first fixation member 2005 includes a longitudinal channel 2030 and a fin 2035. The longitudinal channel 2030 is open to a side 2033 of the fixation member. As described in more detail below, the fin 2035 is used to catch tissue to release the first fixation member 2005 from a delivery device when the delivery device is withdrawn from a tissue site during a surgical procedure. The second fixation member 2010 includes a longitudinal channel 2040 that opens to a side 2045. As described in more detail below, the openings to the sides 2033, 2045 allow the first fixation member 2005, the second fixation member 2010, and the suture 2015 to be placed under tension and cause the retainers to shift relative to the suture to be aligned generally perpendicularly to the suture. In this manner, the fixation members 2005, 2010 resist pullback through tissue.

Referring also to FIG. 55, the surgical device 2000 is delivered into tissue, such as meniscal tissue, using a delivery device 2050 that includes a needle 2055, a handle 2060, and a thumb-activated pusher rod 2065. The needle 2055 includes a longitudinal slot 2070 through which the fin 2035 extends. The thumb-activated pusher rod 2065 can be used to maintain the position of the fixation members 2005, 2010 within the needle 2055 during delivery and to assist in delivering the second fixation member 2010.

Figure 56:
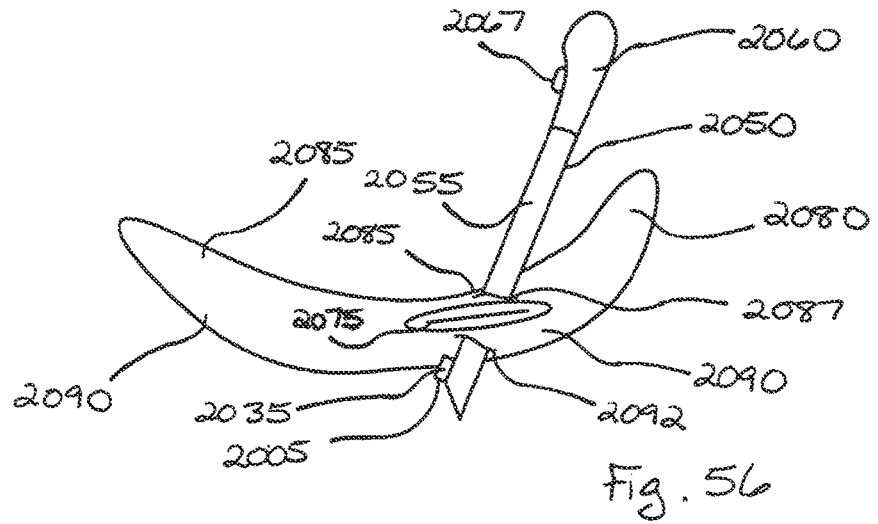
FIGS. 56-58 illustrate a first placement of the surgical device of FIG. 54 in the meniscus to repair a meniscal tear.
Figure 57:
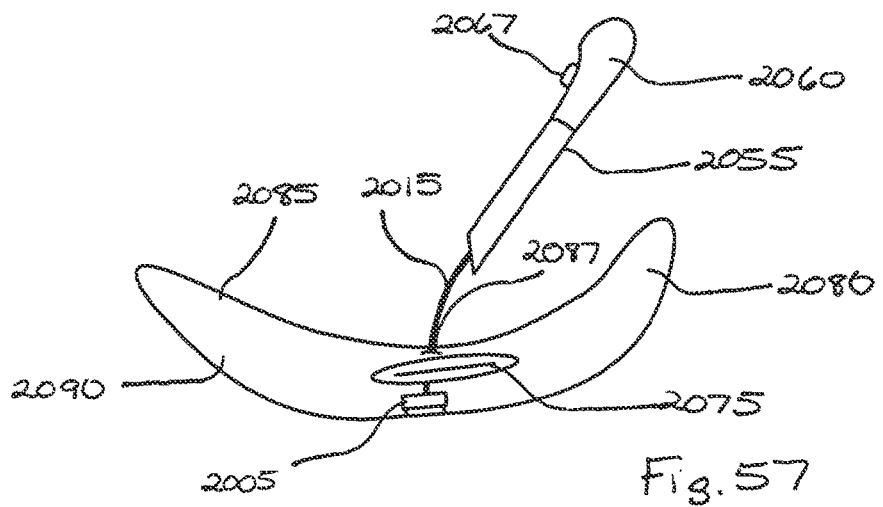
Figure 58:
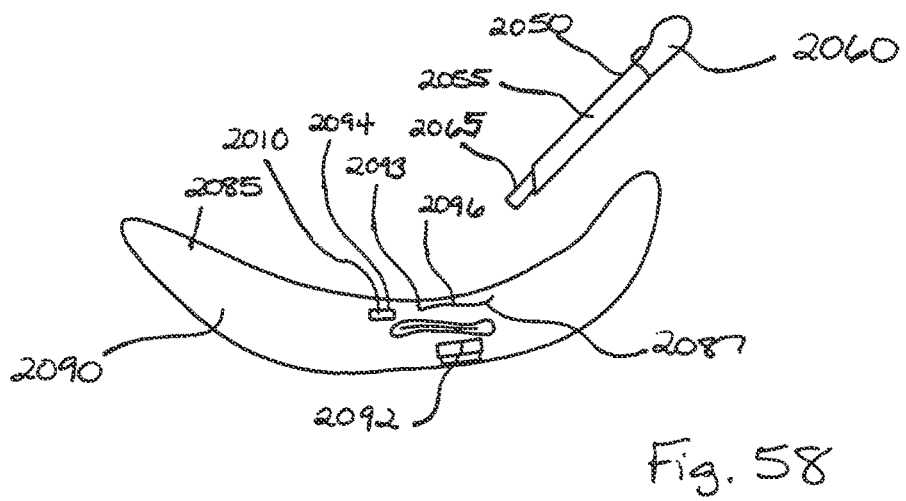

Referring to FIGS. 56-58, the surgical device 2000 and delivery device 2050 are used to repair a meniscal tear 2075. The knee joint is accessed anteriorly and the needle is inserted into an anterior portion 2085 of the meniscus 2080 through a first insertion point 2087 and pushed through the meniscus to a posterior portion 2090 of the meniscus 2080 such that the first fixation member 2005 extends from the meniscus at a first exit point 2092. While pushing the needle through the meniscus, the physician optionally can apply a force to the thumb-activated finger switch 2067 (which is integral with the pusher rod 2065) to prevent tissue from pressing the fin 2035 further back into the needle. Of course, the longitudinal slot 2070 can be fabricated to a length that is slightly longer than the length of the fin 2035 to provide an automatic limitation on the retrograde movement of the first fixation member 2005.

The physician next pulls back on the delivery device 2050 and pulls the needle 2055 out of the meniscus 2080, although not out of the knee joint. The physician then moves the needle 2055 to a second insertion point 2093 adjacent to the first insertion point 2087. The physician then inserts the needle 2055 a second time into the meniscus 2080 from the anterior portion 2085 of the meniscus through the second insertion point 2093 and pushes the needle through the meniscus to the posterior portion 2090 of the meniscus such that the second fixation member 2010 extends from the opposite side of the meniscal tear 2075 at a second exit point 2094. A length 2096 of suture 2015 spans the meniscus between the first insertion point 2087 and the second insertion point 2093. The physician next uses the thumb-activated pusher rod 2065 to dislodge the second fixation member 2010 from the needle 2055.

Proper placement of the second fixation member 2010 relative to the first fixation member 2005 will cause the suture 2015 to be in tension. Proper placement is ensured by setting the second insertion point 2093 far enough from the first insertion point 2087 such that there is little play in the suture prior to placing the second fixation member 2010. As noted above, the fixation members 2005, 2010 are placed such that there is tension in the suture. To relieve some of the tension, the fixation members 2005, 2010 will shift position to be generally perpendicular to the suture 2015. This advantageously limits the likelihood that the fixation members 2005, 2010 will be pulled back into the channels created by the needle during insertion. The tension in the suture 2015 also advantageously apposes the edges of the meniscal tear 2075 to heal the tear.

Figure 59:
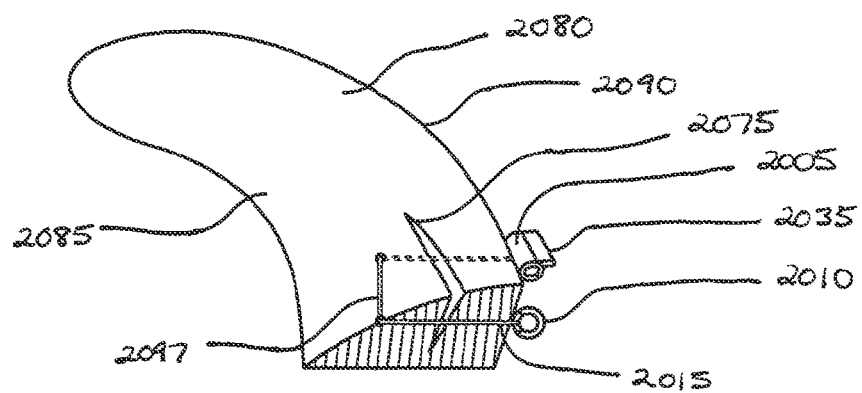
FIG. 59 illustrates a second placement of the surgical device of FIG. 54 in the meniscus to repair a meniscal tear.

Referring to FIG. 59, the surgical device 2000 also can be implanted in a different position relative to the tear than illustrated in FIGS. 56-58. For example, instead of placing the fixation members 2005, 2010 on opposite sides of the meniscal tear 2075, the fixation members 2005, 2010 can be placed on the same side of the tear and the suture 2015 used to appose the edges of the tear. In this positioning of the fixation members 2005, 2010, the needle 2055 is advanced anteriorly to distally through the meniscal tear 2075, the first fixation member 2005 placed, and the needle 2055 withdrawn. The physician next moves the needle 2055 laterally to create a length 2097 of suture that extends along the anterior surface 2085 of the meniscus. The needle 2055 then is advanced anteriorly to distally through the meniscal tear 2075, the pusher rod 2065 advanced to dislodge the second fixation member 2010, and the needle withdrawn. Again, the tension in the suture 2015 causes the fixation members 2005, 2010 to shift to be perpendicular to the suture. The tension in the suture tends to pull the fixation members 2005, 2010 in the direction of the length 2095 of suture that extends along the meniscus, which apposes the edges of the meniscal tear.

Depending on the size of the tissue wound, three or more fixation members can be used in the devices discussed above. The additional fixation members can be pulley retainers, can be similar to the second fixation member, or can be both additional pulleys and additional second retainers.

The wound closure and repair devices discussed above need not be deployed using a needle, and need not be deployed arthroscopically. Instead, a surgeon can place the fixation members against the tissue during an open procedure.

The wound closure and repair devices discussed above can be used to repair tissue wounds other than meniscal tears. For example, the devices can be used to repair tears in skin, muscles, and ligaments, and to re-attach tissue to support structures, such as bones.

Figure 60:
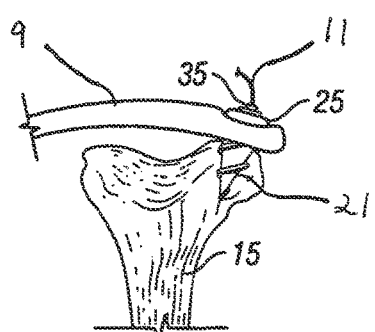
FIG. 60 is a surgical device attaching soft tissue to bone.
Figure 61:
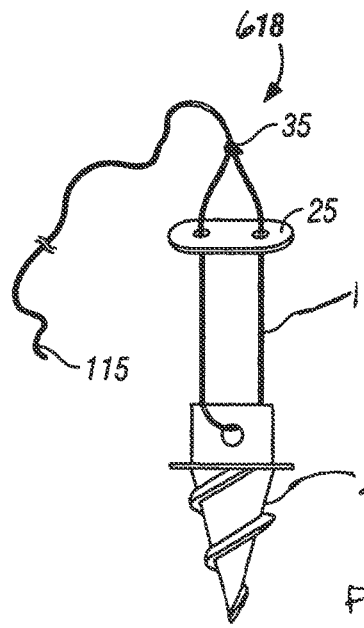
FIG. 61 is a fastener, a suture, and a fixation member of the device of FIG. 60.

Referring to FIGS. 60 and 61, a surgical device 618 is used for reattaching soft tissue, for example, tendon, ligament, or cartilage 9, that is torn partially or completely from a bone 15, to the bone 15, includes a fixation member such as a fastener 21, a fixation member such as a retainer 25, and a flexible member, such as a suture 11. The suture 11 couples the fastener 21 and the retainer 25, and is tied in a limiting element such as a slip knot 35 such that the distance between the fastener 21 and the retainer 25 can be shortened by pulling on a free end 115 of the suture 11. The retainer 25 is positioned between the slip knot 35 and the fastener 21 such that, when the surgical device 618 is implanted, the slip knot 35 is positioned against the retainer 25, as illustrated in FIG. 60.

Figure 62:
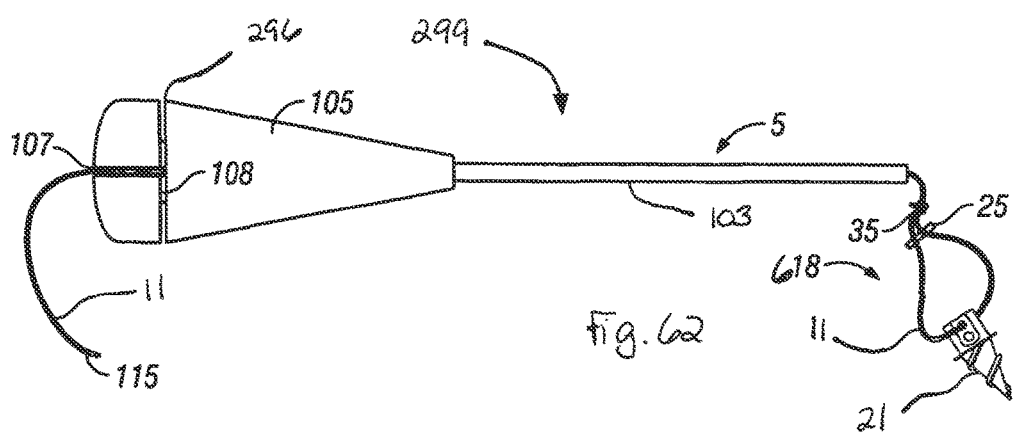
FIG. 62 is a side view of the device of FIG. 1 and a delivery device for delivering the surgical device to a surgical site.

Referring to FIG. 62, a surgical assembly 5 includes the surgical device 618 and a delivery device 299. The delivery device 299 includes a handle 105 and a cannula 103, and is configured to receive the fastener 21, the retainer 25, and the suture 11. The suture 11 passes through the cannula 103 and the handle 105. The handle 105 includes a circumferential slot 296, a longitudinal slot 107, and a connecting member 108 that connects the handle 105 to the cannula 103. When the fastener 21, the retainer 25, and the suture 11 are received in the cannula 103, the suture 11 is passed out of the handle 105. To ensure that the fastener 21 and the retainer 25 remain within the cannula 103 prior to use, the physician pulls the suture 11 through the longitudinal slot 107 until the suture 11 is within the circumferential slot 296 and then wraps the suture 11 around the connecting member 108. In this manner, the fastener 21 and the retainer 25 cannot be withdrawn from the cannula 103 without first loosening the suture 11 from the connecting member 108.

Figure 63:
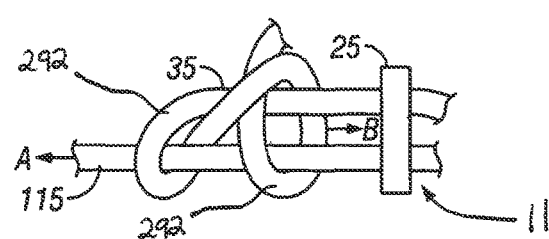
FIG. 63 is a perspective view of a slip knot in the suture of the surgical device of FIG. 60.
Figure 69:
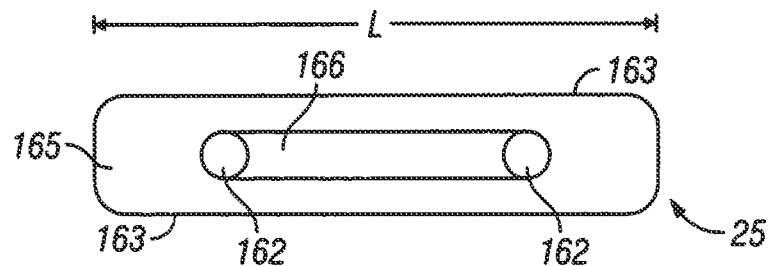
FIGS. 69-72 are top, bottom, side, and end views, respectively, of the fixation member of the surgical device of FIG. 60.
Figure 70:
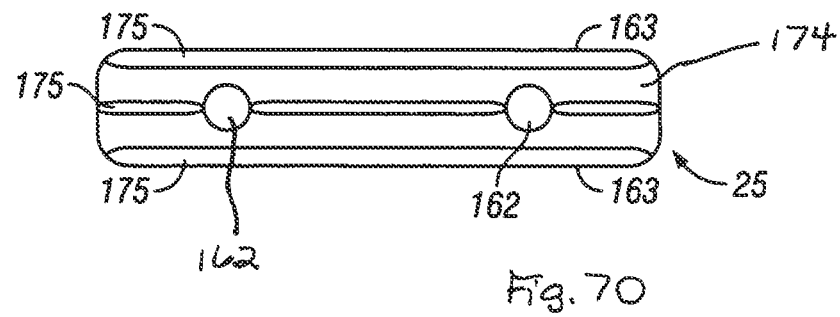
Figure 71:
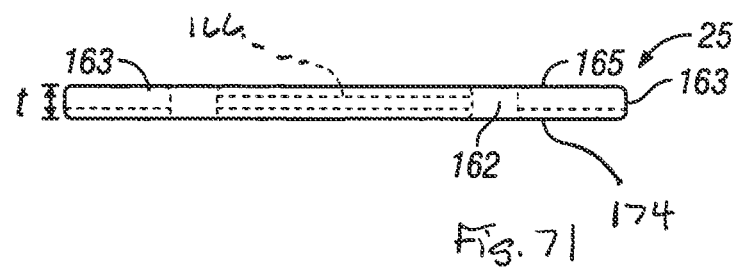
Figure 72:
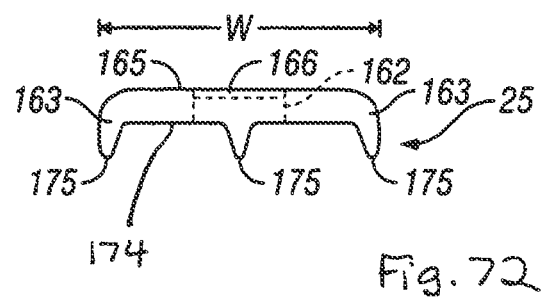
Figure 73:
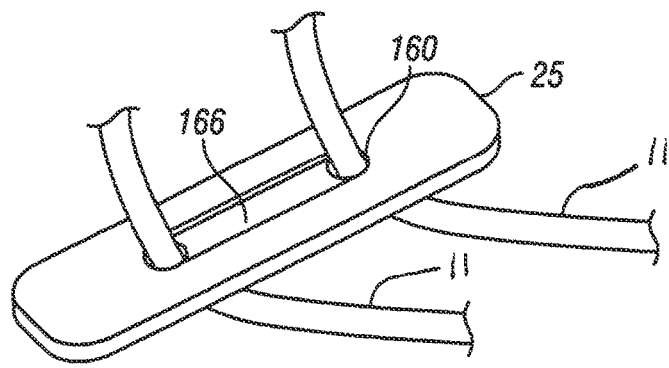
FIG. 73 is a perspective view of the fixation member illustrating the passage of the suture through channels or openings in the fixation member.

Referring to FIG. 63, the suture 11 is tied in a slip knot 35 or other type of movable attachment or knot. The movable attachment of the suture 11 to the retainer 25 is one-way such that the length of the suture 11 between the fastener 21 and the retainer 25 can be shortened, but not lengthened. The slip knot 35 is formed, for example, by using the suture 11 to make one or more loops 292 around itself and then tightening the loops 292 against the segment of suture 11 that they encircle. As illustrated in FIGS. 62 and 63, the suture 11 extends from the slip knot 35, through the retainer 25, through the fastener 21, back through the retainer 25, and through the slip knot 35. If the fastener 21 is in a fixed position, such as within bone 15, pulling the free end 115 of the suture 11 in a first direction A pulls the slip knot 35 along the suture 11 in a generally opposite direction B, which is in the direction of the fastener 21. As long as the free end 115 is pulled, the slip knot 35 will continue to slide along the suture 11 in the direction B until the slip knot's movement is obstructed by the retainer 25. In one application of the surgical device 618, the slip knot's movement is obstructed by the retainer 25 when soft tissue 9 is compressed between the retainer 25 and the fastener 21.

As shown in FIG. 60, the surgical assembly 5 is generally used, for example, to reattach tissue torn from bone, by placing the fastener 21 through the tissue and into bone, and then tightening the slip knot 35 to push the retainer 25 against the torn tissue. In this manner, the tissue is forced against the bone and the torn edge of the tissue may be placed in apposition to promote healing and prevent further trauma to the tissue.

Referring to FIGS. 64 and 65, the fastener 21 is, for example, a screw including a head 135 and a shank 291 with threads 145. The head 135 is shaped to mate with the cannula 103. For example, the outer surface 146 of the head 135 has a hexagonal shape and the cannula 103 has a hexagonally shaped opening 155 (FIG. 67) that receives the head 135. The head 135 is separated from the shank 291 by a ridge 147 for purposes discussed below. The head 135 includes one or more openings 290 through which one or more sutures 11 pass. Generally, only one suture will be used and therefore only one of the openings 290 will include a suture 11 passing through it. Nonetheless, one or more sutures 11 can be passed through each opening 290 and couple to one or more retainers 25. The threads 145 are of any configuration, such as a set of parallel threads of different pitch, angle, and/or diameter.

The fastener 21 can be made of a biocompatible metal, polymer, or bioabsorbable polymer, such as titanium, stainless steel, polyethylene, polypropylene, polyglycolic acid, or polylactic acid. The can be made by one or more of many methods, including, for example, machining, molding, casting, or cutting. Alternatively, the fastener 21 can be a push-in type fixation member such as described in the Hayhurst patent, supra.

Referring also to FIGS. 66-68, the hexagonal opening 155 for receiving the screw head 135 is at the distal end 156 of a lumen or longitudinal channel 157 having a hexagonally shaped bore 159 that extends between the hexagonal opening 155 and a proximal hexagonal opening 297 of the cannula 103. The lumen 157 extends from the cannula 103 through the handle 105 and terminates at an opening 161. The suture 11, the slip knot 35, the retainer 25, and the head 135 of the fastener 21 are placed within the cannula lumen 157 with the slip knot 35 placed proximal to the retainer 25 and the head 135 of the fastener 21 placed distal to the retainer 25. The threaded shank 291 of the fastener 21, however, is not positioned within the cannula lumen 157 but instead extends beyond the cannula 103. The free end 115 of the suture 11 passes out of the proximal opening 161 in the handle 105 such that the physician can grasp the suture 11 and gently pull on the suture 11 to apply tension to the suture 11. Pulling on the suture 11 applies tension to the suture 11 because the ridge 147 prevents the physician from pulling the fastener 21 further into the lumen 157. By applying tension to the suture 11, the physician ensures that the fastener 21 will not accidentally fall out of the lumen 157 during delivery of the surgical device.

When the suture 11, the slip knot 35, the retainer 25, and the head 135 are positioned in the lumen 157, the retainer 25 and the fastener 21 are separated by a tube or block 358 of a rapid absorbing material, such as thrombin, a dry salt, or dry saline. The tube 358 provides a separation between the fastener 21 and the retainer 25 such that the fastener 21 can be delivered without the retainer 25 accidentally being removed or otherwise dislodged from the cannula lumen 157 with the fastener. If the separation between the fastener 21 and the retainer 25 is not sufficient, when the physician delivers the fastener 21 the retainer 25 may be dislodged from the lumen 157. The tube 358 also can be used as a drug or therapeutic agent delivery device to provide a drug or therapeutic agent to the surgical site. For example, the tube 358 includes a wound healing agent, an anti-bacterial agent, or an anti-inflammatory agent. The tube 358 is expelled from the cannula 103 when the retainer 25 is advanced forward in the cannula 103, as described below.

The suture 11 is made of any suture material, such as, for example, polyethylene or polypropylene. The handle 105 and the cannula 103 likewise are made of a biocompatible polymer such as, for example, polyethylene or polypropylene, or a biocompatible metal, or a combination of these.

Although the absorbable tube 358 is described as being pulled from the needle and/or cannula by the tension in the suture as the suture pulls on the adjacent retainer or screw, the absorbable tube can include a barb or other protrusion to actively catch onto tissue and fix the position of the tube 358 when the cannula or needle is withdrawn.

As illustrated in FIGS. 69-73, the retainer 25 includes one or more channels or openings 162, sides 163, an upper surface 165, and a lower surface 174. The channels or openings 162 receive the suture 11 and therefore are smooth or tapered to limit any sharp edges that could damage the suture. The sides 163 and the upper surface 165 likewise are smooth to provide atraumatic tissue contacting surfaces. Passing between the channels 162 on the upper surface 165 is a groove 166 such that when the slip knot 35 is tightened the suture 11 is recessed in the groove 166. In this manner, less of the suture 11 is exposed to mechanical forces associated with body movement. The lower surface 174 preferably includes one or more longitudinally-oriented protrusions 175 that contact the tissue being reattached when the retainer 25 is implanted. The protrusions 175 provide traction against the tissue to limit movement of the retainer 25 relative to the tissue.

The retainer 25 has a low profile to limit protrusion from the soft tissue 9 so that the retainer 25 does not extend from the soft tissue surface, for example, to avoid impingement against other tissue surfaces. For example, if the low profile retainer 25 is used to repair the rotator cuff, the thickness of the retainer 25 is selected to prevent impingement of the retainer 25 against the bony surface of the accromium. Other considerations that can be used in determining the thickness of the retainer 25 include (1) the strength of the retainer relative to the suture passing through the retainer, (2) the depth into the soft tissue that the retainer is seated, and (3) the cosmetic appearance caused by protrusion against the skin (for example, repair of the lateral collateral ligament). In general, the low profile retainer has dimensions that prevent protrusion of the retainer beyond the tissue in which it is placed. Although some protrusion beyond the overall surface of the soft tissue is satisfactory, if the low profile retainer is positioned flush with the overall surface of the soft tissue (for example, by tightening the slip knot against the retainer to bury the retainer into the soft tissue) there is a reduced likelihood of impingement and/or contact with other tissue surfaces.

With respect to determining the thickness of the retainer 25 based on the strength of the suture, the thickness can be determined such that the retainer 25 has the same approximate strength as the suture. The principle behind this consideration is that the retainer 25 does not inherently need to have an increased thickness and, as such, one guide to determining thickness is to provide the minimum thickness necessary to have a similar strength as the suture. In this manner, the retainer 25 provides adequate strength without protruding too much. With respect to the cosmetic appearance caused by the retainer 25, if the retainer is implanted close to the skin surface, a relatively thin retainer would protrude less from the skin than a relatively thick retainer. As such, the recipient of the retainer is less likely to notice the retainer or to find the retainer to be a source of irritation.

For example, in one implementation, the retainer 25 has a thickness, t, of between approximately 0.5 and 2.5 mm and, preferably, approximately 2 mm. The length, l, of the retainer 25 is between approximately 6 mm and 10 mm and, preferably, approximately 8 mm. The width, w, of the retainer 25 is between approximately 1.5 and 3 mm and, preferably, between approximately 2 mm and 2.5 mm.

Figure 74:
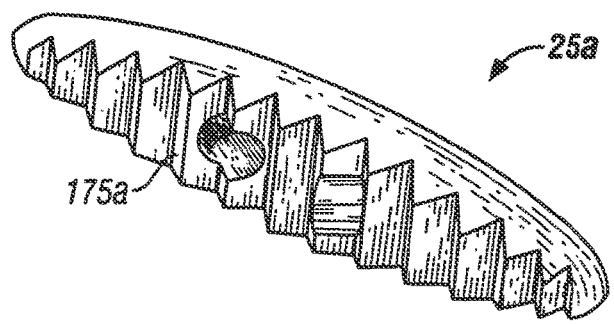
FIGS. 74-76 are perspective bottom, perspective top, and cross-sectional side views, respectively, of an alternative embodiment of a fixation member having a tissue contacting surface with protrusions.
Figure 75:
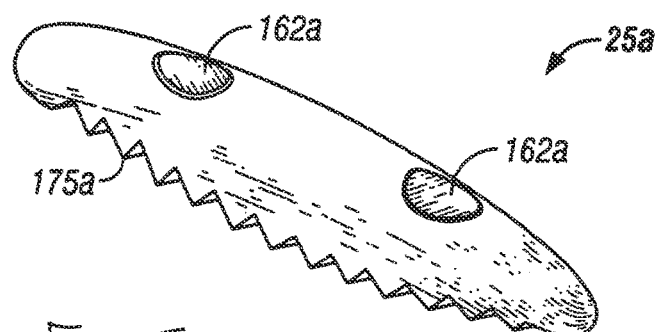
Figure 76:
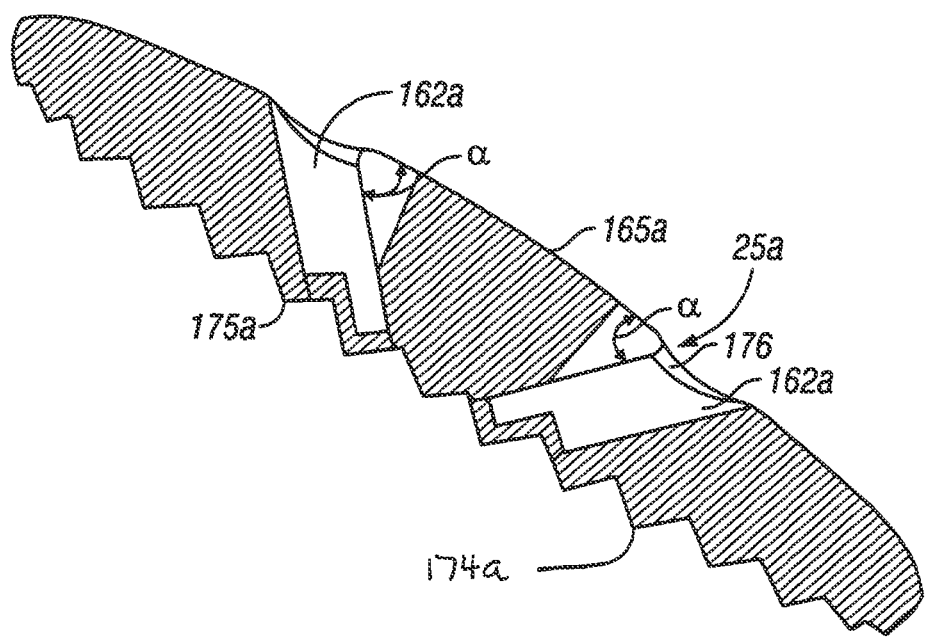

Referring to FIGS. 74-76, in an alternative implementation, a retainer 25a is a low profile implant that has a lower surface 174a with transverse protrusions 175a. The protrusions 175a provide traction against a tissue to limit movement of the retainer 25a relative to the tissue. The retainer 25a has two channels 162a extending between a generally smooth upper surface 165a and the lower surface 174a. The channels 162a are oppositely oriented at an angle, α, to surfaces 165a, 174a. The angle, α, is between about 30° and 60°. By angling the channels 162a, the force vector associated with the sutures 11 passing through the channels 162a is optimized to achieve optimal repair stability when used with the slip knot 35. In particular, by angling the channels 162a, the slip knot 35 has a reduced likelihood of loosening because the suture 11 on the upper surface 165a is under tension in a different direction than that of the suture 11 that passes through the channels 162a. Angling the channels 162a also beneficially causes the two lengths of suture 11 that pass from the retainer 25a to the fastener 21 to be adjacent to each other. By keeping the two lengths of suture 11 adjacent to each other, the channel through the soft tissue through which the suture 11 passes is smaller than it would be if the two lengths of suture were spread apart. Finally, the channels 162a have a tapered opening 176 to accommodate suture 11 passing through the openings 162a and resting against the smooth upper surface 165a. The tapered openings 176 limit damage to the suture 11 that can be caused by sharp edges.

Figures 77, 78:
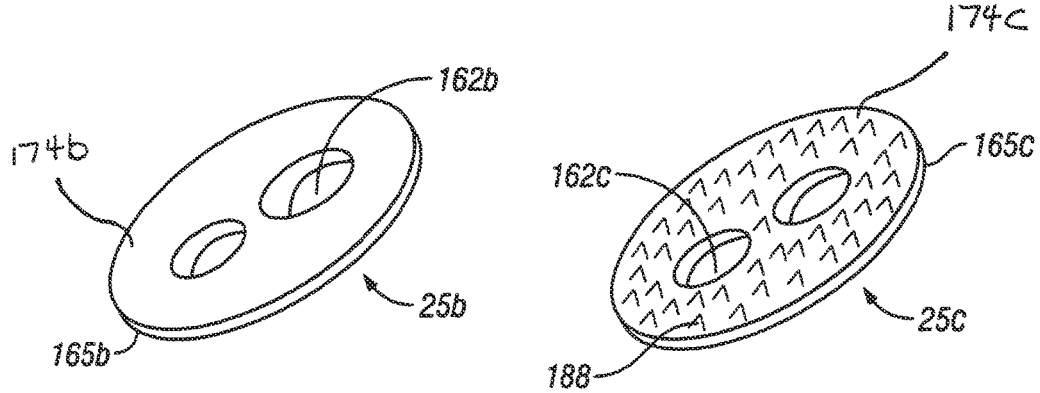
FIG. 77 is a perspective bottom view of an oblong fixation member having a smooth bottom surface.
FIGS. 78-80 are perspective bottom views of oblong fixation members having bottom surfaces with protrusions.
Figures 79, 80:
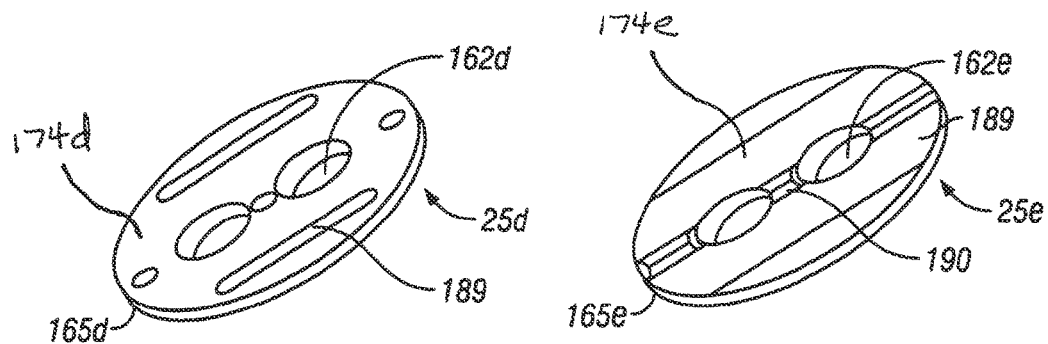

Referring to FIGS. 77-80, less oblong shaped retainers 25b, 25c, 25d, and 25e include an upper surface 165b, 165c, 165d, 165e, a lower surface 174b, 174c, 174d, 174e, and channels 162b, 162c, 162d, 162e, respectively, through the retainer 25b, 25c, 25d, 25e. Referring to FIG. 77, the lower surface 174b and/or the upper surface 165b are smooth. Referring to FIG. 78, the lower surface 174c has protrusions in the form of dimples 188. Referring to FIG. 79, the lower surface 174d has protrusions in the form of ridges 189. Referring to FIG. 80, the lower surface 174e has protrusions in the form of ridges 189 and teeth 190. The channels 162b, 162c, 162d, and 162e are angled relative to the surface 174 and also have a tapered or flared opening as described with respect to FIGS. 74-76.

The retainers 25 and 25a-e are made of a bioabsorbable material, a biocompatible plastic, or a biocompatible metal and are made using any well-known technique, including, for example, injection molding, casting, machining, cutting, and stamping. They can be coated with a therapeutic material that, for example, promotes healing of torn tissue and/or prevents infections.

Referring again to FIG. 68, the delivery device 299 is loaded with the suture 11, the retainer 25, and the fastener 21 in the opposite order in which these items are deployed. The tube or block 358 is optionally inserted between the retainer 25 and the fastener 21. The free, proximal end 115 of the suture 11 is inserted into the open, distal end 156 of the cannula 103 and threaded through the lumen 157 until the free, proximal end 115 extends through the proximal opening 161 of the handle 105. The slip knot 35 followed by the retainer 25 is manipulated into the lumen 157 while gently pulling the proximal end of the suture 11. The tube 358 is then inserted into the lumen 157. In the last step, the head 135 is positioned within the bore 159 of the lumen 157 until the ridge 147 is pressed against the distal end 156 of the cannula 103. The proximal end 115 of the suture 11 is then given a final gentle pull to ensure that the fastener 21 is securely positioned within the lumen 157.

Figure 81:
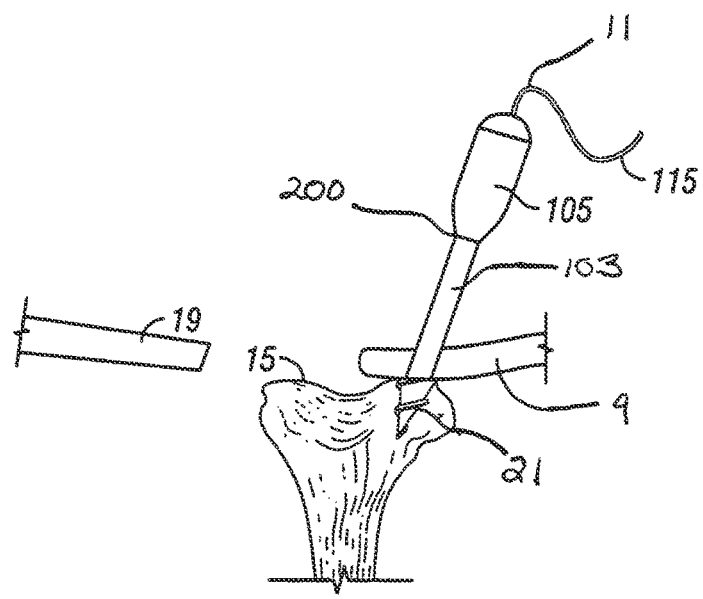
FIGS. 81-84 illustrate an arthroscopic procedure to repair a rotator cuff injury using the device of FIG. 62.

Referring to FIG. 81, the surgical assembly 5 is used in an arthroscopic procedure with an arthroscope 19 to repair, for example, a rotator cuff injury. In this procedure, two small incisions are made into the shoulder joint and the arthroscope 19 is inserted through one incision and the delivery device 299 is inserted through the second incision. The delivery device 299 optionally is placed through a cannula in the second incision. The arthroscope 19 provides a video means of viewing the inside of the shoulder joint throughout the procedure. Prior to inserting the delivery device 299, the physician initially removes any unhealthy or degenerated rotator cuff tissue. Then, the physician prepares the area of the humerus bone 15 where the tendon 9 tore away from the bone 15. For example, the physician gently roughens the bone's cortex to enhance healing by decorticating the cortical surface of the bone to prepare a fresh bed or bleeding surface to encourage tissue to heal. The decortication of the bone results in a slight trough, known as a decorticated trough, to which the tendon is attached.

Following the initial preparatory work, the physician passes the delivery device 299 through the tendon tissue 9 until the fastener 21 is in contact with the bone 15. The physician then screws the fastener 21 into the bone 15 by grasping the handle 105 and rotating it. The fastener 21 has either left-handed or right-handed threads and the physician rotates the handle in the appropriate direction based on the threads to insert the fastener 21 into the bone 15. Because the cannula 103 has the hexagonal bore 159 and the fastener 21 has the hexagonal head 135, rotating the handle transfers the rotational force to the head 135 and fastener 21 and thereby screws the fastener 21 into the bone tissue.

Figure 82:
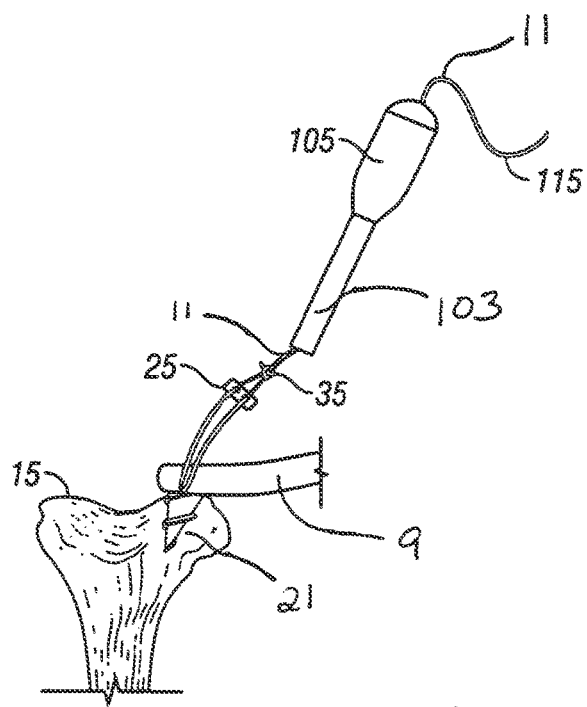

As illustrated in FIG. 82, the physician then withdraws the delivery device 299 from the tendon 9. Because the fastener 21 is inserted into the bone 15, withdrawing the delivery device 299 pulls the suture 11, the slip knot 35, and the retainer 25 out of the lumen 157. If the physician has inserted the tube 358 into the cannula 103, the tube 358 is also pulled out of the cannula 103 when the retainer 25 is pulled out.

Figure 83:
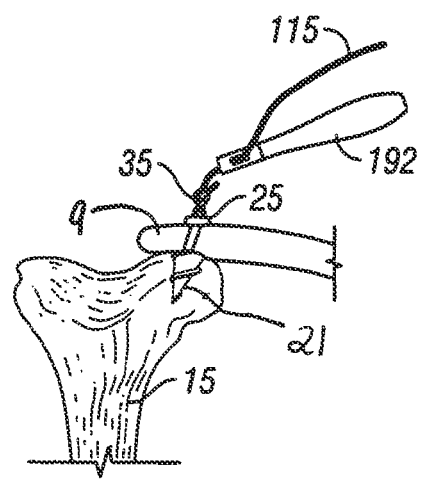

Referring to FIG. 83, the physician then threads the free end 115 of the suture 11 through a knot pusher 192, advances the knot pusher 192 over the suture 11 to slip knot 35, and, while pulling the free end 115, pushes the slip knot 35 against the retainer 25, and presses the retainer 25 and the slip knot 35 against the tendon tissue 9 to firmly position the tendon 9 against the bone 15. The knot pusher can be, for example, the knot pusher component of the Smith & Nephew FasT-Fix Meniscal Repair System (Smith & Nephew, Andover, Mass.).

Figure 84:
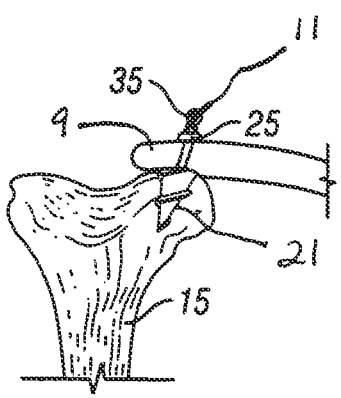

Referring to FIG. 84, the physician then cuts the suture 11 at a position adjacent to the slip knot 35. After examining the repair through the arthroscope, the physician determines whether additional tissue repair is necessary and, if so, places one or more additional fasteners 21 and retainers 25.

Referring to FIGS. 85-89, in another implementation, a surgical assembly 261 includes a delivery device 267 and a surgical device 205. The surgical device 205 includes the fastener 21, the suture 11, and the slip knot 35 of FIG. 60, and, rather than a single retainer, a pair of low-profile retainers 208a, 208b. One or more absorbable tubes 358 are between the retainers 208a and 208b, and between the distal retainer 208a and the fastener 21. The delivery device 267 and the surgical device 205 are used in procedures in which there is, for example, insufficient tissue to grasp or poor quality tissue such that a single fastener 21 and retainer 25 would not adequately reattach the tissue 9 to the bone 15. As described in more detail below, using the surgical device 205 allows the physician to bridge a gap between an area of poor or insufficient tissue and an area of better quality tissue and pull the better quality tissue in the direction of the fastener 21 to attach the better quality tissue to the bone 15. For example, there may be insufficient tissue to grasp when the patient's shoulder is in abduction and there is not sufficient space to manipulate the delivery device 267 to deliver the retainers 208a, 208b through the tissue. There also may be poor quality tissue and insufficient tissue to grasp when the tear has a frayed end that must be trimmed. There may be poor quality tissue when the patient is elderly and the tissue has degenerated. In these situations, the surgical device 205 is used to bridge the gap between the better quality tissue and the bone to which the tissue is to be attached. The pair of retainers 208a, 208b also beneficially helps to distribute the load on the suture 11.

The delivery device 267 includes a handle 210, a cannula 215, and a retractable needle 263. The needle 263 includes a thumb pad 211 at the proximal end 269 of the needle 263 and a sharpened tip 233 at the distal end 271 of the needle 263. The thumb pad 211 protrudes out of an open region 231 in the handle 210 to provide access to the thumb pad 211 for the surgeon to advance or retract the needle 263. The open region 231 is configured to be slightly wider than the thumb pad 211 such that the thumb pad 211 will slide within the open region 231 with minimal lateral play. The open region 231 has a length, 1, that provides sufficient play for the needle 263 to be fully extended by moving the thumb pad 211 in one direction, arrow A, and completely retracted by moving the thumb pad in the opposite direction, arrow B.

Figure 93:
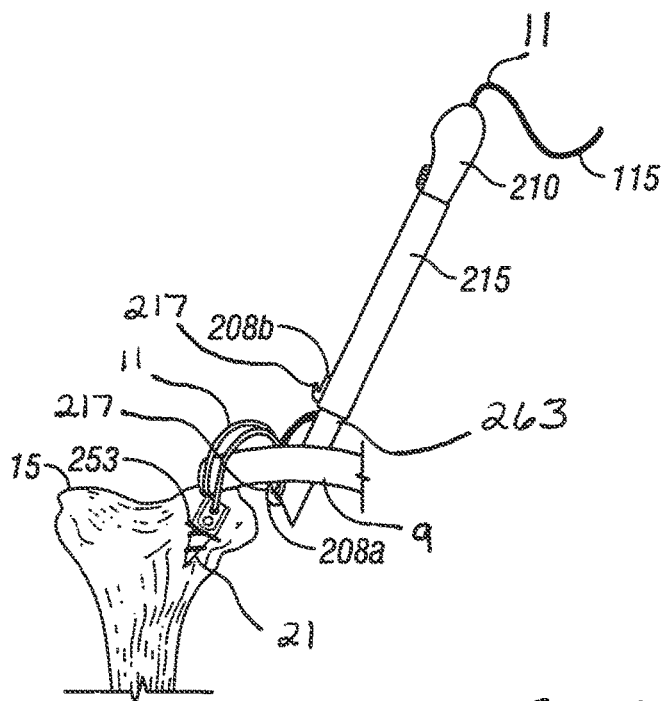

The needle 263 includes a longitudinal slot 235 that opens into a channel 213 defined within the needle 263. The needle 263 slides within a lumen 245 of the cannula 215 and can be advanced to extend distally from the cannula 215 or can be retracted to be wholly contained within the cannula 215. As described in more detail below, the retainers 208a, 208b are positioned within the channel 213 because to deliver the retainer 208a, the needle 263 is extended to pass through the soft tissue. Like the needle 263, the cannula 215 includes a slot 241 that opens into the lumen 245. The physician positions the suture 11 such that it passes through the slots 241, 235 rather than passing over the sharpened tip 233 of the needle 263, thereby preventing the sharpened tip 233 from damaging the suture 125 (FIG. 93). As described in more detail below, the purpose of the needle 263 is to create an opening to pass the cannula 215 through the tissue 9 to place the retainers 208a, 208b. Because the suture 11 is passed through the slots 241, 235, the suture 11 will not pass over the sharpened tip 233 and thereby be cut by the sharpened tip 233 when pressing the sharpened tip 233 against the tissue 9 to create the opening with the needle 263. Thus, one purpose of the slots 235, 241 is to provide a location in which to pass the suture 11 such that the suture 11 is away from the sharpened tip 233.

The retainers 208a, 208b each include a barb or protrusion 217 that extends from a surface 251 of the retainer 208a, 208b and passes through the slots 235, 241. As described in more detail below, the barb 217 catches on the tissue 9 when the delivery device 267 is being withdrawn. By catching the tissue 9, the barb 217 acts to withdraw the retainer 208a from the needle 263 and cannula 215.

Figure 90:
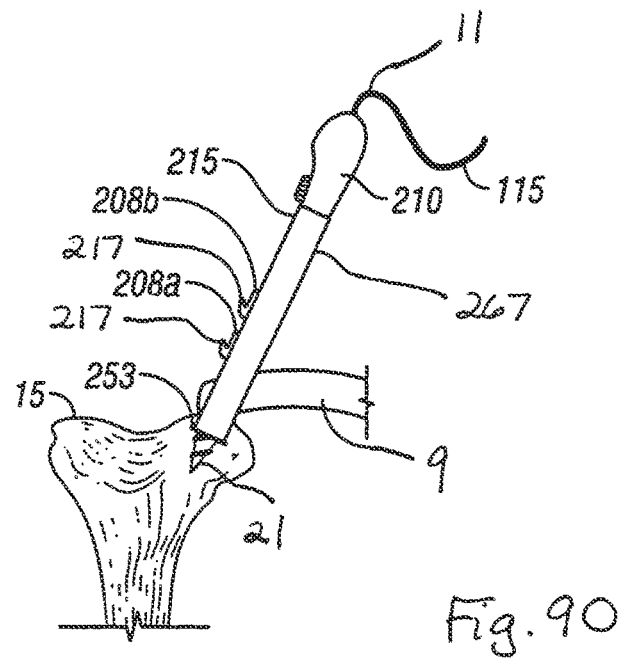
FIGS. 90-97 illustrate a tissue repair procedure using the surgical assembly of FIG. 85.

As illustrated in FIG. 90, the delivery device 267 is used to reattach soft tissue to bone in, for example, the rotator cuff. Initially, the surgical site is prepared as described above, including the physician forming a decorticated trough 253. The physician then passes the cannula 215 and the fastener 21 through the tendon tissue 9 until the fastener 21 is in contact with the bone 15. In the same manner as described above, the physician inserts the fastener 21 into the bone 15 by grasping and rotating the handle 210. In particular, because the lumen 245 of the cannula 215 is shaped, for example, to have a hexagonal shape, and the fastener 21 has the mating hexagonal head 135, as described above with respect to FIGS. 66-68, rotating the handle transfers the rotational force to the head 135 and the fastener 21 and thereby screws the fastener 21 into the bone tissue 15. FIG. 90 illustrates a situation in which there is an insufficient amount of tendon tissue 9 that is accessible by the physician, and the physician has inserted the fastener 21 through the tendon tissue 9 into the decorticated trough 253 approximately where he or she wants to reattach the tendon tissue 9. As described below, subsequent placement of the pair of retainers 208a, 208b, further away from the tear, pulls the better quality tendon tissue 9 into the decorticated trough 253 to reattach the tissue 9 to the bone 15.

Figure 91:
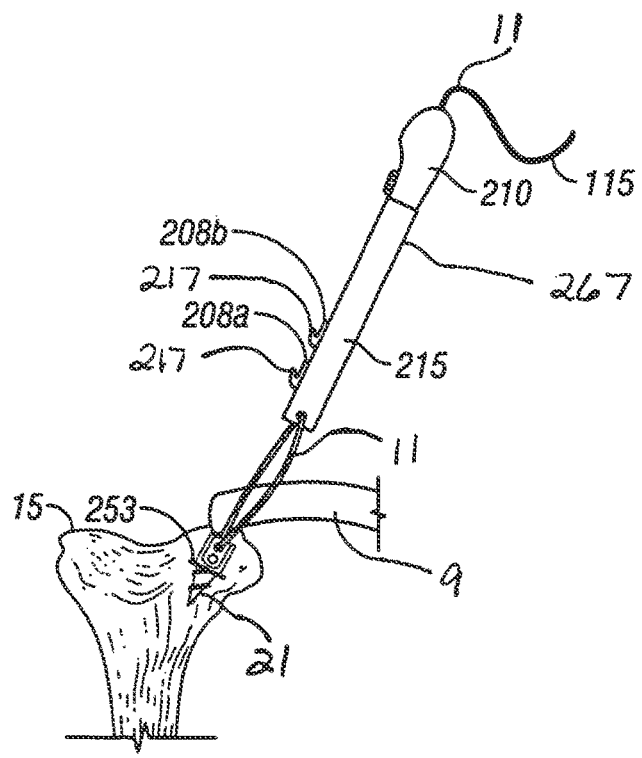
Figure 92:
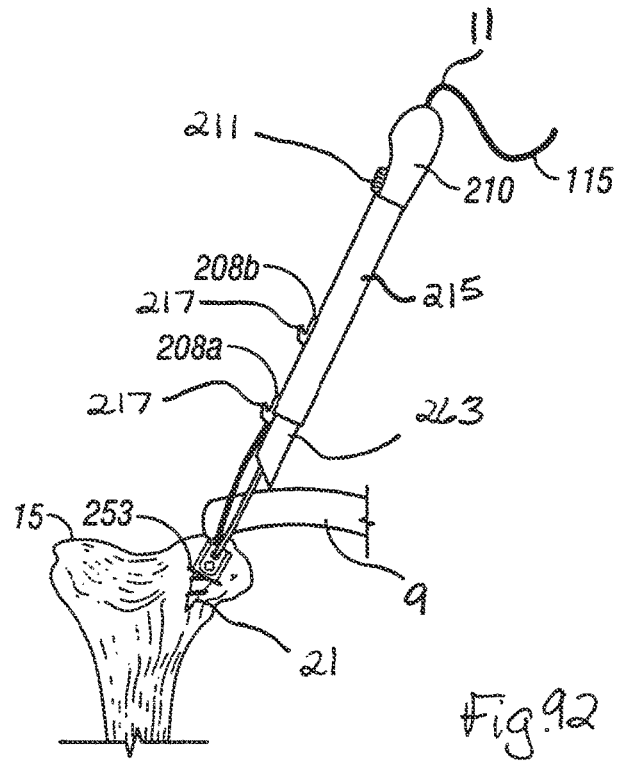

As illustrated in FIG. 91, the physician then withdraws the delivery device 267 from the tendon tissue 9, leaving the fastener 21 in the bone 15. At this step, the suture 11 passes from the fastener 21 through the tendon tissue 9 to the retainer 208a. Referring to FIG. 92, the physician then advances the retractable needle 263 out of the cannula 215 by pushing the thumb pad 211 from its retracted position to its extended position. To avoid having the suture 11 extending from the delivery device 267 such that it is surrounded by the sharpened tip 233, the physician changes the position of the suture 11 relative to the sharpened tip 233 such that it passes through the slots 235, 241. For example, the physician can gently grasp the free end 115 of the suture 11 and apply tension to the suture 11 while slightly rotating the handle 210 around its longitudinal axis until the suture 11 moves along the circumference of the sharpened tip and enters the slots 235, 241.

To manipulate the suture 11 through the slots 235, 241, the physician can instead rotate the handle 210 until the suture 11 is lined up with the slots 235, 241. By advancing the delivery device 267 and extending the needle 263 such that the suture 11 passes into the slots 235, 241, the physician clears the suture 11 away from the sharpened tip 233. The physician then positions the sharpened tip 233 of the needle 263 against the tendon tissue 9 with the suture 11 moved away from the sharpened tip 233. In this position, the suture 11 is not between the sharpened tip 233 and the tendon tissue 9 and will not thereby be damaged (for example, cut by the sharpened tip 233) when the needle is pressed into the tendon tissue 9. The physician places the needle 263 adjacent to the better quality tendon tissue 9.

Referring to FIG. 93, the physician grasps the handle 210 and pushes the delivery device 267 in the direction of the tendon tissue 9 to drive the needle 263 through the tendon tissue 9 until the first barbed retainer 208a has completely passed through the tendon tissue 9. In particular, the barb 217 of the retainer 208a is positioned within or through the tendon tissue 9. The suture 11 now extends from the fastener 21 through the tendon tissue 9, and back into the tendon tissue 9 to the retainer 208a and back to the delivery device 267.

Figure 94:
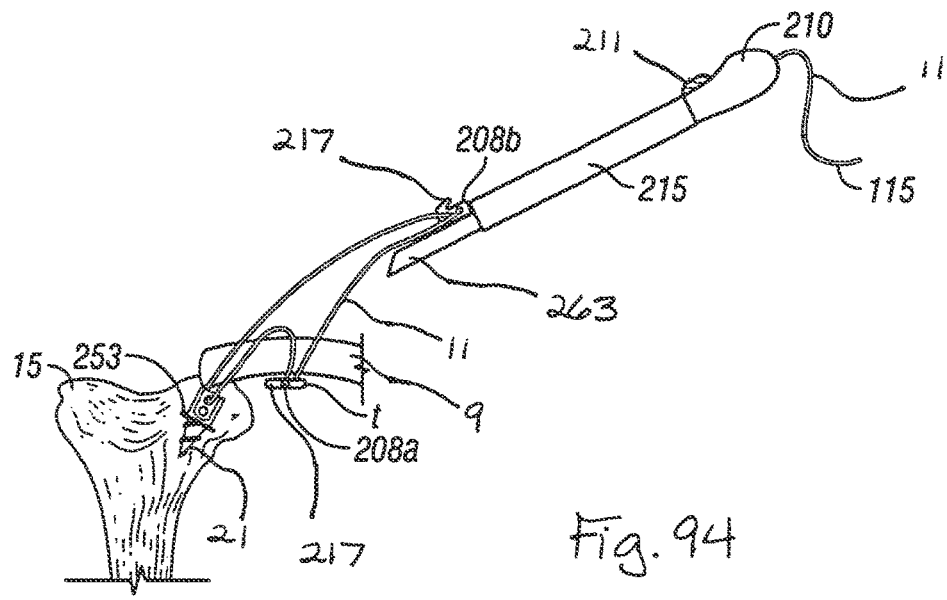
Figure 95:
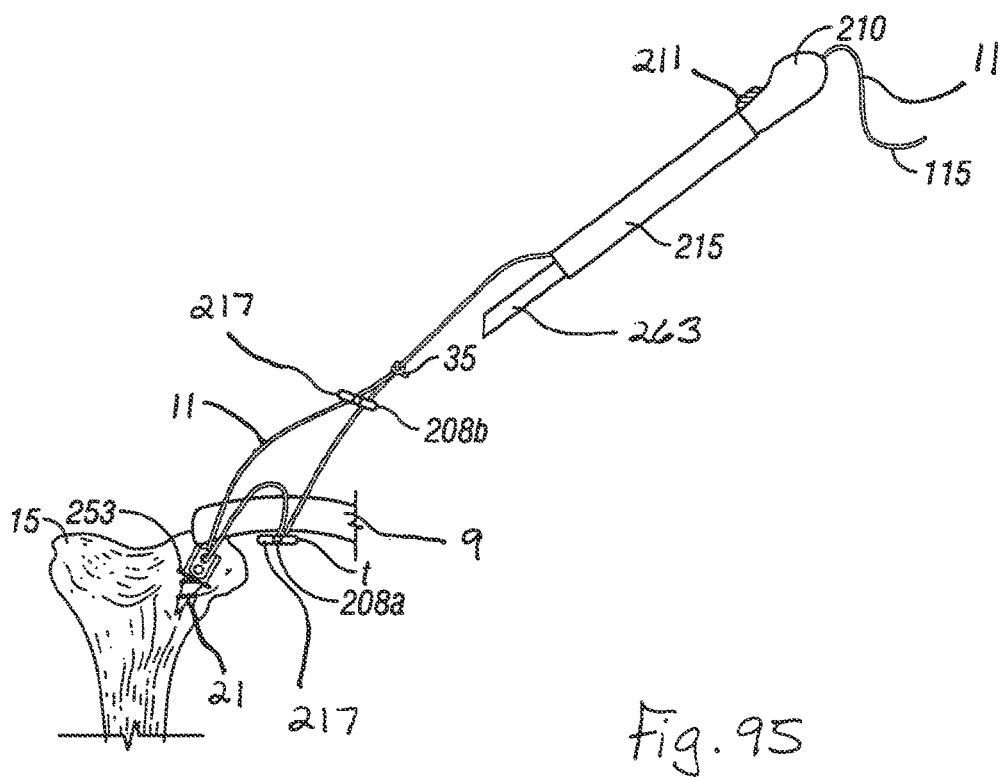

Referring also to FIGS. 94 and 95, the physician withdraws the needle 263 after placing the first retainer 208a. By withdrawing the needle 263, the barb 217 catches the tendon tissue 9 and remains caught against the tendon tissue 9 after the needle 263 is withdrawn. The first retainer 208a is flush against the tendon tissue 9, or alternatively, within the tendon tissue 9. As the physician further withdraws the needle 263, tension in the suture 11 pulls the second retainer 208b and the slip knot 35 out of the needle 263.

Although both retainers 208a, 208b are illustrated as having the barb 217, it is not necessary in all circumstances to provide the second retainer 208b with a tissue-catching member such as the barb 217. Because the first retainer 208a is positioned against the tissue 9, withdrawing the needle 263 from the first retainer 208a causes tension in the suture 11 that pulls the second retainer 208b from the needle 263 without the barb 217 being used. However, to reduce manufacturing costs and inventory costs, for example, the second retainer 208b can be barbed such that it is the same part as the first retainer 208a.

Moreover, the barb 217 can be made of a bioabsorbable material such that it is absorbed by the tissue and does not remain as a potential tissue irritant. The bioabsorbable materials can include a therapeutic agent to treat the injury, promote healing, or provide a preventative anti-bacterial effect. If the physician has placed an absorbable tube 358 between the fastener 21 and the first retainer 208a, when the physician withdraws the needle 263, the tube 358 also is pulled out of the needle 263 by the interaction of the retainer 208a and the tissue 9 such that the tube 358 is positioned in proximity to the first retainer 208a. If the physician has also placed an absorbable tube 358 between the two retainers 208a, 208b, when the physician further withdraws the needle 263, the tension in the suture 11 that pulls the second retainer 208b out of the needle 263 also pulls the second absorbable tube 358 out of the needle 263.

Figure 96:
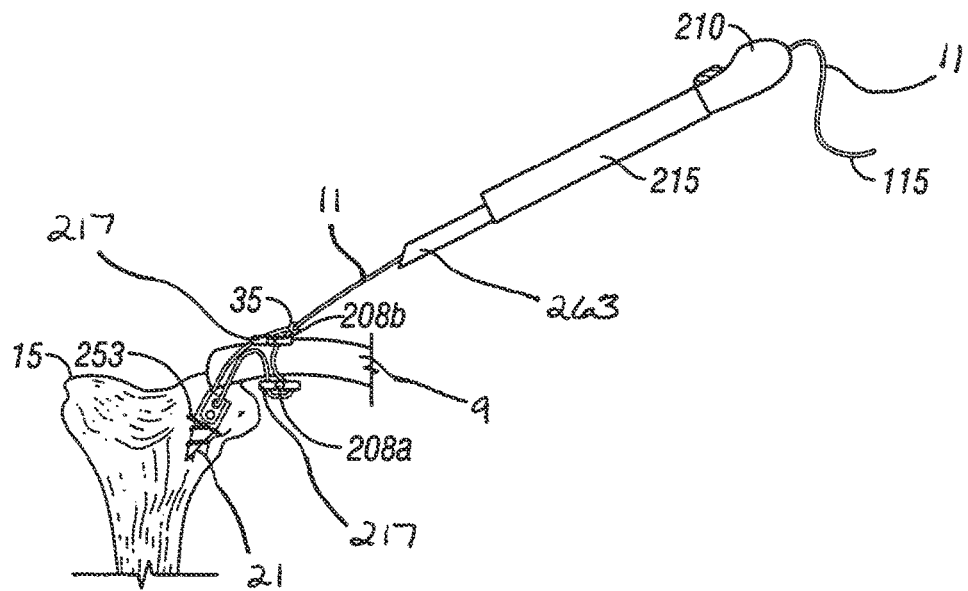
Figure 97:
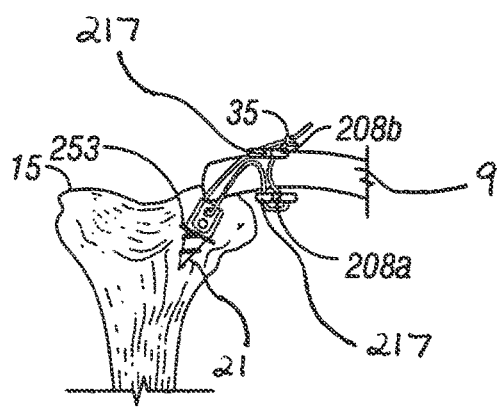

Referring to FIGS. 96 and 97, the physician tightens the slip knot 35, optionally using a knot pusher, as discussed above, to press the second retainer 208b firmly against the tendon 9, which presses the tendon tissue 9 firmly against the bone 15 within the decorticated trough to which it is being reattached. As the slip knot 35 is tightened, the distance between the retainers 208a, 208b is reduced and the distance between the fastener 21 and the retainers 208a, 208b is reduced. In reducing these distances, the tendon tissue 9 is pulled into the decorticated trough 253 and into contact with the bone tissue adjacent to the fastener 21. Moreover, the retainers 208a, 208b are pressed flush against the tendon tissue 9 to have a low profile, t. In this manner, even if there initially was insufficient tendon tissue or insufficient quality tendon tissue near the bone, the surgical assembly 205 pulls the detached tendon tissue 9 into the decorticated trough 253 such that quality tendon tissue 9 is reattached. After tightening the slip knot 35, the physician cuts the suture 11 adjacent to the slip knot 130 and removes the delivery device 267.

Figure 98:
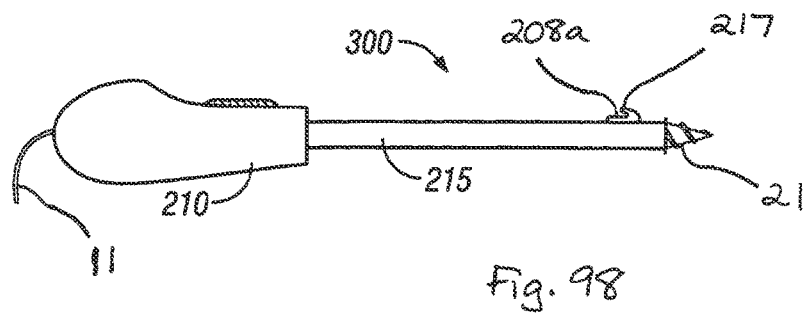
FIGS. 98 and 99 are an alternative embodiment of a surgical assembly including a fastener and a barbed retainer connected by a suture having a slip knot.
Figure 99:
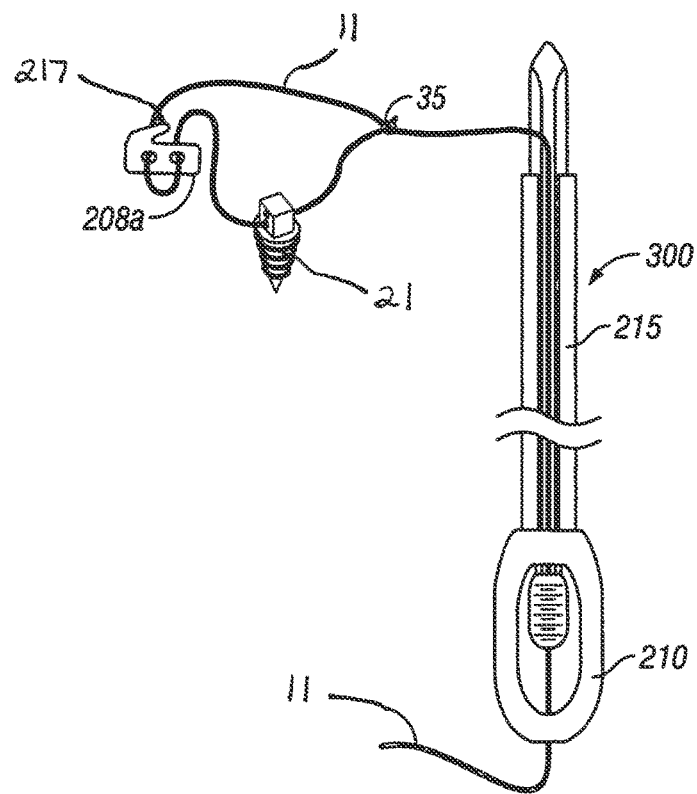

Referring to FIGS. 98 and 99, a delivery device 300 is used to place the fastener 21 and a single barbed retainer 208a instead of two barbed retainers 208a, 208b. In this embodiment, both the fastener 21 and the retainer 208a are placed between the bone 15 and the tissue that is being reattached to the bone 15 (as illustrated in FIG. 94). The suture 11 passes though and over the tissue between the fastener 21 and the retainer 208a to compress the tissue against the bone 15. Because there is only one retainer 208a, which is positioned under the tendon, only the slip knot 35 remains on the outer or upper surface of the tendon 9.

Figure 100:
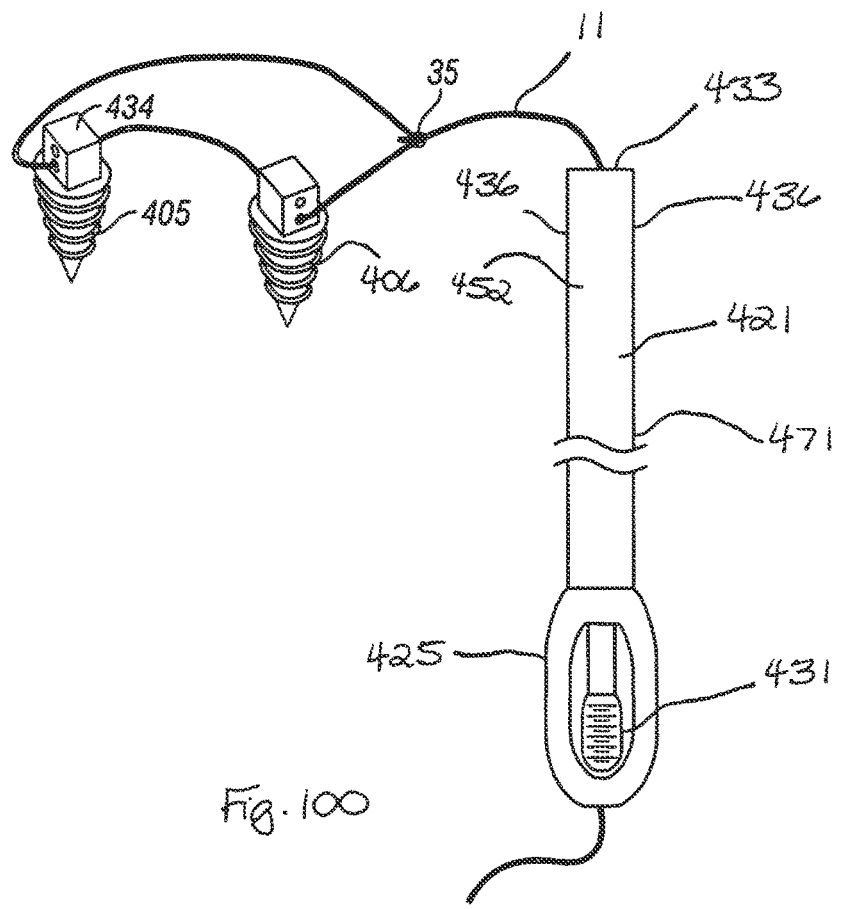
FIG. 100 illustrates an alternative embodiment of a surgical assembly including a pair of fasteners connected by a suture having a slip knot.

Referring to FIG. 100, a delivery device 471 for placing fasteners 405, 406 joined by the suture 11 and the slip knot 35 includes a cannula 421, a handle 425, and a thumb activated pusher rod 431. The cannula 421 and the fastener 406 are keyed to limit relative rotation.

Figure 101:
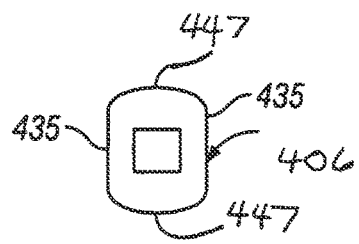
FIGS. 101 and 102 illustrate top and bottom views, respectively, of the fastener of FIG. 100.
Figure 102:
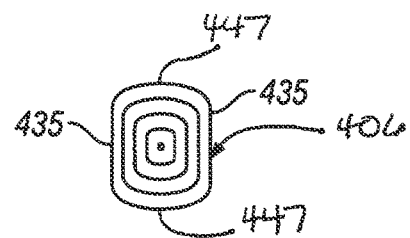
Figure 103:
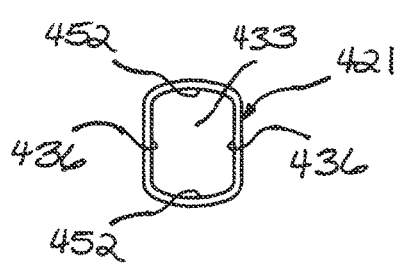
FIGS. 103 and 104 illustrate end views of two implementations of a cannula of a delivery device of the surgical assembly of FIG. 41.
Figure 104:
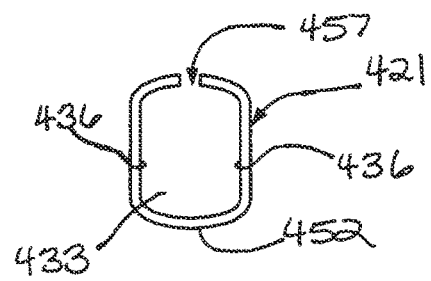

For example, referring to FIGS. 101-104, a bore 433 of the cannula 421 is rectangular and the fastener 406 is rectangular along its entire length. To provide the rectangular shape to the shaped fastener 406, the threads are machined to have rectangular sides. The fastener 405 has a rectangular head 434. Referring to FIGS. 101-103, the fastener 406 and the bore 433 each have a pair of generally straight parallel walls 435, 436, respectively, and a pair of curved, oppositely placed walls 447, 452, respectively. The straight walls 435 of the fastener 406 are aligned with the straight walls 436 of the cannula 421 to prevent rotation of the fastener 406 when it is positioned within the shaped bore 433 of the shaped cannula 421. The threads are flattened, cut or otherwise shaped along the entire length of the shank or along only a portion of the length of the shank. The fastener 406 has a slightly smaller cross-sectional profile such that the fastener 406 slides smoothly within the bore 433 of the cannula 421. As illustrated in FIG. 104, the cannula 421 includes a slot 457 along its length through which the suture 11 passes.

In another implementation, the cannula 421 and the fastener 406 are formed with mating polygonal cross sections to limit relative rotation. Thus, for example, the bore 433 of the cannula 421 can be hexagonal and the fastener 406 can be hexagonal along its entire length. To provide the hexagonal shape to the shaped fastener 406, the threads are machined to have hexagonal sides. Additionally, in this example, the fastener 405 has a hexagonal head 434.

To place the fasteners 405 and 406, the physician places the first fastener 405 through the tendon tissue 9 into the bone 15 in an analogous manner as described above. The physician advances the shaped fastener 406 in the shaped bore 433 of the cannula 421 by advancing the thumb-activated pusher rod 431 from a first retracted position to a second extended position. In the second, extended position the shaped fastener 406 is advanced such that the distal end of the fastener 406 extends out of the cannula 421 and a portion of the shank remains keyed within the shaped bore 433. The physician then presses the shaped fastener 406 through the tendon tissue 9 and screws it into the bone 15, as described above. Because the fastener 406 is keyed to the shaped bore 433 of the cannula 421 because of the mating shape, the shaped fastener 406 will not rotate relative to the cannula 421. The ability of the shaped fastener 406 not to rotate relative to the cannula 421 limits the amount of twisting that is imparted in the suture 11 as well as allows the shaped fastener 406 to be advanced within the cannula 421 and be rotated with the cannula 421. The physician then withdraws the delivery device 471, which pulls the slip knot 35 from the cannula 421, tightens the slip knot 35 against the tissue 9 using an optional knot pusher, and cuts the suture 11 at a position adjacent proximal to the slip knot 35.

Figure 105:
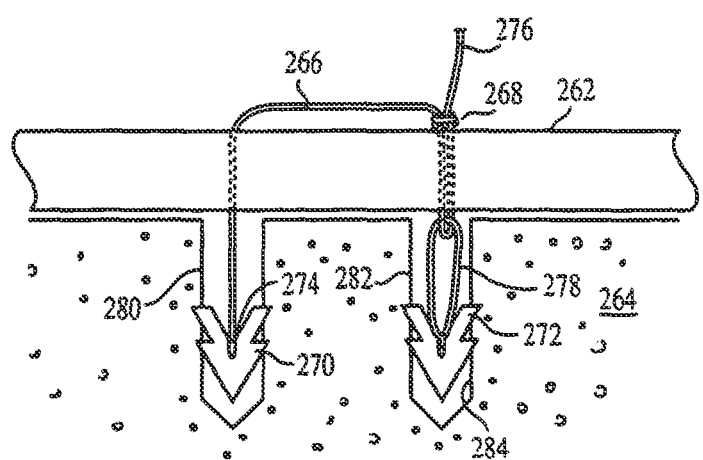
FIG. 105 is an illustration of an alternative embodiment of a closure device for use in attaching soft tissue to bone.

Referring to FIG. 105, in another implementation for securing soft tissue 262 to bone 264, a suture 266 is attached to two fixation members in the form of a first fastener 270 and a second fastener 272. The fasteners 270, 272 are, for example, TAG WEDGE bone anchors available from Smith & Nephew, Inc. Endoscopy Division, Andover, Mass. Other bone anchors known in the art can be employed as the fasteners 270, 272. Suture 266 has a first end 274 fixed to the fastener 270, a second free end 276, and a slip knot 268, formed as described above for slip knot 28. Suture 266 preferably passes through a separate suture loop 278, rather than through the member 272 itself. Suture loop 278 acts as a good pulley allowing suture 266 to slide relative to suture loop 278.

In use, the user forms bone holes 280, 282 in bone 264. The user then implants the fastener 270 in bone hole 280, with suture 266 already threaded as shown, followed by implanting the fastener 272 in bone hole 282. The user then pulls on free end 276 of suture 266, which brings soft tissue 262 against bone 264. Slip knot 268 limits loosening of suture 266. By using suture loop 278, suture 266 is not located within bone hole 282 in use thus limiting the possibility of trapping suture 266 against wall 284 of bone hole 282. If suture 266 were trapped in bone hole 282, pulling free end 276 of suture 266 would not result in shortening the length of suture between fasteners 270, 272, which acts to secure soft tissue 262 against bone 264.

Figure 106:
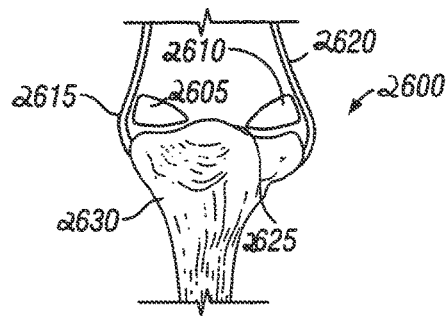
FIG. 106 is a side view of a knee joint in which there is laxity in the lateral collateral ligament.

Referring to FIG. 106, a knee joint 2600 includes a first meniscus 2605, a second meniscus 2610, a first ligament 2615, and a second ligament 2620, the lateral collateral ligament. The first meniscus 2605 and the first ligament 2615 illustrate the normal position of the meniscus and ligament relative to each other and to an upper surface 2625 of the tibia 2630. In contrast, the second ligament 2620 extends outwardly from its normal position due to laxity in the ligament 2620. As a result of the laxity in the second ligament 2620, the second meniscus 2610 is dislodged from its normal position relative to the upper surface 2625 of the tibia 2630.

Figure 107:
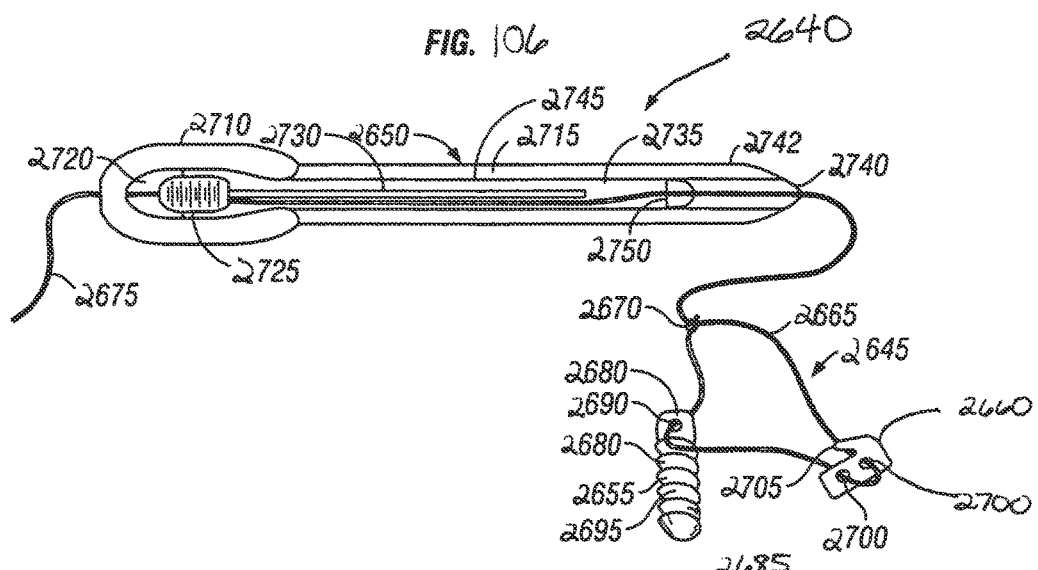
FIG. 107 is a top view of a surgical assembly that includes a delivery device and a surgical device for repairing laxity in the lateral collateral ligament of FIG. 106.
Figure 108:
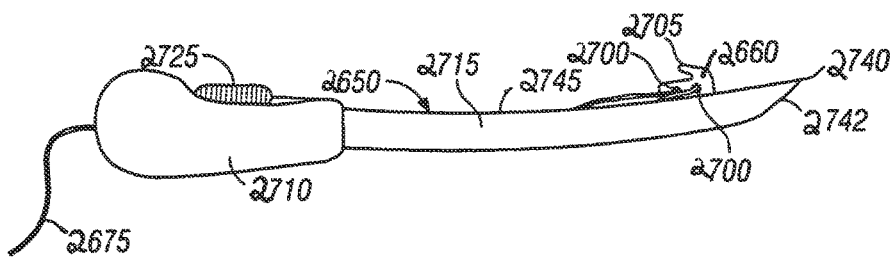
FIG. 108 is a side view of the surgical assembly of FIG. 107.
Figure 109:
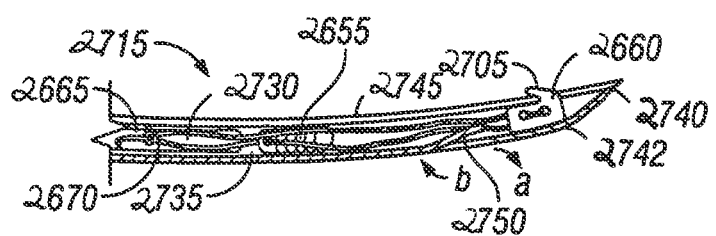
FIG. 109 is a cross-sectional side view of the distal end of the surgical device of FIG. 107.

Referring to FIGS. 107-109, a surgical assembly 2640 used to correct laxity in the ligament 2620 includes a surgical device 2645 and a delivery device 2650. The surgical device 2645 includes a fixation member in the form of a fastener 2655, a fixation member in the form of a retainer 2660, and a flexible member, such as a suture 2665. The suture 2665 couples the fastener 2655 and the retainer 2660, and is tied in a limiting element such as a slip knot 2670 such that the distance between the fastener 2655 and the retainer 2660 can be shortened but not lengthened by pulling on a free end 2675 of the suture 2665. The fastener 2655 includes a head 2680 and a shank 2685. The head 2680 includes an opening 2690 through which the suture 2665 passes. The shank 2685 includes circumferential ridges 2695 that resist pullout of the fastener 2655 when the fastener 2655 is implanted in bone. The retainer 2660 includes a pair of openings 2700 through which the suture passes and a tab 2705 that extends from the retainer 2660. The retainer 2660 is a low profile retainer and has a thickness of between approximately 0.5 and 2.5 millimeters, and more particularly of approximately 2 millimeters.

The delivery device 2650 includes a handle 2710 and a cannula 2715 that extends from the handle 2710. The handle 2650 includes an opening 2720 in which a thumb switch 2725 slides to advance and retract a pusher tube 2730 that is connected to the thumb switch 2725. The cannula 2715 includes an inner lumen 2735 that extends from the opening 2720 in the handle 2650 to a sharp, distal tip 2740 at a curved distal end 2742. A longitudinal slot 2745 opens from outside the cannula 2715 into the inner lumen 2735. The inner lumen 2735 receives the fastener 2655, the retainer 2660, the suture 2665, and the slip knot 2670. The suture 2665 is placed first within the inner lumen 2735 and pulled through the handle 2710. The slip knot 2670 is placed next within the inner lumen 2735. The fastener 2665 is placed next within the inner lumen 2735 in an orientation with the shank 2685 distal to the head 2680. Finally, the retainer 2660 is placed within the inner lumen 2735 with the tab 2705 passing through the longitudinal slot 2745.

The suture 2665 extends through the cannula 2715 and the handle 2710 such that the free end 2675 passes outside of the delivery device 2650. The cannula 2715 also includes a stop 2750 positioned within the inner lumen 2735 between the fastener 2655 and the retainer 2660. Referring particularly to FIG. 109, the stop 2750 is cut from the cannula and can be pressed down in a first direction, a, by the exertion of force against the stop, such as by advancing the fastener 2655 distally over the stop 2750. The necessity to apply force to pass the fastener 2655 over the stop 2750 prevents the fastener 2655 from being accidentally dislodged. Although the stop 2750 can be pressed forward in the first direction, a, the stop 2750 cannot easily, if at all, be pressed backward in a second opposite direction, b.

To dislodge the fastener 2655 from the cannula 2715, the physician advances the thumb switch 2725, which advances the pusher tube 2730 and forces the fastener 2655 over and past the stop 2750. The stop 2750 prevents the fastener 2655 from being pushed back into the cannula 2715 once it is pushed distal of the stop 2750. Because the stop 2750 prevents backwards movement of the fastener 2655, the delivery device 2650 can be used to press the fastener 2655 into bone tissue, as described in more detail below.

Figure 110:
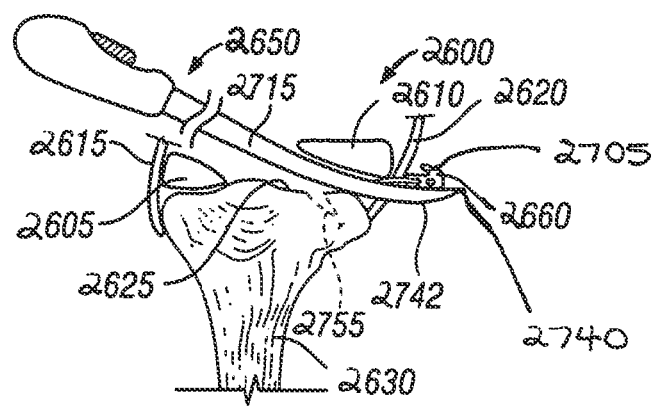
FIGS. 110-114 illustrate the surgical device of FIG. 107 in use repairing laxity in the lateral collateral ligament of FIG. 106.

Referring to FIG. 110, the physician initially accesses the knee joint 2600, for example, using arthroscopic techniques, and drills a guide hole 2755 into the upper surface 2625 of the bone 2630 into which the fastener 2655 is to be placed. The physician then advances the delivery device 2650 into the knee joint 2600 and positions the cannula 2715 underneath the second meniscus 2610 until the sharp, distal tip 2740 is pressed against the ligament 2620. The physician then advances the cannula 2715 into the second ligament 2620 by forcing the sharp, distal tip 2740 through the ligament 2620. The physician continues to advance the cannula 2715 sufficiently such that the retainer 2660 is pushed completely through the ligament 2620. The physician then retracts the delivery device 2650 enough to pull the cannula 2715 out of the ligament 2620. In pulling back the cannula 2715, the tab 2705 that extends from the retainer 2660 catches the ligament 2620, thereby dislodging the retainer 2660 from the cannula 2715.

Figure 111:
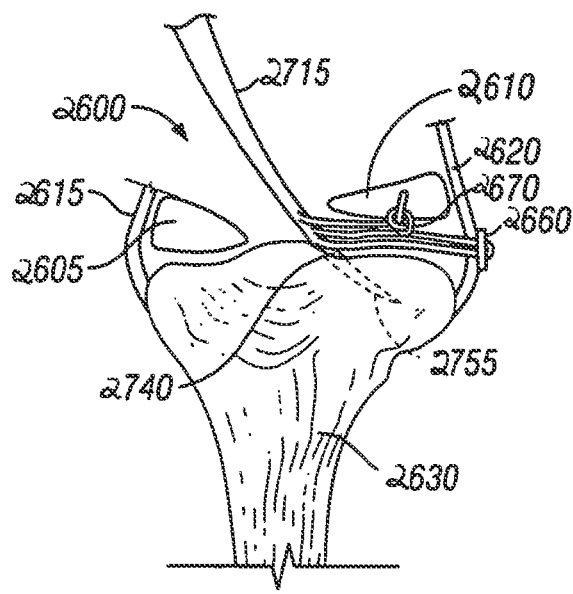

Referring to FIG. 111, the physician next positions the delivery device 2650 within the knee joint 2600 such that the sharp, distal tip 2740 is brought up to or inserted into the guide hole 2755. With the tip 2740 in this position, the physician advances the thumb switch 2725 to push the fastener 2655 out of the lumen 2735 and into the guide hole 2755.

Figure 112:
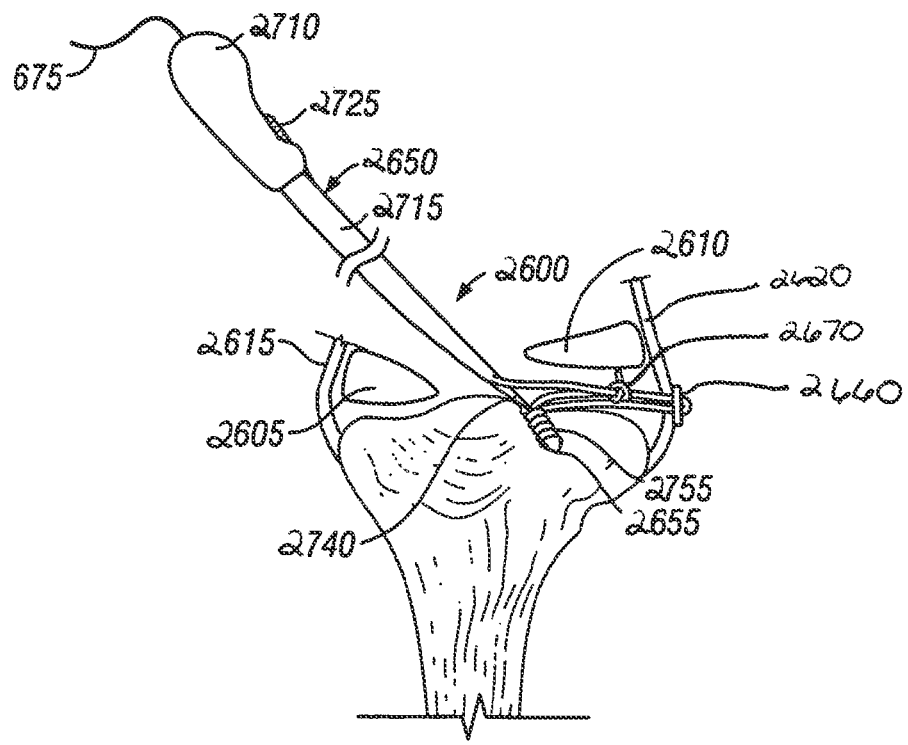

Referring to FIG. 112, the physician then presses the fastener 2655 deeper into the guide hole 2755. To press the fastener 2655 into the guide hole 2755, the physician rests the stop 2750 against the head 2680 of the fastener 2655 and applies force to the delivery device 2650. Because the stop 2750 will not bend backwards, the force applied to the stop 2750 will be transmitted to the fastener 2655 and will thereby force the fastener 2655 into the guide hole 2755. The physician may need to further advance the thumb switch 2725 to advance the pusher rod 2730 to ensure that the fastener 2655 is completely within the guide hole 2755.

Figure 113:
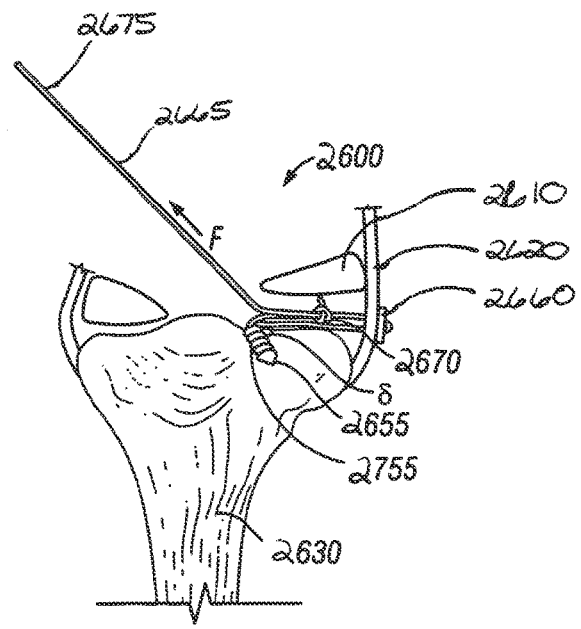
Figure 114:
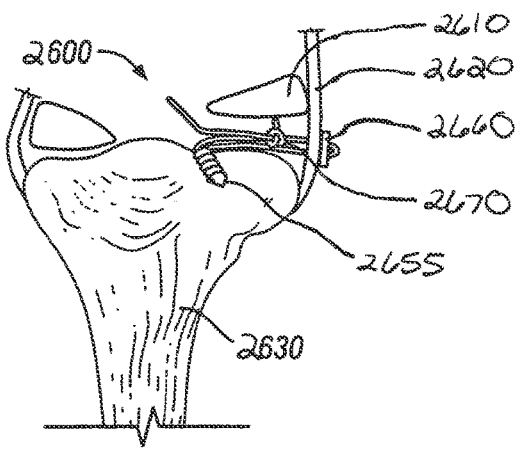

Referring to FIG. 113, after placing the fastener 2665, the physician withdraws the delivery device 2650 from the knee joint 2600, leaving the fastener 2655 within the bone 2630 and the retainer 2660 against the ligament 2620. The slip knot 2670 is positioned underneath the meniscus 2610 between the retainer 2660 and the fastener 2655 and the remainder of the suture 2665 extends out of the knee joint 2600. The fastener 2655 is positioned within the bone 2630 at an angle δ that is at ninety degrees or less relative to the suture 2665 that passes between the retainer 2660 and the fastener 2655. An angle δ of ninety degrees or less opposes a force that would tend to pull the fastener 2655 out of the bone 2630. The physician next pulls the free end 2675 of the suture 2665 in a direction, F, which shortens the distance between the fastener 2655 and the retainer 2660 as the slip knot 2670 is pulled toward the fastener 2655. Referring to FIG. 114, shortening the distance between the fastener 2655 and the retainer 2660 pulls the retainer 2660 in the direction of the fastener 2655, thus, moving the ligament 2620 and the meniscus 2610 inward, which corrects the misplacement of the meniscus 2610. The physician then cuts the suture 2665 at a position adjacent to, but proximal of, the slip knot 2670, which tends to remain underneath the meniscus 2610.

Figure 115:
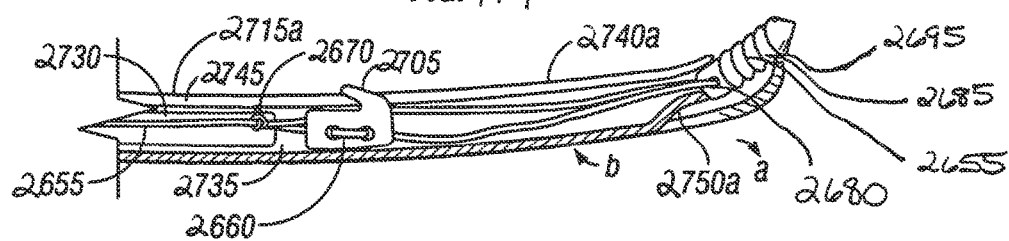
FIG. 115 is a cross-sectional side view of the distal end of a modified version of the surgical device of FIG. 107.

FIGS. 106-114 illustrate a method of repairing the laxity in the ligament 2620 and the displaced meniscus 2610 by placing the retainer 2660 before the fastener 2655. Nonetheless, the order in which the retainer 2660 and the fastener 2655 are placed can be reversed. For example, by modifying the cannula 2715 and placing the retainer 2660 in the cannula 2715 before the fastener 2655 is placed in the cannula 2715, the fastener 2655 can be placed in the bone 2630 before the retainer 2660 is placed against the ligament 2620. In particular, referring to FIG. 115, a cannula 2715a has a stop 2750a positioned closer to a sharp, distal tip 2740a than to stop 2750 of the cannula 2715. By placing the stop 2750a in a more distal position, the stop 2750a limits the likelihood that the fastener 2655 will retract into the cannula 2715a when it is forcibly inserted into the guide hole 2755.

Figure 116:
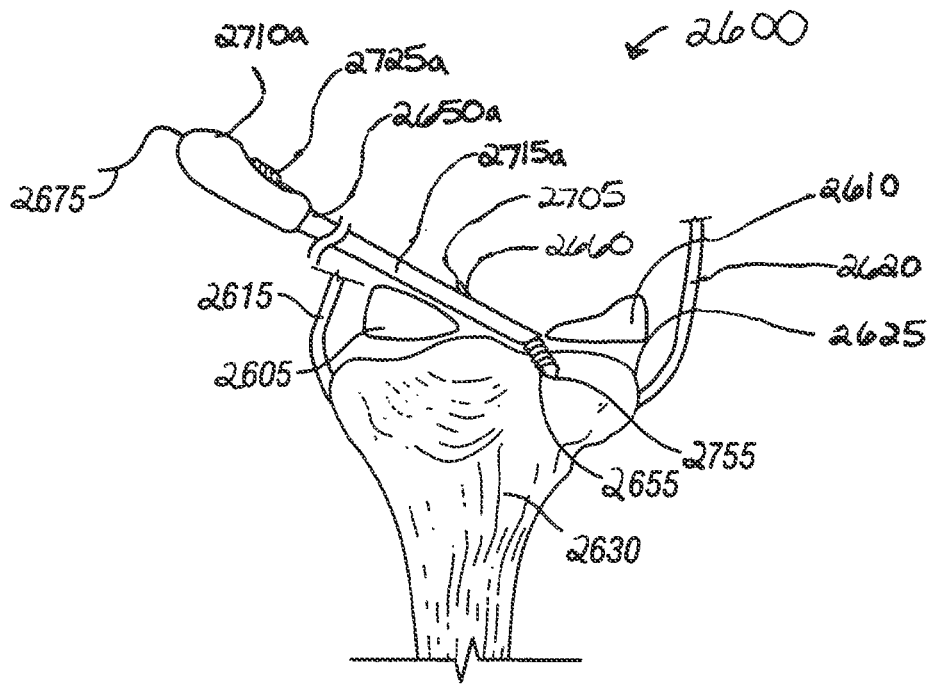
FIGS. 116 and 117 illustrate the surgical device of FIG. 115 in use repairing laxity in the lateral collateral ligament of FIG. 106.

Referring to FIG. 116, in the manner described above, the physician initially accesses the knee joint 2600 and drills a guide hole 2755 into the upper surface 2625 of the bone 2630 into which the fastener 2655 is to be placed. The physician then advances the delivery device 2650a into the knee joint 2600 and positions the delivery device 2650a within the knee joint 2600 such that the fastener 2655 and the sharp, distal tip 2740a are inserted into the guide hole 2755. With the tip 2740a in this position, the physician advances the delivery device 2650a to further press the fastener 2655 into the guide hole 2755. The physician then retracts the delivery device 2650a from the guide hole 2755. Because the fastener 2655 includes circumferential ridges 2695 that are wedged into the bone 2630 surrounding the guide hole 2755, the fastener 2655 will resist pullout when the delivery device 2650a is retracted. To ensure that the fastener 2655 is placed sufficiently within the guide hole 2755, the physician presses the fastener 2655 deeper into the guide hole 2755. Because the stop 2750a will not bend backwards, the force applied to the stop 2750a will be transmitted to the fastener 2655 and will thereby force the fastener 2655 further into the guide hole 2755.

Figure 117:
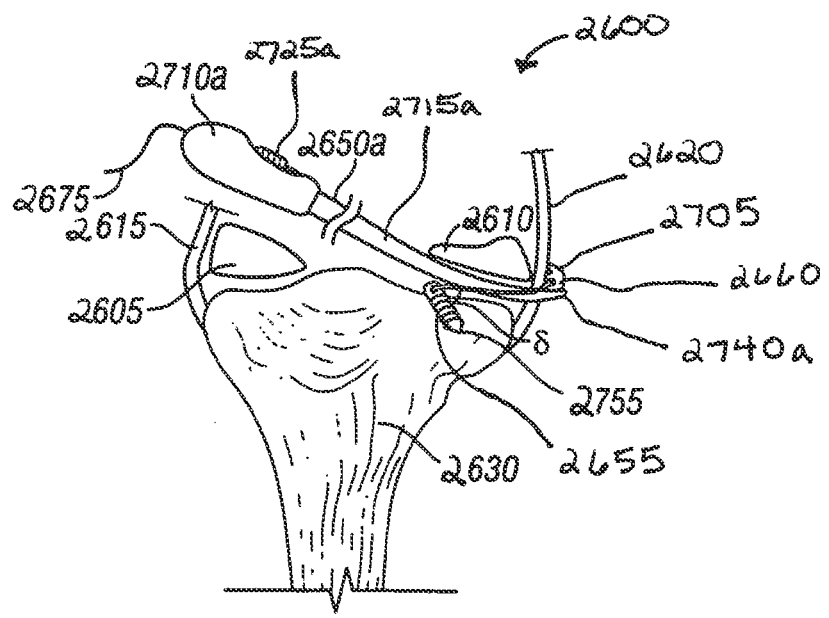

Referring to FIG. 117, the physician next positions the cannula 2715a underneath the second meniscus 2610 and advances the cannula until the sharp, distal tip 2740a is pressed against the ligament 2620. The physician then advances the cannula 2715a into the ligament 2620 by forcing the sharp, distal tip 2740a through the ligament 2620 while pressing the thumb switch 2725a forward to advance the pusher rod 2730a and pass the retainer 2660 over the stop 2750a. The physician continues to advance the cannula 2715a sufficiently such that the retainer 2660 is pushed completely through the ligament 2620. The physician then retracts the delivery device 2650a enough to pull the cannula 2715a out of the ligament 2620. In pulling back the cannula 2715a, the tab 2750a that extends from the retainer 2660 catches the ligament 2620, thereby dislodging the retainer 2660 from the cannula 2715a.

As described above with respect to FIG. 113, after placing the retainer 2660, the physician withdraws the delivery device 2650a from the knee joint 2600, leaving the fastener 2655 within the bone 2630 and the retainer 2660 against the ligament 2620. The fastener 2655 is positioned within the bone 2630 at an angle, δ, that is, at ninety degrees or less relative to the suture 2665 that passes between the retainer 2660 and the fastener 2655. The slip knot 2670 is positioned underneath the meniscus 2610 between the retainer 2660 and the fastener 2655 and the remainder of the suture 2665 extends out of the knee joint 2600. The physician next pulls the free end 2675 of the suture 2665 in a direction, F, which shortens the distance between the fastener 2655 and the retainer 2660 as the slip knot 2670 is pulled toward the fastener 2655. As described above with respect to FIG. 114, shortening the distance between the fastener 2655 and the retainer 2660 pulls the retainer 2660 in the direction of the fastener 2655. Pulling the retainer 2660 pulls the ligament 2620 and the meniscus 2610 inwardly, which corrects the misplacement of the meniscus 2610. The physician then cuts the suture 2665 at a position adjacent to, but proximal of, the slip knot 2670, which tends to remain underneath the meniscus 2610.

Figure 118:
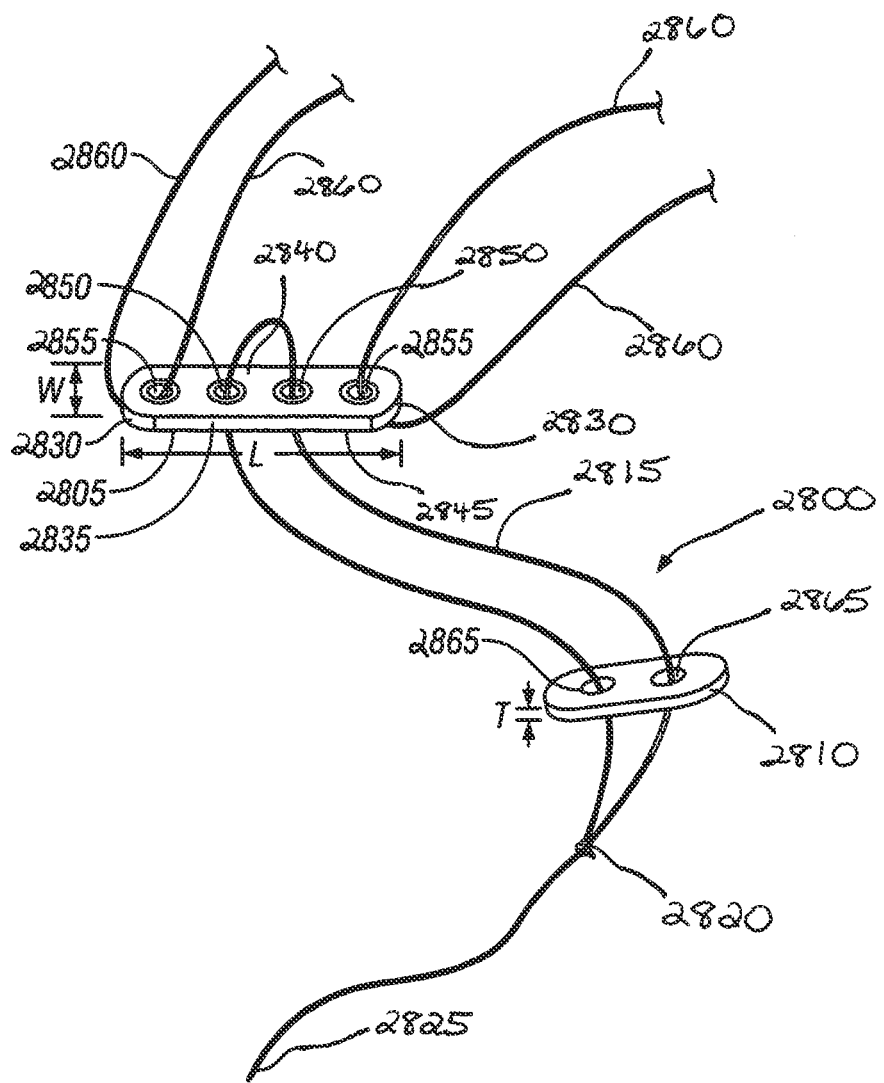
FIG. 118 illustrates a surgical device having a button-shaped fastener.

Referring to FIGS. 118-123, one of the fixation members 2805 of a repair device 2800 can be shaped like a button and passed through a channel for repairing a tear in soft tissue. Referring to FIG. 118, a surgical device 2800 includes a fixation member such as a retainer 2805 in the shape of a button, a fixation member such as a retainer 2810, and a flexible member, such as a suture 2815. The suture 2815 couples the retainer 2805 and the retainer 2810, and is tied in a slip knot 2820 such that the distance between the retainer 2805 and the retainer 2810 can be shortened but not lengthened by pulling on a free end 2825 of the suture 2815. The retainer 2805 includes a pair of width edges 2830, a pair of length edges 2835, an upper surface 2840, a lower surface 2845, a pair of inner openings 2850 passing between the upper surface 2840 and the lower surface 2845, and a pair of outer openings 2855 passing between the upper surface 2840 and the lower surface 2845. The retainer has a length, L, of between approximately 18-22 mm and a width, W, of between approximately 2-6 mm. The suture 2815 passes through the inner openings 2850. A pair of sutures 2860 pass through each of the outer openings 2855 and are used to flip the retainer 2805, as described below. The retainer 2810 includes a pair of openings 2865 through which the suture 2815 passes. The retainer 2810 is a low profile retainer and has a thickness, T, of between approximately 0.5 and 2.5 millimeters, and more particularly of approximately 2 millimeters.

Figure 119:
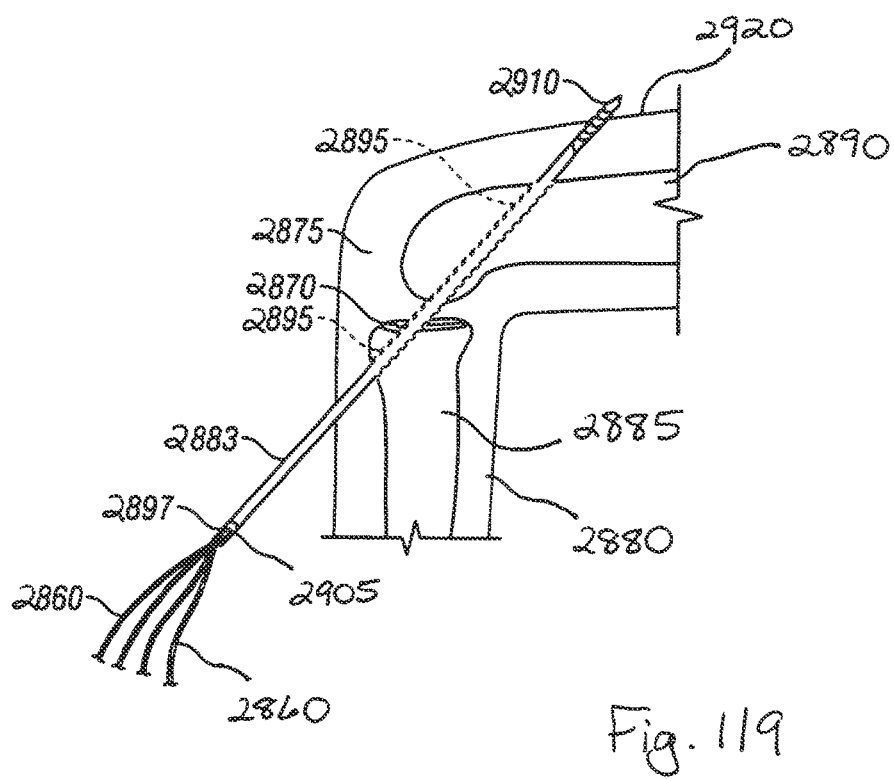
FIG. 119 illustrates the drilling of a channel through the tibia and femur.
Figure 120:
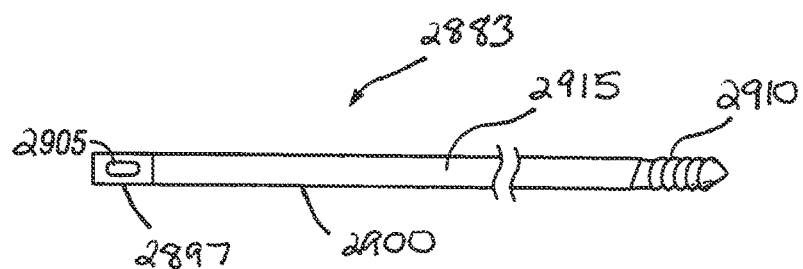
FIG. 120 is a side view of a drill used to perform the drilling of FIG. 119.

Referring to FIGS. 119 and 120, the physician uses a surgical device to repair, for example, a tear in the meniscus 2870 of the knee joint 2875. Initially, the physician makes a surgical incision on the anterior surface of the lower leg 2880 and passes a drill 2883 through the tibia 2885, the meniscus 2870, and the femur 2890 to form a channel 2895 through the tibia 2885, the meniscus 2870, and the femur 2890. The drill 2883 includes a head 2897 and a shank 2900. The head 2897 includes an opening 2905 for receiving sutures 2860 and the shank 2900 includes a cutting section 2910 and a smooth section 2915.

Figure 121:
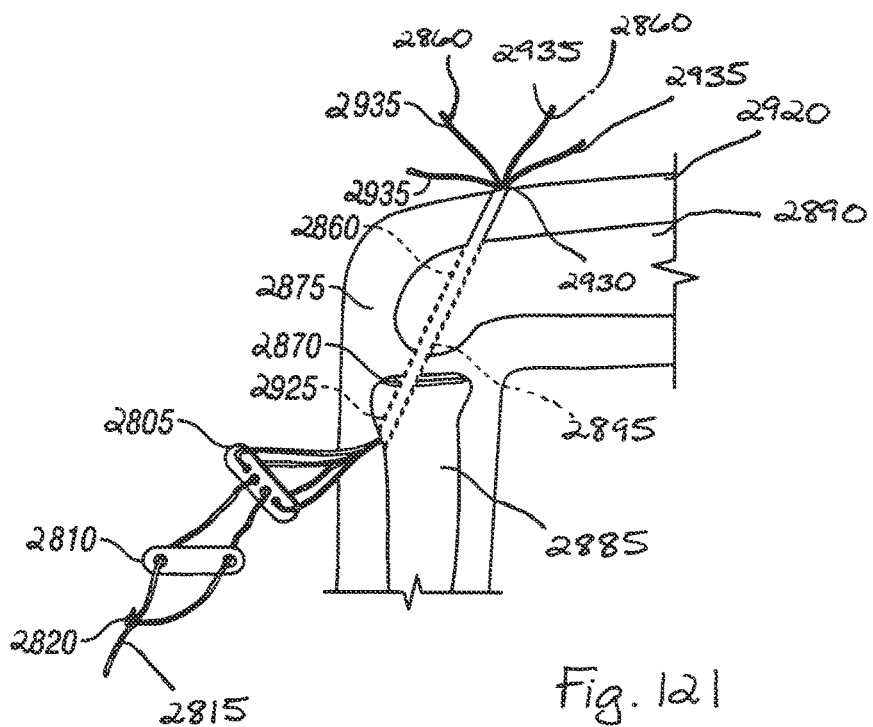
FIGS. 121-123 illustrate the placement of the surgical device of FIG. 118 in the knee joint to repair a torn meniscus.

Referring also to FIG. 121, once the physician passes the cutting section 2910 through the femur 2890 and the skin 2920, the physician removes the drill 2883 from the handle or other device used to advance the drill 2883. The physician then passes the free ends of the sutures 2860 coupled to retainer 2805 through the opening 2905 and advances the drill 2883 along the channel 2895 until the drill 2883 is completely advanced through and out of the channel 2895. The sutures 2860 now extend between a first opening 2925 of the channel 2895 and a second opening 2930 of the channel 2895. Specifically, free ends 2935 of the sutures 2860 extend from the second opening 2930. The mid-section of the sutures 2860 extend from the first opening 2925 and pass through the outer openings 2855 of the retainer 2805. The physician then inserts the retainer 2805 lengthwise into the channel 2895 and pulls the free ends 2935 of the sutures 2860 to pull the retainer 2805 into the channel 2895. The physician continues to pull the free ends 2935 until the retainer 2805 passes through the tibia 2885 and the meniscus 2870, and is within the knee joint 2875.

Figure 122:
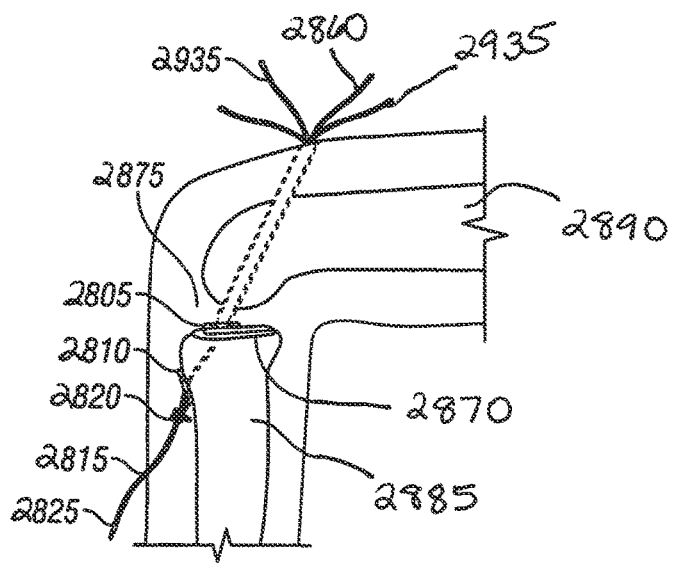
Figure 123:
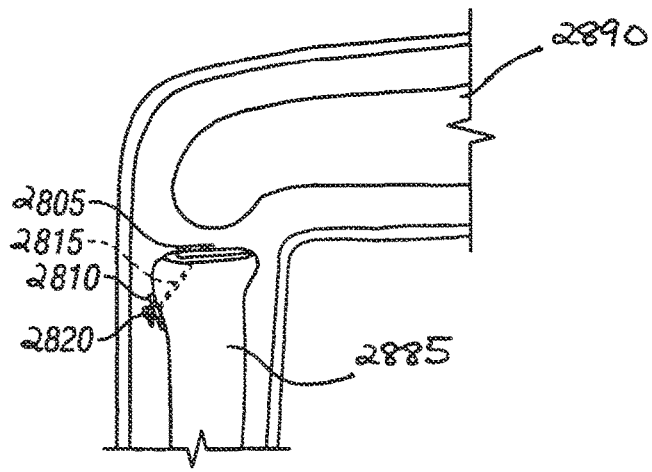

Referring to FIG. 122, to position the retainer 2805 against the meniscus 2870 within the knee joint 2875, the physician pulls on the suture 2815, which pulls the retainer 2805 back in the direction of the meniscus 2870 and the tibia 2885. To ensure that the retainer 2805 is not pulled back into the channel 2895, the physician changes the orientation of the retainer 2805 to be transverse to the channel 2895 by pulling on the sutures 2860. The physician pulls on one of the sutures 2860 more than the other suture 2860 to rotate the retainer 2805 within the joint. The physician then pulls the free end 2825 of the suture 2815, which moves the slip knot 2820 to shorten the distance between the retainer 2805 and the retainer 2810. The physician continues to pull on the free end 2825 until the retainer 2810 is pressed against the first opening 2925, which presses the retainer 2805 against the meniscus 2870 to repair the tear in the meniscus 2870. Referring to FIG. 123, to complete the procedure, the physician cuts the suture 2815 adjacent to the slip knot 2820 and pulls one free end 2935 of each suture 2860, which pulls the sutures 2860 out of the retainer 2805.

Figure 124:
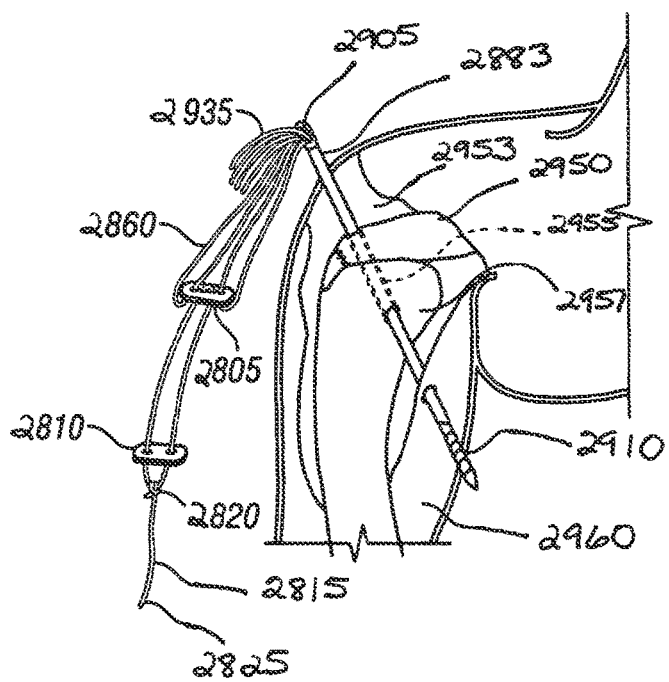
FIGS. 124-127 illustrate the placement of the surgical device of FIG. 118 in the shoulder joint to repair a torn rotator cuff.

The surgical device 2800 also can be used in a similar manner to repair other tissue within the body. For example, referring to FIGS. 124-127, the surgical device 2800 can be used to repair a torn rotator cuff 2950 in the shoulder joint 2953. Referring to FIG. 124, the physician initially makes an incision to access the rotator cuff 2950 and then uses the drill 2883 to drill a channel 2955 through the rotator cuff 2950, the humerus head 2957, and the skin 2960. When the cutting section 2910 passes through the skin 2960, the physician removes the tool (for example, handle) used to drive the drill 2883 and passes the sutures 2860 through the opening 2905.

Figure 125:
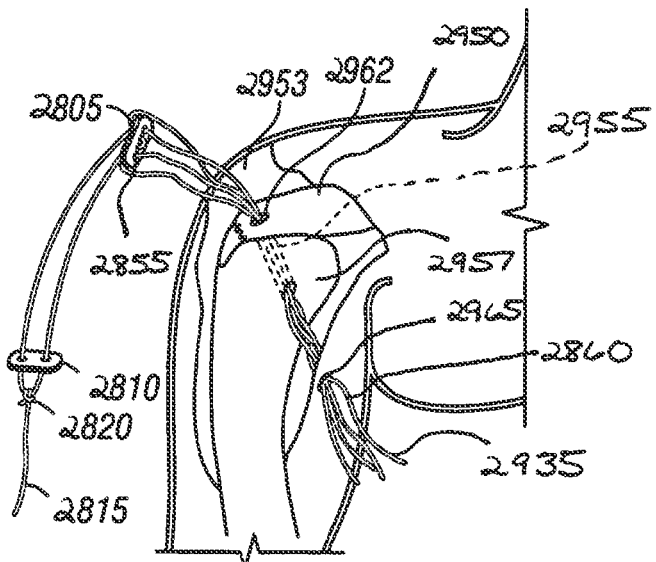

Referring to FIG. 125, the physician then advances the drill 2883 completely through the channel 2955 pulling the free ends of the sutures 2860 couple to openings 2855 of retainer 2805 through the skin 2960. The sutures 2860 extend between a first opening 2962 of the channel 2955 and a second opening 2965 of the channel 2955. The second opening 2965 is in the skin 2960. Specifically, free ends 2935 of the sutures 2860 extend from the second opening 2930. The physician then inserts the retainer 2805 lengthwise into the channel 2955 and pulls the free ends 2935 of the sutures 2860 to pull the retainer 2805 through the channel 2955. The physician continues to pull the free ends 2935 until the retainer 2805 passes through the rotator cuff 2950 and the humerus head 2957 and is positioned between the skin 2960 and the humerus head 2957.

Figure 126:
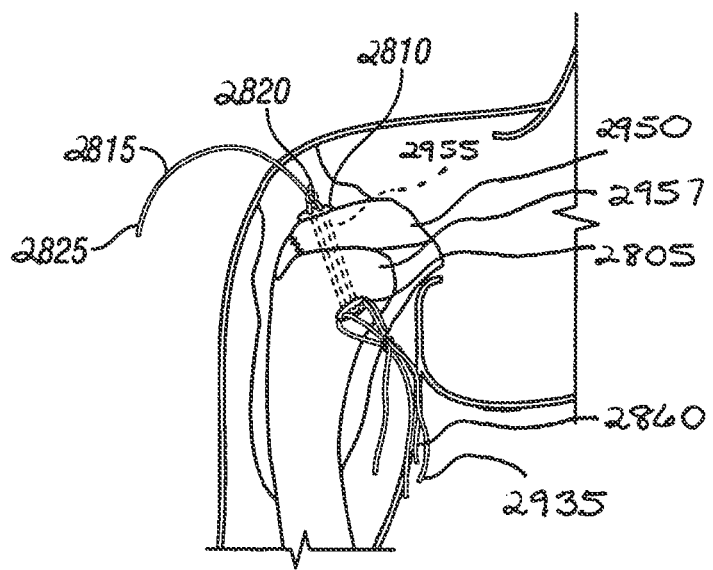

Referring to FIG. 126, to position the retainer 2805 against the humerus head 2957, the physician pulls on the suture 2815, which pulls the retainer 2805 in the direction of the humerus head 2957. To ensure that the retainer 2805 is not pulled back into the channel 2955, the physician changes the orientation of the retainer 2805 to be transverse to the channel 2955 by pulling on the sutures 2860. To change the orientation, the physician can pull on one of the sutures 2860 more than the other suture 2860 to rotate the retainer 2805. The physician then pulls the free end 2825 of the suture 2815, which moves the slip knot 2820 to shorten the distance between the retainer 2805 and the retainer 2810. The physician continues to pull on the free end 2825 until the retainer 2810 is pressed against the first opening 2962, which presses the retainer 2805 against the rotator cuff 2950 to repair the tear.

Figure 127:
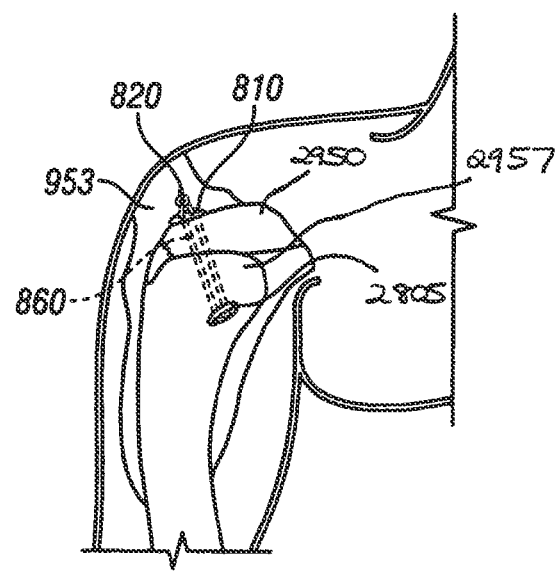

Referring to FIG. 127, to complete the procedure the physician cuts the suture 2815 adjacent to the slip knot 2820 and pulls one free end 2935 of each suture 2860, which pulls the sutures 2860 out of the retainer 2805.

Other embodiments are within the scope of the following claims. For example, although in certain embodiments the fastener is generally described and illustrated as a screw, other implementations of the fastener include an anchor, pound-in screw, or any other configuration that is insertable and retained within bone. The screw and cannula can be coupled by other than hexagonal shapes.

The fixation members, limiting elements, and flexible members of the above embodiments can be formed of a biodegradable material.

The devices and techniques described above can be applied to other anatomical regions to reattach tissue to bone or repair a tear in soft tissue, such as the biceps tendons, the lateral collateral ligament, the medial collateral ligament, the popliteal ligament, and the hip.

What is claimed is:
1. An apparatus for tissue repair, comprising:
a delivery device comprising a slotted needle including a first fixation member and a second fixation member;
a flexible coupling member coupling the first and second fixation members, the flexible coupling member having two terminal ends, the flexible coupling member slidably coupled to one of the first and second fixation members, and the other of said first and second fixation members substantially immovably attached to one of the two terminal ends, the other of the two terminal ends routed separately from the one of the two terminal ends, such that when the other of the two terminal ends of the flexible coupling member is pulled, a length of the flexible coupling member between the first and second fixation members is shortened; and
a Chinese trap formed in the flexible coupling member through which a portion of the flexible coupling member slides, the Chinese trap configured to tighten around the portion when the other of the two terminal ends of the flexible coupling member is pulled.

2. The apparatus of claim 1 comprising a closed loop of flexible material coupling one of the first and second fixation members to the flexible coupling member, the flexible coupling member being slidably received through the closed loop of flexible material.

3. The apparatus of claim 1 being preassembled for use in a surgical procedure.

4. The apparatus of claim 1 wherein the other of the two terminal ends of the flexible coupling member is slidably received within the Chinese trap.

5. The apparatus of claim 4 wherein when the other of the two terminal ends of the flexible coupling member is pulled, the Chinese trap is stretched and grips a portion of the flexible coupling member therethrough to limit movement of the flexible coupling member relative to the Chinese trap.

6. The apparatus of claim 1, wherein the delivery device comprises a removable cannula configured to permit placement of the delivery device and then be removed.

7. The apparatus of claim 6, wherein the removable cannula protects a distal tip of the delivery device during insertion into a patient.

8. The apparatus as in claim 1, wherein the delivery device comprises a rod for pushing one of the fixation members in a distal direction to position the one of the fixation members.

9. The apparatus as in claim 8, wherein the positioned fixation member slides distally from the needle during retraction of the needle.

10. The apparatus as in claim 9, wherein the flexible coupling is played out of the delivery device upon retraction of the needle.

* * * * *